United States Patent
Seul et al.

(10) Patent No.: US 10,407,718 B2
(45) Date of Patent: Sep. 10, 2019

(54) OPTIMIZATION OF GENE EXPRESSION ANALYSIS USING IMMOBILIZED CAPTURE PROBES

(71) Applicant: BioArray Solutions, Ltd., Warren, NJ (US)

(72) Inventors: Michael Seul, Fanwood, NJ (US); Sukanta Banerjee, Pennington, NJ (US); Jiacheng Yang, Hillsboro, NJ (US); Tatiana Vener, Stirling, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 0 days.

(21) Appl. No.: 15/491,127

(22) Filed: Apr. 19, 2017

(65) Prior Publication Data

US 2017/0218437 A1 Aug. 3, 2017

Related U.S. Application Data

(60) Division of application No. 14/257,294, filed on Apr. 21, 2014, now Pat. No. 9,637,777, which is a continuation of application No. 12/480,215, filed on Jun. 8, 2009, now Pat. No. 8,795,960, which is a continuation of application No. 10/974,036, filed on Oct. 26, 2004, now Pat. No. 7,563,569.

(60) Provisional application No. 60/544,533, filed on Feb. 14, 2004, provisional application No. 60/516,611, filed on Oct. 28, 2003.

(51) Int. Cl.
*C12Q 1/6832* (2018.01)
*C12Q 1/6809* (2018.01)
*C12Q 1/6834* (2018.01)
*C12Q 1/6837* (2018.01)

(52) U.S. Cl.
CPC ......... *C12Q 1/6832* (2013.01); *C12Q 1/6809* (2013.01); *C12Q 1/6834* (2013.01); *C12Q 1/6837* (2013.01); *B01J 2219/00459* (2013.01); *B01J 2219/00576* (2013.01); *B01J 2219/00608* (2013.01); *B01J 2219/00648* (2013.01); *B01J 2219/00722* (2013.01)

(58) Field of Classification Search
CPC ... C12Q 1/6832; C12Q 1/6809; C12Q 1/6834
See application file for complete search history.

(56) References Cited

U.S. PATENT DOCUMENTS

2002/0034753 A1* 3/2002 Yang .................... C12Q 1/6809 435/6.12

FOREIGN PATENT DOCUMENTS

WO    WO 03/034029    * 4/2003

* cited by examiner

*Primary Examiner* — Narayan K Bhat
(74) *Attorney, Agent, or Firm* — Mintz, Levin, Cohn, Ferris, Glovsky and Popeo, P.C.

(57) ABSTRACT

Disclosed are methods of multiplexed analysis of oligonucleotides in a sample, including a method of preventing a significant reduction in duplexes detectable in a hybridization assay involving (i) selecting probe lengths for sets of oligonucleotide probes, wherein probes include different subsequences such that at least one subsequence is complementary to a subsequence in a cognate target; wherein probes for longer cognate targets are longer in length than probes for shorter cognate targets, (ii) selecting, for each set of probes, a density of oligonucleotides probes attached per unit area on a solid phase carrier which is below a limit at which the significant reduction in detectable duplexes is predicated to take place, (iii) producing the probes and affixing them to different solid phase carriers at the selected density, and (iv) annealing targets to the probes, wherein signal intensities of probes and targets of different lengths are about the same.

4 Claims, 31 Drawing Sheets

Specification includes a Sequence Listing.

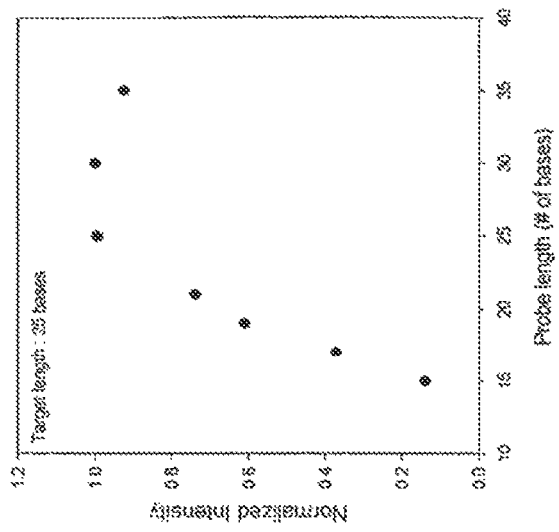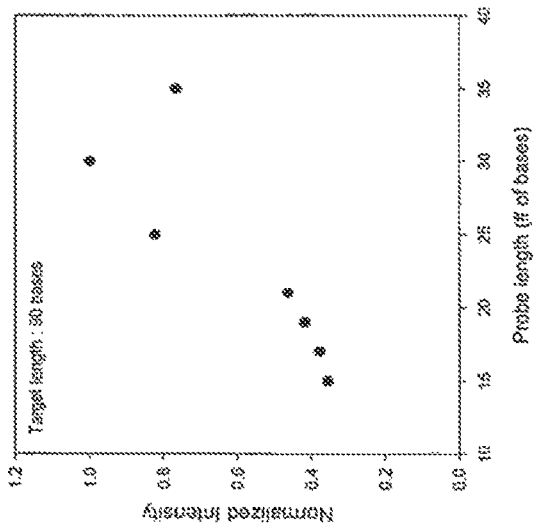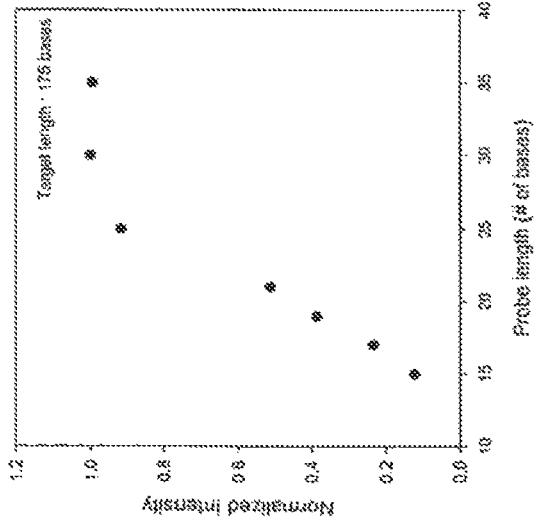

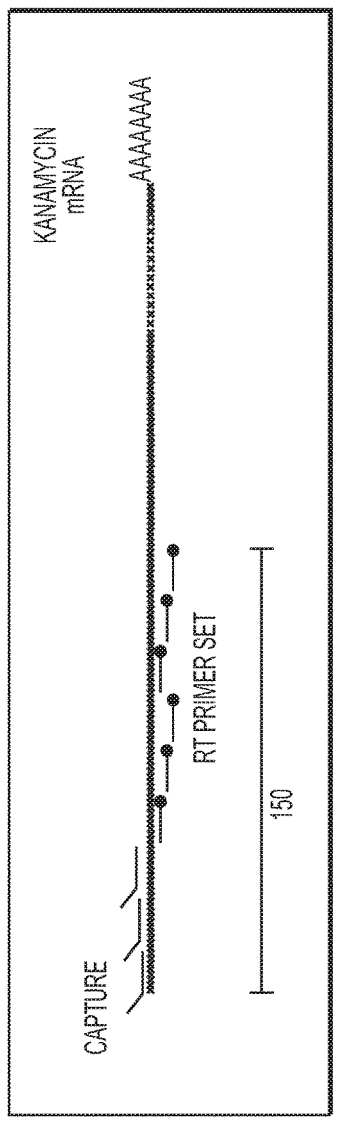
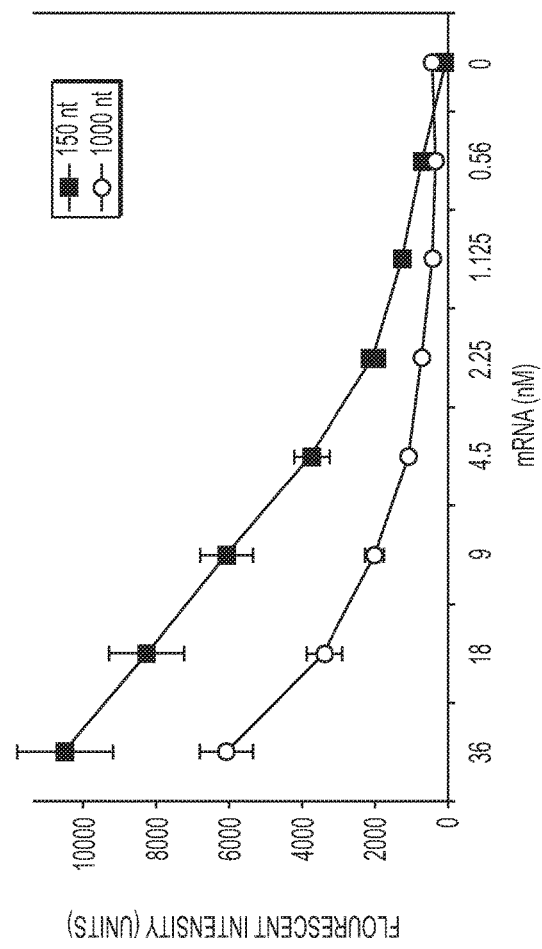

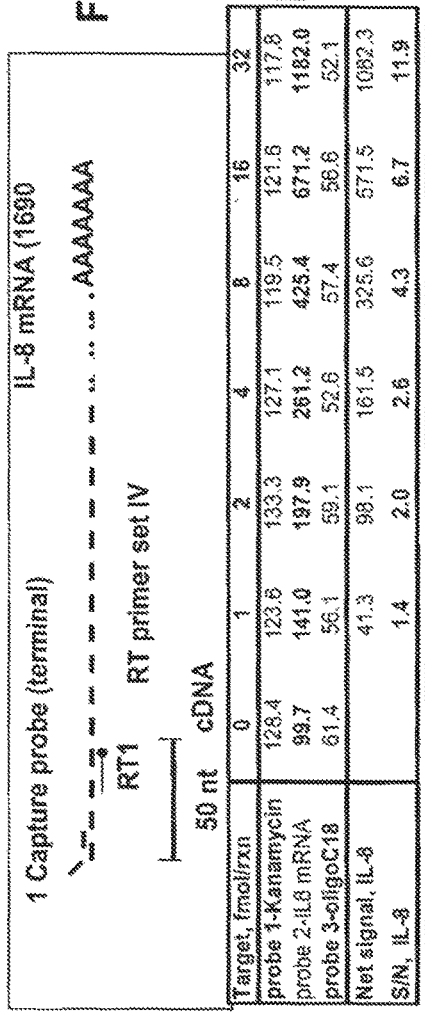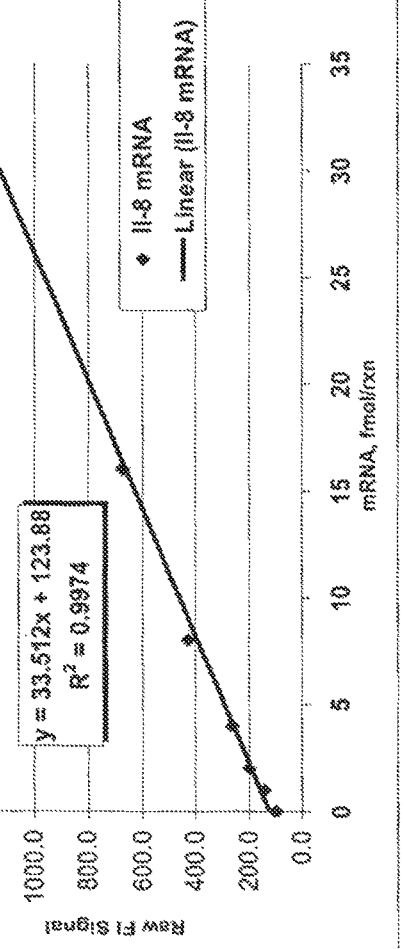
Fig. 19A
Fig. 19B
Fig. 19C

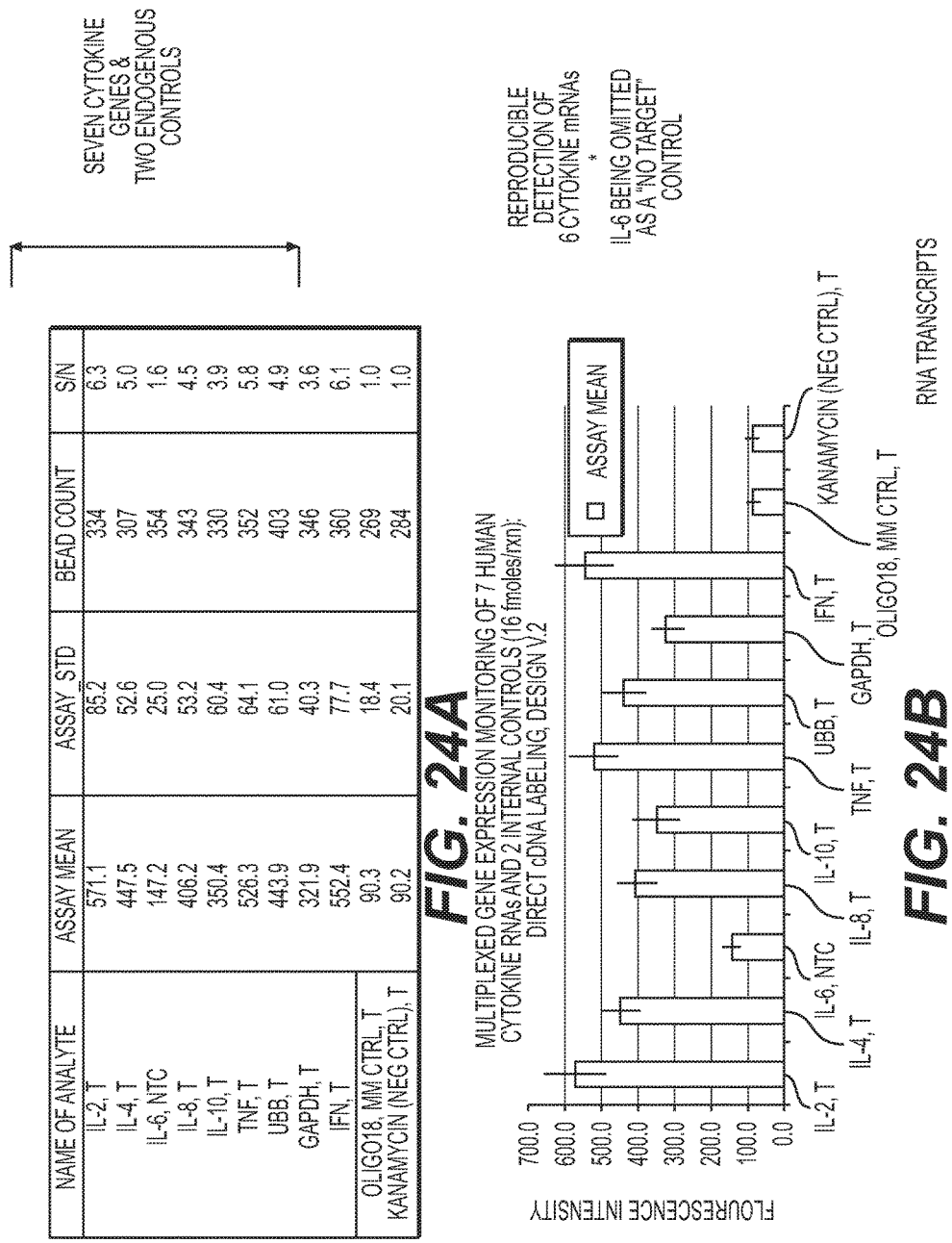

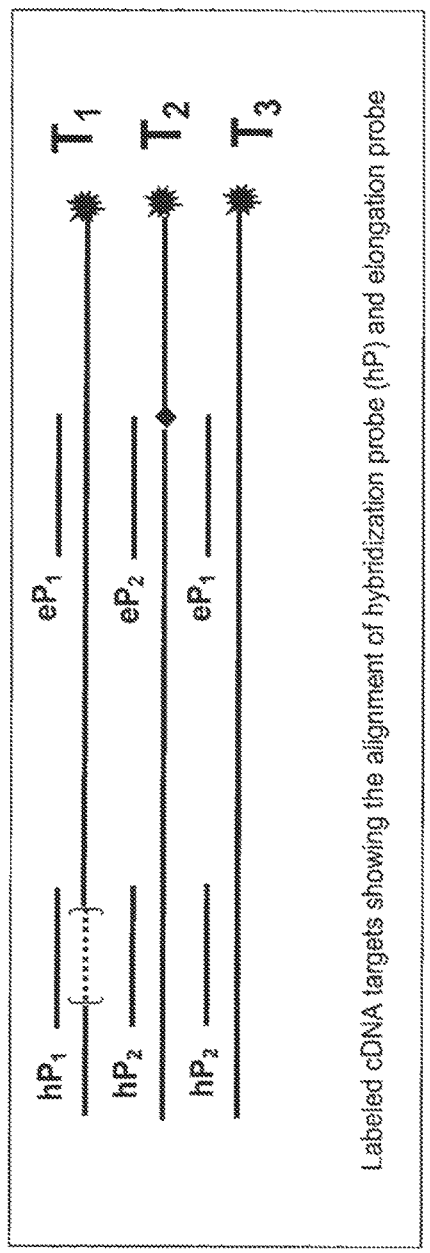
Fig. 25A
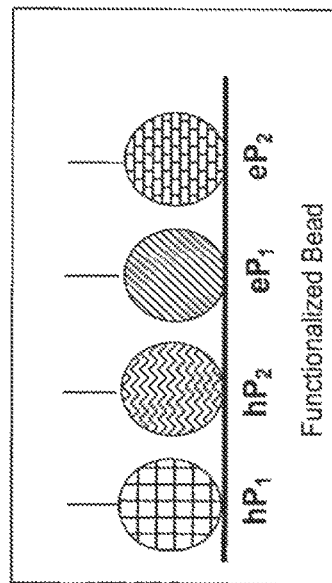
Fig. 25C
Fig. 25B

DESIGN OF CAPTURE/ELONGATION PROBES FOR 7 EXPRESSED GENES IN THE INBRED LINE BSSS53

```
05  ATAATATTTTGAGCATTCAGAAACACACCAAGCGAAGCACATTAGCAACAACCTAACAAC  (SEQ ID NO. 32)
22  ATAATATTTTGAGCATTCAGAAACACACCAAGCGAAGCCACTAGCAACAACCTAACAAC   (SEQ ID NO. 33)
16  ATAATACTTTGAGCATTCAGAAACACACCAAGCCAAGCGAAGCCACTAGCAACGACCAAACAAC (SEQ ID NO. 34)
31  ATAATATTTTGAGCATTCAGAAACACACCAAGCGAAGCGAAGCCACTAGCAACGACCAAACAAC (SEQ ID NO. 35)
12  ATAATATTTTGAGCATTCAGAAACACACCAAGCGAAGCGAAGCTTACTAGCAACGACTTAACAAC (SEQ ID NO. 36)
32  ATAATATTTTGAGCATTCAAAAACACACCAAGCGAAGCGAAGCTAGCAACGACTAACAAC  (SEQ ID NO. 37)
24  ATAATATTTTGAGCATTCAAAAACACACCAAGCGAAGCGAAGCGACTAGCAACGACTAACACC (SEQ ID NO. 38)
         ***  *** *****************         ******  ** **** *

05  AATGGCTACCAAGATATTATCCCCTCGCTTGCGCTTCTTGCGCTTCTTTGCGAGCGCAACAAA
22  AATGGCTACCAAGATATTATCCCCTCCTCGCTTGCGCTTCTTGCGCTTCTTTGCCGAGCGCAACAAA
16  AATGGCTACCAAGATATTAGCCCTCCTTGCGCTTCTTGCGCTTCTTTTGTGAGCGCAACAAA
31  AATGGCTACCAAGATATTAGCCCTCCTTGCGCTTCTTGCGCTTCTTTTGTGAGCGCAACAAA
12  AATGGCTACCAAGATATTAGCCCTCCTTGCGCTTCTTGCGCTTCTTTTGTGAGCGCAACAAA
32  AATGGCTACCAAGATATTAGCCCTCCTTGCGCTTCTTGCGCTTCTTTTGTGAGCGCAACAAA
24  AATGGCTACCAAGATATTAGCCCTCCTTGCGCTTCTTGCGCTTCTTTTAGTGAGCGCAACAAA
         ********************  *****  *  *************

05  TGCGTTCATTATTCCACAATGCTCACTTGCTCCAGTTCCATTATTACACAGTTCCTCCC
22  TGCGTCCATTATTCCACAATGCTCACTTGCTCACTTGCTCCTAGTTCCATTATTCCACAGTTCCTCCC
16  TGCGTTCATTATTCCACAATGCTCACTTGCTCACTTGCTCCTAGTGCCATTATTCCACAGTTCCTCCC
31  TGCGTTCATTATTCCACAATGCTCACTTGCTCACTTGCTCCTAGTGCCATTATTCCACAGTTCCTCCC
12  TGCGTTCATTATTCCACAATGCTCACTTGCTCACTTGCTCCTAGTGCCATTATTCCACAGTTCCTCCC
32  TGCGTTCATTATTCCACAATGCTCACTTGCTCACTTGCTCCTAGTGCCATTATACCACAGTTCCTCCC
24  TGCGTTCATTATTCCACAGTGCTCACTTGCTCACTTGCTCCTAGTGCCAGTATTCCACAGTTCCTCCC
         ****  ***  ***  *** ***  ************
```

FIG. 27

```
05  ACCAGTTACTTCAATGGGCTTCGAACACCCAGCTGTGCAAGCCTATAAGCTACAACAAGC
22  ACCAGTTACTTCAATGGCCTTCGAACACCCAGCTGTGCAAGCCTATAAGCTACAACAAGC
16  ACCAGTTACTTCAATGGGCTTCGAACACTCAGCTGTGCAAGCCTACAAGCTACAACAAGC
31  ACCAGTTACTTCAATGGGCTTCGAACACTCAGCTCTGCAAGCCTACAAGCTACAACAAGC
12  ACCAGTTACTTCAATGGGCTTCGAACACCTAGCTGTGCAAGCCTACAAGCTACAACAAGC
32  ACCAGTTACTTCAATGGGCTTCGAACACCTAGCTGTGCAAGCCTACAAGCCTACAACAAGC
24  ACCAGTTACTTCAATGGCTTCGAACATCCAGCCGTGCAAGCCTACAGGCTACAACTAGC
    ******************* *** ******** * * ********* * ********* ***

05  AATTGCGGCGAGCGTCTTACAACAACAATTTCCCAGTTGCAACAACAATCCTTGGCACA
22  GATTGCGGGCGAGCGTCTTACAACAACAACAATTGCCCAATTGCAACAACAATCCTTGGCACA
16  GCTTGCGGCGAGCGTCTTACAACAACAACAATTGCCCAATTGCAACAACAATCCTTGGCACA
31  GCTTGCGGCGAGCGTCTTACAACAACAACAATTGCCCAATTGCAACAACAATCCTTGGCACA
12  GCTTCGGGCGAGCGTCTTACAACAACAACAATTGCCCAATTGCAACAACAATCCTTGGCACA
32  GCTTACGGGCGAGCGTCTTACAACAACAATTGACCA------------
24  GCTTGCGGCGAGCGTCTTACAACAACAACCAATTGCCCAATTGCAACAACAATCCTTGGCACA
    ** ********* ******** *************        ** ***
```

FIG. 27 (cont.)

DESIGN OF CAPTURE/ELONGATION PROBES FOR 7 EXPRESSED GENES IN THE INBRED LINE BSSS53

```
05  ACCAGTTACTTCAATGGGCTTCGAACACCCAGCTGTGCAAGCCTATAGGCTACAACAAGC  (SEQ ID NO. 39)
22  ACCAGTTACTTCAATGGCCTTCGAACACCCAGCTGTGCAAGCCTATAGGCTACAACAAGC  (SEQ ID NO. 40)
16  ACCAGTTACTTCAATGGGCTTCGAACACTCAGCTGTGCAAGCCAACAGGCTACAACAAGC  (SEQ ID NO. 41)
31  ACCAGTTACTTCAATGGGCTTCGAACACTCAGCTCTGCAAGCCAACAGGCTACAACAAGC  (SEQ ID NO. 42)
12  ACCAGTTACTTCAATGGGCTTCGAACACTAGCTGTGCAAGCCAACAGGCTACAACAAGC   (SEQ ID NO. 43)
32  ACCAGTTACTTCAATGGGCTTCGAACACTAGCTGTGCAAGCCTACAGGCTACAACAAGC   (SEQ ID NO. 44)
24  ACCAGTTACTTCAATGGGCTTCGAACATCCAGCCGTGCAAGCCTACAGGCTACAACTAGC  (SEQ ID NO. 45)
    ****************** **********  ***  ********* * * *********
```

PHASING DESIGN FOR DETECTION OF GENES # 16 AND 31 :

STEP I:
BEAD 1 - eMAP WITH TAMRA: T VS. C (GENES 16 + 31 FROM ALL OTHERS)
BEAD 2 - eMAP: C VS. G (GENE # 31 ONLY)
STEP II: BEAD 1 WITH ELONGATED PROBE 16
DENATURE cDNA TARGET; HYBRIDIZE WITH A SHORT Cy5 SPECIFIC PROBE - C VS. G

*FIG. 28*

OPTIMIZATION OF GENE EXPRESSION ANALYSIS USING IMMOBILIZED CAPTURE PROBES

RELATED APPLICATIONS

This application is a divisional of U.S. application Ser. No. 14/257,294, filed Apr. 21, 2014, now U.S. Pat. No. 9,637,777 issued on May 2, 2017, which is a continuation of U.S. application Ser. No. 12/480,215, filed Jun. 8, 2009, now U.S. Pat. No. 8,795,960 issued on Aug. 5, 2014, which is a continuation of U.S. application Ser. No. 10/974,036 filed Oct. 26, 2004, now U.S. Pat. No. 7,563,569 issued on Jul. 21, 2009, which claims priority to U.S. Provisional Applications, No. 60/516,611, filed Oct. 28, 2003, and No. 60/544,533, filed Feb. 14, 2004, the contents of each application being incorporated by reference in its entirety.

GOVERNMENT INTEREST

Agencies of the United States government may have certain rights in this application, as certain work was performed under a DARPA contract.

BACKGROUND OF THE INVENTION

Gene Expression Analysis—

Fundamental biological processes such as cell cycle progression, cell differentiation and cell death are associated with variations in gene expression patterns which therefore provide a means of monitoring these processes on a molecular level. Gene expression patterns can be affected by exposure to therapeutic agents, and they are thus useful molecular indicators of efficacy of new drugs and validation of drug targets. At present, gene expression analysis plays an increasingly important role in connection with target discovery.

Gene expression analysis also offers a systematic molecular approach to the analysis of multigenic traits. In the context of plant molecular biology and molecular agriculture, expression patterns of designated genes and their temporal evolution are finding increasing application to guide "breeding" of desirable properties such as the rate of growth or ripening of fruits or vegetables.

Changes in expression levels also are indicators of the status and progression of pathogenesis. Thus, the underexpression of functional tumor suppressor genes and/or over-expression of oncogenes or protooncogenes is known to be associated with the presence and progression of various cancers. Specific genes have been identified whose expression patterns undergo characteristic variations in the early stages of immune response to inflammation or exposure to pathogenic agents including common viruses such as HSV or CMV as well as biochemical warfare agents such as anthrax. Contrary to the expression of protein markers such as antibodies, gene expression occurs at the earliest stages of immune response, thereby offering the possibility of early and specific therapeutic intervention.

Accordingly, the rapid quantitative analysis of expression levels of specific genes ("messages") and their evolution in time following exposure to infectious agents—or following treatment—holds significant promise as a tool to advance the molecular diagnosis of disease. However, as elaborated in the present invention, standard methods of quantitative gene expression analysis produce data of uncertain quality. Further, as a reliable and practical tool of molecular diagnostics, gene expression analysis, and specifically multiplexed expression monitoring (herein also referred to in abbreviation as "mEM"), must be simple in protocol, quick to complete, flexible in accommodating selected sets of genes, reliable in controlling cross-reactivity and ensuring specificity, capable of attaining requisite levels of sensitivity while performing quantitative determinations of message abundance over a dynamic range of three to four orders of magnitude and convenient to use.

These attributes generally do not apply to current methods. That is, while gene expression analysis has become a standard methodology of target discovery, its use as a diagnostic methodology, particularly in expression monitoring, requiring the quantitative determination of cDNA levels in the target mixture as a measure of the levels of expression of the corresponding mRNAs, has been limited by the lack of flexible and reliable assay designs ensuring rapid, reliable and quantitative multiplexed molecular diagnosis.

Spatially Encoded Arrays: In-Situ Synthesis and "Spotting"—

The practical utility of gene expression analysis is greatly enhanced when it is implemented using parallel assay formats that permit the concurrent ("multiplexed") analysis of multiple analytes in a single reaction. In a commonly practiced format (see, e.g., U. Maskos, E. M. Southern, *Nucleic Acids Res.* 20, 1679-1684 (1992); S. P. A. Fodor, et al., *Science* 251, 767-773 (1991)), the determination of gene expression levels is performed by providing an array of oligonucleotide capture probes—or, in some cases, cDNA molecules—disposed on a planar substrate, and contacting the array—under specific conditions permitting formation of probe-target complexes—with a solution containing nucleic acid samples of interest; these can include mRNAs extracted from a particular tissue, or cDNAs produced from the mRNAs by reverse transcription (RT). Following completion of the step of complex formation ("hybridization"), unbound target molecules are removed, and intensities are recorded from each position within the array, these intensities reflecting the amount of captured target. The intensity pattern is analyzed to obtain information regarding the abundance of mRNAs expressed in the sample. This "multiplexed" assay format is gaining increasing acceptance in the analysis of nucleic acids as well as proteins in molecular medicine and biomedical research.

Lack of Flexibility, Reproducibility and Reliability—

However, spatially encoded probe arrays generally are not well suited to quantitative expression analysis of designated sets of genes. Thus, in-situ photochemical oligonucleotide synthesis does not provide a flexible, open design format given the time and cost involved in customizing arrays. As a result, "spotted", or printed arrays, which provide flexibility in the selection of probes, have been preferred in applications requiring the use of only a limited gene set. However, "spotting" continues to face substantial technical challenges akin to those encountered by the standard "strip" assay format of clinical diagnostics, which generally is unsuitable for quantitative analysis. Poor reproducibility, relating to the non-uniformity of coverage, and uncertain configuration and accessibility of immobilized probes within individual spots, remains a significant concern. In addition, these arrays require expensive confocal laser scanning instrumentation to suppress substantial "background" intensities, and further require statistical analysis even at the early stages of subsequent data processing to account for non-uniform probe coverage and heterogeneity. Another concern is the comparatively large footprint of spotted arrays and the correspondingly large quantities of reagent consumed. Finally, scale-up of production to levels required for large-scale diagnostic use will be complex and economically unfavorable compared to batch processes such as those available for the preferred embodiment of the present invention in the form of planar arrays of encoded microparticles.

In addition to limited sensitivity, other problems with array-based diagnostics include limited ability to detect genes expressed in widely varying copy number (from 1 or 2 copies per cell to ~$10^4$ copies per cell). Thus, what is needed is an assay method which avoids these problems by maximizing detection sensitivity, minimizing cross-reactivity and permitting detection over a wide dynamic range of transcript copies.

Lack of Specificity—

The most prevalent methods of the prior art rely on multiplexed probe-target hybridization as the single step of quantitative determination of, and discrimination between multiple target sequences. Hybridization is sometimes lacking in specificity in a multiplexed format of analysis (see discussion in U.S. application Ser. No. 10/271,602, entitled: "Multiplexed Analysis of Polymorphic Loci by Concurrent Interrogation and Enzyme-Mediated Detection," filed Oct. 15, 2002). To enhance specificity, some formats of multiplexed hybridization employ long probes in spotted arrays, e.g. Agilent EP 1207209 discloses probes of preferred length 10 to 30, and preferably about 25. These may help to offset the random obstruction and limited accessibility of capture sequences in spotted probes. That is, probe-target complex formation in spotted arrays generally will not involve the full length, but rather randomly accessible subsequences of the probe. However, as disclosed herein, the use of long probes in a solid phase format generally will be counterproductive. Furthermore, the lack of specificity remains a source of concern: as shown herein, cross-hybridization generally will distort intensity patterns, thereby precluding quantitative analysis unless careful primer and probe designs are employed, using, for example the methods of a co-pending application (U.S. application Ser. No. 10/892,514, "Concurrent Optimization in Selection of Primer and Capture Probe Sets for Nucleic Acid Analysis," filed Jul. 15, 2004) and performing careful analysis taking into account the molecular interactions between non-cognate probes and targets.

Differential Gene Expression ("Transcript Profiling")—

Given these difficulties of standard methods of the art, and the potential for serious uncertainty and error in the quantitative determination of absolute expression levels, the format usually preferred in practice is differential expression analysis. This format characterizes differences in expression patterns between normal tissue or cells vs diseased or otherwise altered tissue or cells, or differences between normal ("wild-type") vs transgenic plants. In accordance with a commonly practiced approach, a set of cDNA clones is "spotted" onto a planar substrate to form the probe array which is then contacted with DNA from normal and altered sources. DNA from the two sources is differentially labeled to permit the recording of patterns formed by probe-target hybridization in two color channels and thus permitting the determination of expression ratios in normal and altered samples (see, e.g., U.S. Pat. No. 6,110,426 (Stanford University)). The system of two-color fluorescent detection is cumbersome, requiring careful calibration of the laser scanning instrumentation generally required to read spotted or other spatially encoded probe arrays—and as well as separate scans for each of the two color channels. These disadvantages are overcome by the subtractive method of differential gene expression disclosed herein which requires only a single detection color.

Complex Protocols—

In a commonly practiced approach to multiplexed expression profiling, mRNA molecules in a sample of interest are first reverse transcribed to produce corresponding cDNAs and are then placed in contact with an array of oligonucleotide capture probes formed by spotting or by in-situ synthesis. Lockhart et al. (U.S. Pat. No. 6,410,229) invoke a complex protocol to produce cRNA wherein mRNA is reverse transcribed to cDNA, which is in turn transcribed to cRNA under heavy labeling—of one in eight dNTPs on average—and detected on an array of synthesized oligonucleotide probes using a secondary "decoration" step. Such a laborious, error-prone and expensive process not only greatly increases the complexity of the method but greatly contributes to the uncertainty of final determinations of message abundance, for example by producing non-linear amplification.

A preferred method of the prior art for multiplexed expression analysis is the use either of randomly placed short reverse transcription (RT) primers to convert a set of RNAs into a heterogeneous population of cDNAs or the use of a universal RT primer directed against the polyA tail of the mRNA to produce full-length cDNAs. While these methods obviate the need for design of sequence-specific RT primers, both have significant disadvantages in quantitative expression monitoring.

Randomly placed RT primers will produce a representative population of cDNAs, that is, one in which each cDNA is represented with equal frequency, only in the limit of infinitely long mRNA molecules. The analysis of a designated set of short mRNAs by random priming generally will produce cDNAs of widely varying lengths for each type of mRNA in the mixture, and this in turn will introduce potentially significant bias in the quantitative determination of cDNA concentration, given that short cDNAs will more readily anneal to immobilized capture probes than will long cDNAs, as elaborated in the present invention. Further, the production of full-length cDNAs, if in fact full-length RT is successful, provides a large sequence space for potential cross-reactivity between probes and primers, making the results inherently difficult to interpret and hence unreliable.

The Role of Target and Probe Configurations—

DNA in solution has been shown to display the characteristics of polymers governed by chain entropy (see Larson et al., "Hydrodynamics of a DNA molecule in a flow field," Physical Review E 55:1794-97 (1997)). Especially single-stranded (ss) DNA is quite flexible, a fact which manifests itself in a short persistence length of the order of only a few nucleotides (nt) under most experimentally relevant conditions, considerably smaller than that of double stranded DNA (Marko J F, Siggia E D, "Fluctuations and supercoiling of DNA," 22:265, 506-508 (1994)). Capture of ssDNA to immobilized probes thus involves considerable restriction of the molecules' conformational freedom. At the same time if duplex formation is to occur, immobilized probes used in solid phase formats of nucleic acid analysis must accommodate invading target strands by elastic deformation. Conformational adjustments in target and probe molecules, considered as polymers, heretofore have not been appreciated in designing assays for nucleic acid analysis.

In view of the foregoing considerations, it will be desirable to have flexible, rapid, sensitive and specific methods, compositions and assay protocols particularly for diagnostic applications of gene expression analysis—herein also referred to as multiplexed expression monitoring (mEM). The present invention discloses such methods and compositions, specifically methods and compositions for rapid, customizable, multiplexed assay designs and protocols for multiplexed expression monitoring, preferably implemented in the format of random encoded array detection for multi-analyte molecular analysis. A co-pending application discloses methods by which to select optimized sets of desirable conversion probes (e.g. RT primers) and detection probes (e.g., probes for hybridization-mediated target capture) to further enhance the level of reliability (see U.S. application Ser. No. 10/892,514 "Concurrent Optimization in Selection of Primer and Capture Probe Sets for Nucleic Acid Analysis," filed Jul. 15, 2004).

SUMMARY OF THE INVENTION

Described herein are methods of multiplexed analysis of oligonucleotides in a sample, including: methods of probe and target "engineering", as well as methods of assay signal analysis relating to the modulation of the probe-target affinity constant, K by a variety of factors including the elastic properties of target strands and layers of immobilized ("grafted") probes; and assay methodologies relating to: the tuning of assay signal intensities including dynamic range compression and on-chip signal amplification; the combination of hybridization-mediated and elongation-mediated detection for the quantitative determination of abundance of messages displaying a high degree of sequence similarity, including, for example, the simultaneous determination of the relative expression levels, and identification of the specific class of, untranslated AU-rich subsequences located near the 3' terminus of mRNA; and a new method of subtractive differential gene expression analysis which, requires only a single color label.

Specifically, disclosed are methods, designs and compositions relating to:

(i) modulating the probe-target affinity constant, K, (and the corresponding "denaturing" temperatures for probes and targets) for optimizing the sensitivity of detection by exploiting entropic effects relating to probe layer elastic properties and target confinement, specifically:
  controlling target ("transcript") length and configuration;
  controlling the selection of capture subsequences within the transcript, i.e., the preferred placement of the capture subsequence in proximity to the transcript's 5' terminus;
  controlling concentration of target in solution;
  configuring of the grafted probe layer;
  controlling ionic strength and pH to confine duplex formation to the probe-target region, and to minimize target reannealing in solution;
(ii) systematically constructing optimal compositions of, and analyzing intensity patterns recorded from, assays probing multiplexed gene expression analysis;
(iii) implementing assay methodologies of
  tuning the dynamic range of assay signal intensity in order to accommodate a wide dynamic range of message abundance (from approximately 1 fmole per 10 µl of total reaction volume to 10,000 fmoles per 10 µl of total reaction volume), by way of:
    controlling probe density in conjunction with probe length and target interaction so as to control "packing" constraints affecting target capture;
    adjusting array composition, i.e., the numbers of binding sites;
    adjusting transcript length, transcript abundance and labeling density;

enhancing sensitivity by elongation-mediated sequence-specific signal amplification;
enhancing specificity by combining hybridization-mediated analysis and elongation-mediated analysis to detect highly homologous sequences;
performing differential expression analysis by a subtractive method requiring only a single color for detection of differences in the expression levels of specific genes in "altered" and "normal" samples;

For optimizing the specificity of detection, the sequence specificity in multiplexed reverse transcription and detection is optimized by appropriate selection of primers and corresponding probes, as described in co-pending U.S. application Ser. No. 10/892,514, filed Jul. 15, 2003, entitled "Concurrent Optimization in Selection of Primer and Capture Probe Sets for Nucleic Acid Analysis," incorporated by reference, and also referred to herein for convenience as "application Ser. No. 10/892,514."

Use of these methods of optimizing sensitivity and specificity permits the rapid, quantitative concurrent analysis of a designated set of genes by way of a reverse transcription of the given set of mRNAs to cDNAs and detection of these cDNAs by capture to a set of matching oligonucleotide probes, preferably on the basis of a simple protocol as disclosed herein, preferably obviating the need for a separate target amplification step, thereby simplifying the protocol and reducing the time to completion of the assay. The methods, protocols and designs described herein are particularly useful for a parallel format of multiplexed nucleic acid analysis, specifically quantitative analysis of expression patterns of a designated set of genes, the set of designated genes typically comprising between 2 and 100 different mRNAs ("messages"), and more typically between 10 and 30 messages, the process herein referred to as multiplexed expression monitoring (mEM). The methods, protocols and designs herein can be used advantageously in conjunction with the READ™ format of multiplexed expression monitoring, as described in U.S. application Ser. No. 10/204,799, filed Aug. 23, 2002, entitled: "Multianalyte molecular analysis using application-specific random particle arrays," hereby incorporated by reference.

The utility and advantages of the various methods, designs and compositions are set forth in detail below. A description of the drawings follows, which aid in understanding the inventions set forth herein.

BRIEF DESCRIPTION OF THE DRAWINGS

FIGS. 7A, 7B, 7C, show the probe length dependence of the degree of complex formation between targets of length, respectively, 175 nt, 90 nt and 25 nt probes and probes of various lengths as listed in Table I-1;

FIG. 8A shows a multiple primer-multiple probe (mpmp) design, illustrated for the case of producing a 150 nt cDNA;

FIG. 8B shows titration curves for a 150 nt cDNA and for a 1,000 nt cDNA produced by application of such mpmp designs from a 1,200 nt Kanamycin mRNA;

FIG. 19A shows the location of probe and primer in relation to the mRNA target;

FIG. 19B shows a table of a dilution series for a short cDNA obtained by reverse transcription of an IL-8 mRNA indicating a lower limit of detection of 1 fmole of mRNA;

FIG. 19C shows a curve plotted from the table of FIG. 19B.

FIG. 24A shows a table representing results from multiplexed expression analysis performed on a panel of seven cytokine and two "housekeeping" genes;

FIG. 24B shows a histogram showing the results in FIG. 24A;

FIG. 25A shows an illustration of locations of targets and probes in a design permitting discrimination of closely homologous sequences by application of a two-step process of polymorphism analysis;

FIG. 25B shows four encoded beads with different probes attached;

FIG. 25C shows the results of the assay with the probes in FIG. 25A and FIG. 25B;

FIG. 27 shows the sequence alignment of seven maize genes from the zein gene family (azs 22) of maize;

FIG. 28 shows a design combining hybridization and elongation permitting the detection of closely homologous sequences within the zein gene family (az2 22) of maize;

DETAILED DESCRIPTION

Figure 1:
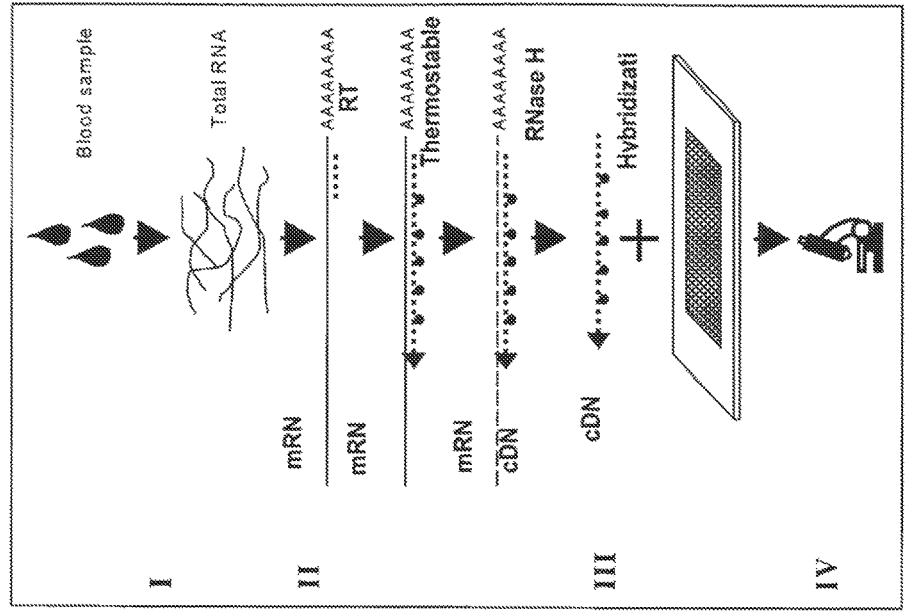
FIG. 1 shows the steps in the process of performing multiplexed expression monitoring.
Figure 2:
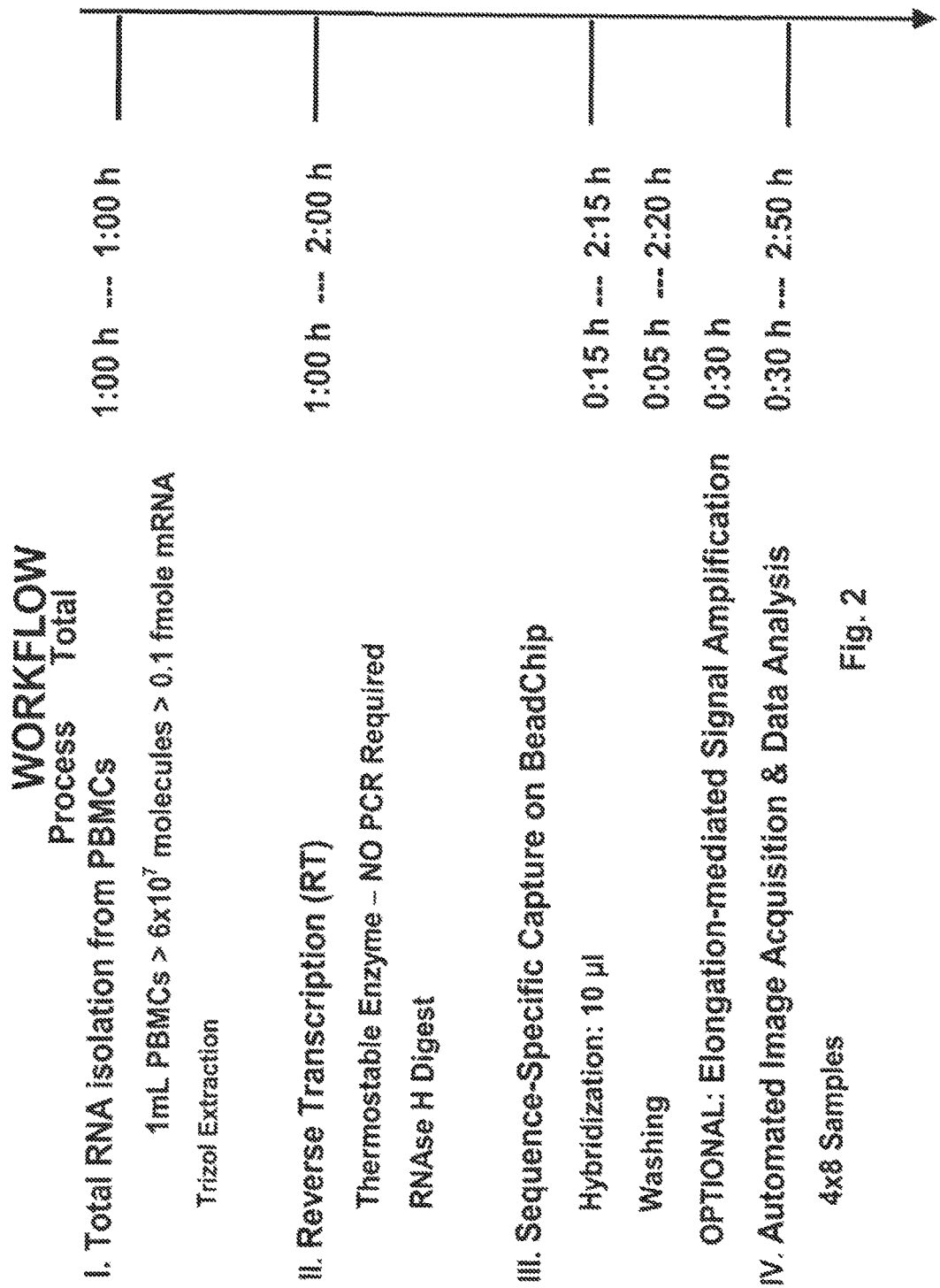
FIG. 2 shows a typical workflow relating to the process of FIG. 1.

Disclosed are methods, protocols and designs, including systematic procedures for enhancing the reliability of the process of determining levels of concentration ("abundance") of multiple nucleic acid analytes by capture to anchored oligonucleotide probes, specifically including the concurrent ("multiplexed") analysis of the expression levels of a designated set of genes. More specifically, disclosed are methods for the optimization of sensitivity, specificity and dynamic range of multiplexed gene expression analysis, and further, assay protocols including a subtractive format of performing differential expression analysis using only a single detection color. Also introduced is an explicit phenomenological description of the interaction of targets with anchored probes in order to evaluate the actual affinity constant governing this process. A preferred embodiment of forming planar arrays of capture probes displayed on color-encoded microparticles, without recourse to target amplification as in the case of a cytokine reference panel described herein, may permit completion of quantitative multiplexed expression monitoring in as little as three hours or less, from sample collection to data analysis (FIGS. 1 and 2). These methods and designs are herein illustrated by application to a variety of problems involving the capture of target nucleic acid strands to a layer of immobilized oligonucleotide probes.

I Optimizing Sensitivity and Dynamic Range: Modulation of Probe-Target Affinity

I.1 Sequence-Specific Affinity Governing Hybridization Complex ("Duplex") Formation—

The standard analysis of the hybridization-mediated formation of a complex ("annealing") of two oligonucleotides invokes the law of mass action to relate the concentration of complexed ("bound") probes and targets, c=[TP], to the concentration of uncomplexed ("unbound", "free") probes, herein preferably displayed on encoded beads, p=[P], and the concentration of uncomplexed targets, t=[T], as follows:

$$[TP]=K[T][P]$$

or $$c=Kpt$$

In analogy to the common practice of computing "melting temperatures", the (sequence-dependent) affinity constant is computed using a phenomenological "nearest-neighbor" (NN) model to represent the interaction between adjacent base pairs formed within the probe-target complex for given experimental conditions including salt concentration and temperature. The free energy of duplex formation, also referred to herein as "binding energy" or "condensation energy", is computed in the form:

$$\Delta G_C = \Delta G_{Nucleation} + \Sigma_{i \in NN\text{-}Pairs}\{\Delta H_i + T\Delta S_i\}$$

where $\Delta H_i$ and $\Delta S_i$ represent enthalpy and entropy, respectively. The condition $\Delta G_C=0$ defines the "melting temperature", $T_M$, widely used in the field to estimate the stability of a duplex.

In accordance with standard thermodynamics, the (sequence-specific) affinity constant, $K_{SS}$, is computed from the expression $$K_{SS}=K_0 \exp(-\Delta G_C/kT)$$

wherein $K_0$ represents a constant and k denotes the Boltzmann constant.

Given an affinity constant, and given initial concentrations of probe, $[P]_0$, and target, $[T]_0$, the equilibrium concentration of probe-target complex, [TP], is obtained as a function of initial target concentration $[T]_0$.

Using this standard model, melting temperatures and affinity constants were calculated for complexes formed by a 175 nt DNA target and seven different DNA oligonucleotide probes varying in length from 15 nt to 35 nt at a temperature of 55° C. and a salt concentrations of 2M. Target and probe sequences are shown below in Table I-1.

TABLE I-1

| Seq ID | Sequence |
|---|---|
| Target 175-mer SEQ ID NO. 1 | AG GGT AAA ATT AAG CAC AGT GGA AGA ATT TCA TTC TGT TCT CAG TTT TCC TGG ATT ATG CCT GGC ACC ATT AAA GAA AAT ATC ATC TTT GGT GTT TCC TAT GAT GAA TAT AGA AGC GTC ATC ATC AAA GCA TGC CAA CTA GAA GAG GTA AGA AAC TAT GTG AAA ACT TTT TG |
| Target 90-mer SEQ ID NO. 2 | T CAG TTT TCC TGG ATT ATG CCT GGC ACC ATT AAA GAA AAT ATC ATC TTT GGT GTT TCC TAT GAT GAA TAT AGA AGC GTC ATC ATC AA |
| Target 40-mer SEQ ID NO. 3 | C ACC ATT AAA GAA AAT ATC ATC TTT GGT GTT TCC TAT GAT |
| Target 25-mer SEQ ID NO. 4 | GAA AAT ATC ATC TTT GGT GTT TCC T |
| Probe 15-mer SEQ ID NO. 5 | CTT TTA TAG TAG AAA |
| Probe 17-mer SEQ ID NO. 6 | CTT TTA TAG TAG AAA CC |
| Probe 19-mer SEQ ID NO. 7 | CTT TTA TAG TAG AAA CCA C |
| Probe 21-mer SEQ ID NO. 8 | CTT TTA TAG TAG AAA CCA CAA |
| Probe 25-mer SEQ ID NO. 9 | CTT TTA TAG TAG AAA CCA CAA AGG A |
| Probe 30-mer SEQ ID NO. 10 | CTT TTA TAG TAG AAA CCA CAA AGG ATA CTA |
| Probe 35-mer SEQ ID NO.11 | CTT TTA TAG TAG AAA CCA CAA AGG ATA CTA CTT AT |

Calculated melting temperatures and affinity constants are summarized in Table I-2. The very high affinity constants predicted for the longer probes would imply a favorable sensitivity for detection of target. For example, using planar arrays of color-encoded microparticles ("beads") of 3.2 μm diameter to display probes in accordance with the Random Encoded Array Detection format of multianalyte molecular analysis, and setting the number of probes per bead to $[P]_0=10^5$, the law of mass action provides the following estimate for the lower limit of target detection with the 21-mer probe:

$$[T]_{min}=[PT]_{min}/K[P]_0=[PT]_{min}/1.7\times10^{10}/M\times10^5;$$

here, $[PT]_{min}$ represents the minimum number of probe-target complexes per bead required to ensure detection, and with $[PT]_{min}=10^3$, $[T]_{min} \cong 0.6\times10^{-12}$ pM, a value corresponding to a message abundance of single copies per cell.

TABLE I-2

| Probe Length | Melting Temperature, °C | Affinity Constant (/M) |
|---|---|---|
| 15 | 48.4 | $5.382 \times 10^5$ |
| 17 | 56.1 | $3.536 \times 10^7$ |
| 19 | 61.3 | $1.129 \times 10^9$ |
| 21 | 64.9 | $1.712 \times 10^{10}$ |
| 25 | 71.1 | $1.116 \times 10^{13}$ |
| 30 | 74.0 | $2.717 \times 10^{15}$ |
| 35 | 76.2 | $7.823 \times 10^{17}$ |

I.2 the Role of Target and Probe Configurations: Implications for Assay Design

As described below, the size and configuration of the target as well as the size, configuration and arrangement of substrate-anchored probes have a substantial effect on probe-target interaction which leads to substantial deviations of actual probe-target affinities from those predicted by the NN model.

The adverse role of steric effects ("hindrance") in the capture of target analytes to immobilized probes, and specifically the importance of probe accessibility, have been known in the art; see e.g., Guisan, J. M. in "Immobilization of Enzymes and Cells," Gordon F. Bickerstaff, Humana Press, Totowa, N.J., pp. 261-275 (1997). Thus, empirical strategies of enhancing capture efficiency by introducing spacers of preferred length in order to alleviate constraints related to probe "packing" have been described; see e.g., Southern E. et al., Nat. Genet. (suppl.) 21, 5-9 (1999). However, in contrast to the known methods, the methods disclosed herein establish the fundamental interconnection between certain properties of target and probe layer as the foundation of a systematic design process guiding the optimization of probe-target interaction. Probe layer compressibility is identified as a property to be maximized in order to facilitate penetration of the target, or portions of the target, into the layer in the course of duplex formation. More generally, the design criteria herein reflect the nature and magnitude of effects of length, grafting density and electrostatic charge of substrate-anchored probes, length and configuration of target, and selection of the location of the capture subsequence relative to the target's 5' terminus on capture efficiency and hence assay signal. Conversely, to permit the correct determination of target abundances, methods are disclosed to determine the re-normalized constants governing probe-target interaction.

Disclosed are methods, designs and design rules relating to the selection of sizes, configurations and arrangements of anchored capture probes, sizes and configurations of target including the selection of capture subsequences and the selection of array compositions and protocols, in order to modulate probe-target capture efficiencies and to optimize assay sensitivity, specificity and dynamic range.

In order to establish design criteria, the nature and magnitude of effects of length, grafting density and charge of substrate-anchored probes as well as size and configuration of target, or designated subsequences of target, on capture efficiency and hence assay signal, are disclosed. Relevant experiments were performed in accordance with the Random Encoded Array Detection (READ™) format of multi-analyte molecular analysis in which probes are displayed on color-coded polymer microparticles ("beads"), and beads are arranged in a planar array on a silicon chip. See U.S. application Ser. No. 10/204,799, filed Aug. 23, 2002, entitled: "Multianalyte molecular analysis using application-specific random particle arrays," hereby incorporated by reference. Probes preferably are "end-grafted" to beads by way of a covalent linkage at the 5' terminus. The analysis of experiments performed on synthetic model DNA targets as well as model cDNAs generated by reverse transcription from a 1,200 nt Kanamycin mRNA (Promega), establishes a critical role of target and probe configurations in the interaction of targets with an immobilized set of probes, even when the target strands of interest are of such relatively modest size.

I.2.1 Synthetic Model Targets—

Binding isotherms were recorded over a wide range of concentration of labeled synthetic DNA targets varying from 25 nt to 175 nt in length, and over a range of capture probe lengths varying from 15 nt to 35 nt (see Table I-1 and Example I).

Target Length Dependence—

Figures 3A, 3B:
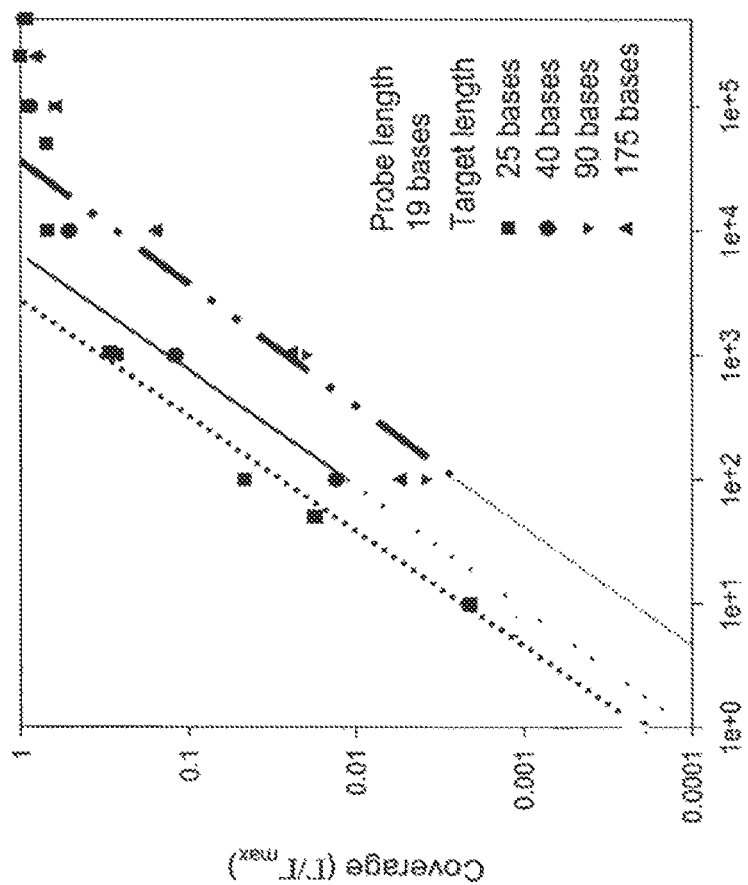
FIG. 3A shows titration ("binding") curves for model probes and targets listed in Table I-1.
FIG. 3B shows the affinity constants ("K") and number of probe sites ($P_o$) per microparticle for the curves in FIG. 3A extracted from the regression analysis of the curves in terms of the law of mass action.

To investigate the dependence of probe-target capture efficiency on the length of the target strand, four fluorescently end-labeled synthetic DNA targets, 25 nt, 40 nt, 90 nt and 175 nt in length (see Table I-1), all containing a common subsequence, were permitted to hybridize to a 19 nt capture probe displayed on color-coded beads of 3.2 μm diameter and arranged in a planar array in accordance with the READ format. Representative binding curves, reveal a significant dependence on target length, L. As illustrated in FIG. 3A, the longer the target, the lower the signal intensity attained at any given target concentration below saturation; here, the intensity is normalized, for each curve, to that attained at saturation.

Estimates of the experimental affinity constants, K*, and the number densities of available capture probes, $[P]_0 = p_0$, were obtained by fitting each profile to the law of mass action; results are summarized in FIG. 3B. To compute affinities, the signal intensity, I, is herein taken to be proportional to the product of the number of captured targets per bead, c, and the number of fluorophores per target, $n_F$, that is, $I \sim n_F c$; interconversion between I and c is facilitated by reference to a calibration curve, described in Example II in conjunction with Table I-3 and FIG. 4. Typical observed affinity constants are of the order of $K^* = 10^8/M$ where target length is about equal to probe length, an order of magnitude lower than those predicted by the NN model (Table I-2). Typical values of $p_0$, the number of occupied sites at saturation, are of the order of $10^5$ per bead.

Under typical experimental conditions of interest in the context of gene expression analysis, the size of the target will exceed that of the probe, and each captured target will thus occlude more than a single probe; accordingly, saturation will reflect the capture of a limiting number, $N_T^{Sat}$, of targets to a bead of finite area, $A_0$. A lower limit of $N_T^{Sat}$ is obtained by assuming that the bead surface is decorated with captured targets assuming a "relaxed" configuration in which a target's characteristic size is set by its radius of gyration, $R_{G,T} \sim a L^\nu$, $\nu$ denoting a characteristic exponent with numerical value $\nu = \frac{1}{2}$ for an ideal chain and $\nu = \frac{3}{5}$ for a self-excluding chain in a good solvent in 3 dimensions (deGennes, "Scaling Concepts in Polymer Physics", Cornell University Press, 1979). Accordingly, for the smallest target, $N_T^{Sat} \sim A_0/R_{G,T}^2$, or $N_T^{Sat} \sim 1/L$. Identifying $p_0$ with the number, $N_T^{Sat}$, of targets captured per bead at saturation yields, for example for the smallest target (L=25 nt), an average molecular area of $A_T \sim 4\pi(1.6 \, \mu m)^2/8*10^5 \sim 4*10^3 \, Å^2$, a value comparable to that obtained for $A_T^{Relaxed} \sim \pi R_{G,T}^2 \sim 6.5*10^3 \, Å^2$ when using an (experimental) estimate of $R_{G,T} \cong 9 L^{1/2} \cong 45 \, Å$ (Tinland et al, Macromolecules 30, 5763 (1997)). For the 175 nt target, comparison of the corresponding two values yields $A_T \cong 1.6*10^4 \, Å^2 < A_T^{Relaxed} \cong 4.5*10^4 \, Å^2$. These comparisons suggest that, at saturation, either the larger target molecules are not in their relaxed, but in a more compact configuration, or that they are no longer isolated but are substantially "overlapping," that is, interpenetrating.

Figure 5:
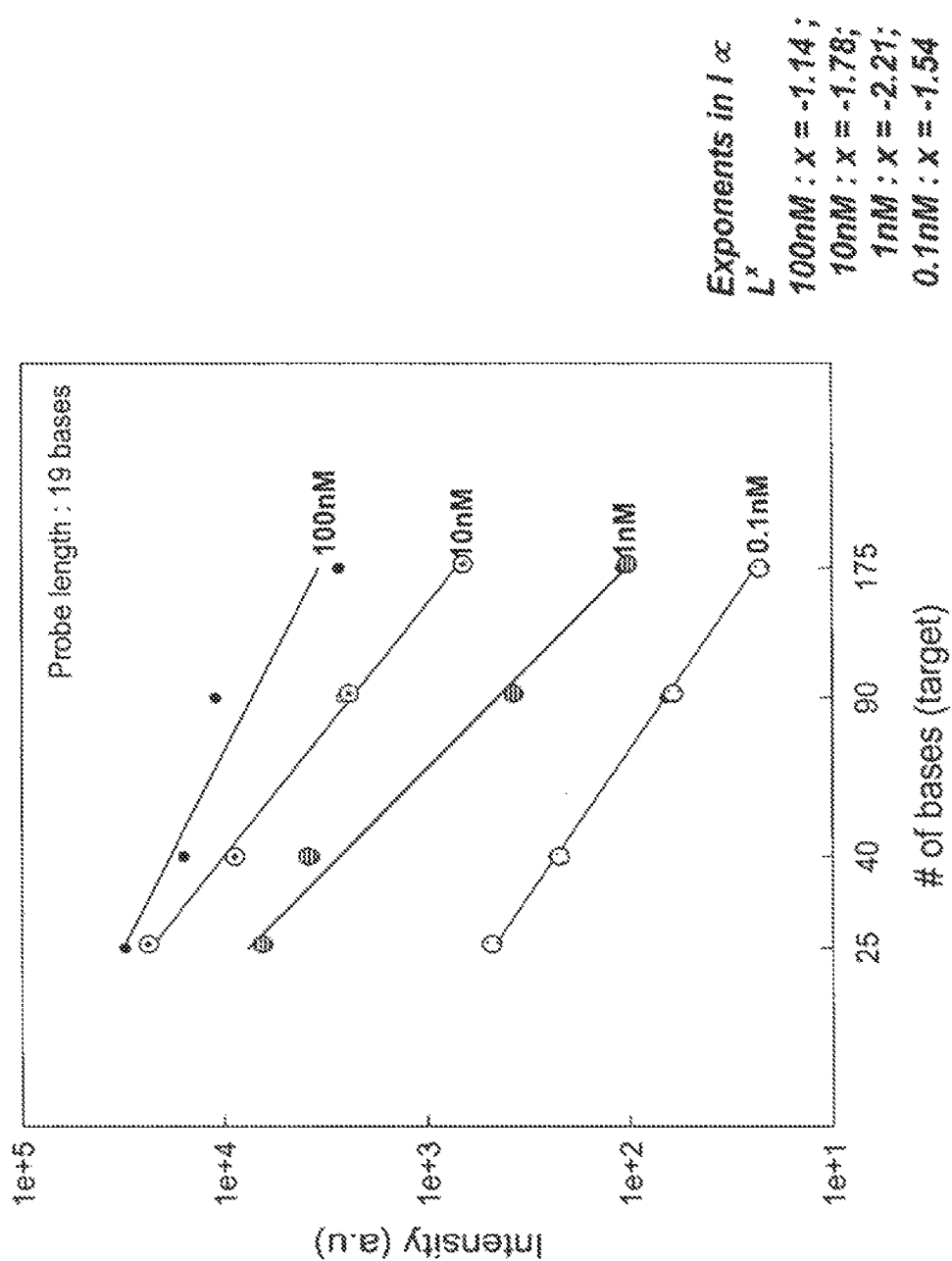
FIG. 5 shows the target length dependence of the degree of complex formation between probes and targets listed in Table I-1 along with exponents extracted from the regression analysis of the data in terms of a power law.

When plotted at a fixed target concentration as a function of target length, L, the signal intensity displays a $1/L^x$ dependence (FIG. 5), with $3/2 \leq x \leq 2$, as target length is varied from L=25 nt to L=175 nt, and target concentration, at each length, is varied over three orders of magnitude from 0.1 nM to 100 nM. Notwithstanding the fact that all targets hybridize to the 19 nt probe via the same 19 nt subsequence (Table I-1), implying identical "condensation" energies of duplex formation, the increase in target length is seen to result in a substantial reduction in signal intensity. Thus, for given length of capture probe, the longer the target, the less favorable the formation of the duplex and the lower the effective affinity.

The power-law dependence of the effective affinity governing probe-target hybridization provides a means of tuning the capture efficiency in accordance with the length of specific target strands. This is a particularly useful design criterion in applications such as expression monitoring permitting the control of cDNA lengths by placement of sequence-specific reverse transcription (RT) primers. As discussed herein in greater detail, rare messages preferably are converted to short cDNAs to maximize capture efficiency.

Probe Length Dependence—

Figures 6A, 6B:
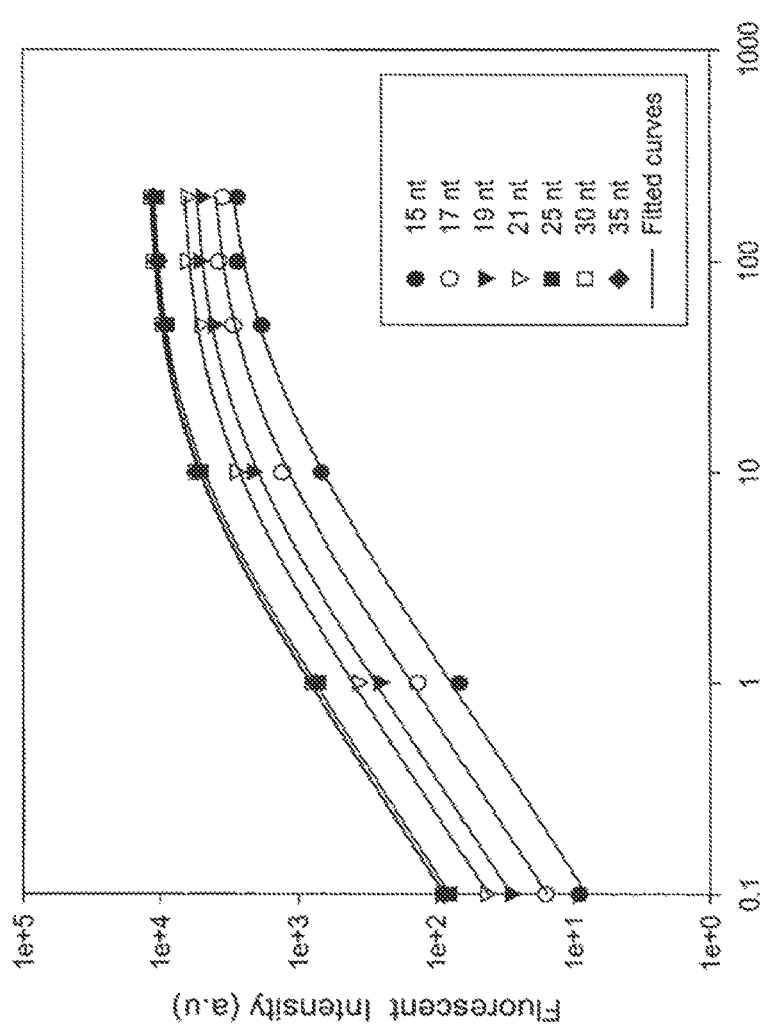
FIG. 6A shows adsorption isotherms relating to complex formation between the 175 nt model target listed in Table I-1 and probes of various lengths.
FIG. 6B shows the affinity constants ("K") and number of probe sites ($P_o$) per microparticle for the curves in FIG. 6A extracted from the regression analysis of the curves in terms of the law of mass action.

A complete set of binding curves such as those shown for the 19 nt probe in FIG. 3 was generated using a set of capture probes varying in length from 15 nt to 35 nt. The binding curves for the 175 nt target are shown in FIGS. 6A, 6B along with fits to the law of mass action, assuming, as stated above, $I \sim n_F c$, $n_F$ representing the (average) number of fluorescent labels per molecule. For this set, fits yield values of the affinity constant of the order of $K^* \cong 5*10^7/M$, approximately a factor of 20 lower than those predicted by the NN model (see Table I-2). The dependence of signal intensity, at a fixed concentration of targets of length 25 nt, 90 nt and 175 nt, is shown as a function of increasing probe length in FIGS. 7A to 7C. The intensity profiles for short probe lengths display the expected increase, although smaller than that predicted by the NN model; however, for all four target lengths, the profiles peak or level off at a probe length of approximately 30 nt. This is entirely unexpected from the point of view of the NN model. Instead, as discussed herein below, these results suggest that the capture of target to immobilized probes requires elastic deformation of not only the incoming target strands but also of the layer of capture probes.

I.2.2 Kanamycin mRNA: Selection of Transcript Length and Placement of Capture Sequence It is further shown that, as with synthetic targets, the reduction in length, L, of cDNAs, herein also referred to as "transcripts," obtained by reverse transcription, produces a systematic and significant enhancement in the assay signal of the shorter transcript over that attained from the longer transcript given the same mRNA concentration. As illustrated herein for a 1,200 nt Kanamycin mRNA (Promega), cDNA products varying in length from ~1,000 nt to ~50 nt were produced by selecting suitable RT primers (Example III). Placement of the capture subsequence near the 5' end of the cDNA is shown to produce an additional enhancement. Accordingly, capture probes preferably were designed to match subsequences located in close proximity to the transcript's 5' end (see FIG. 8A). Both enhancements reflect the importance of configurational contributions to the free energy governing the interaction of targets with anchored probes. As a result of these effects, the sequence-dependent affinity, $K_{SS}$, is reduced to an effective affinity, $K^*(L) < K_{SS}$, with significant implications for the design of anchored capture probes as well as transcripts, particularly when the fraction of available substrate surface covered by adsorbed target exceeds a characteristic value, $\gamma^* = c^*/c_{max}$.

Multiple Primer Multiple Probe (mpmp)-RT Protocol—

Figure 9:
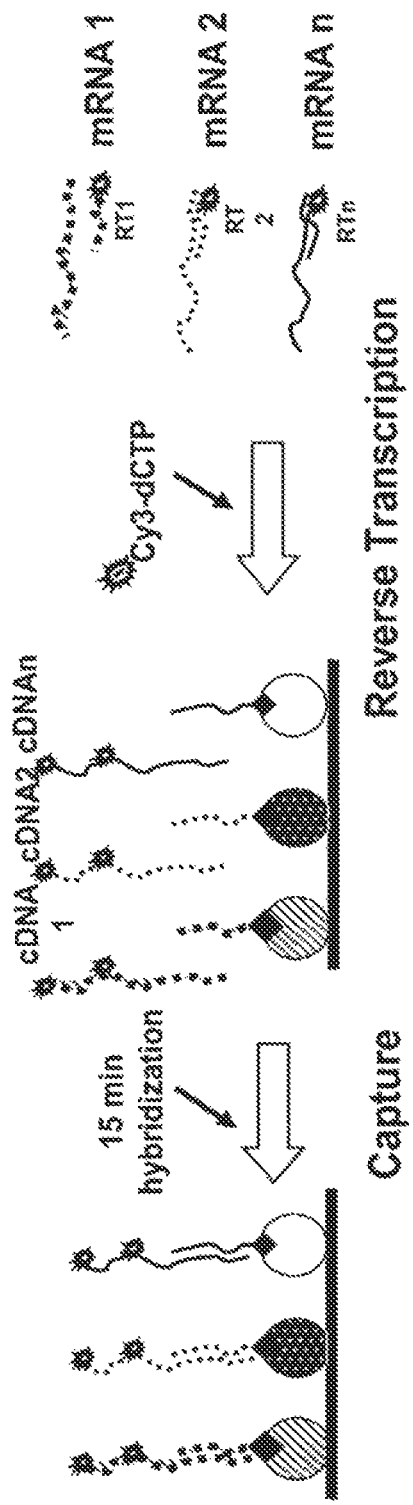
FIG. 9 shows a schematic illustration of the steps involved in hybridization-mediated expression monitoring in accordance with Random Encoded Array Detection (READ™)

In some cases, multiple reverse transcription (RT) primers were employed (FIG. 8A) so as to allow for the possibility of producing multiple cDNA transcripts from a single mRNA template by way of displacing a shorter cDNA incorporating a first RT primer placed in close proximity to the mRNA's 3' end, by a longer cDNA transcript incorporating a second RT primer placed farther from the mRNA's 3'end. For each cDNA, one or more capture probes—here of length 19 nt—were provided (Example IV). An embodiment for multiplexed expression monitoring invokes the READ format, for example in the version illustrated in FIG. 9.

I.2.2A Effect of Reduction in Transcript Length—

Guided by the results of titrations on model compounds, as described in Sect. I.2.1, it was established that a reduction in transcript length does indeed yield a substantial improvement in assay signal.

A series of RT reactions, performed on Kanamycin mRNA over a range of initial concentrations in accordance with an mpmp-RT design and assay protocol (Example IV), produced the titration curves shown in FIG. 8B. At each mRNA concentration, ranging from 36 nM to 560 pM, the signal recorded for the 150 nt transcript exceeds that recorded for the 1,000 nt transcript, notwithstanding the fact that the number, $n_F$, of fluorophores for the 1000 nt transcript exceeds that for the 150 nt transcript.

Figure 10:
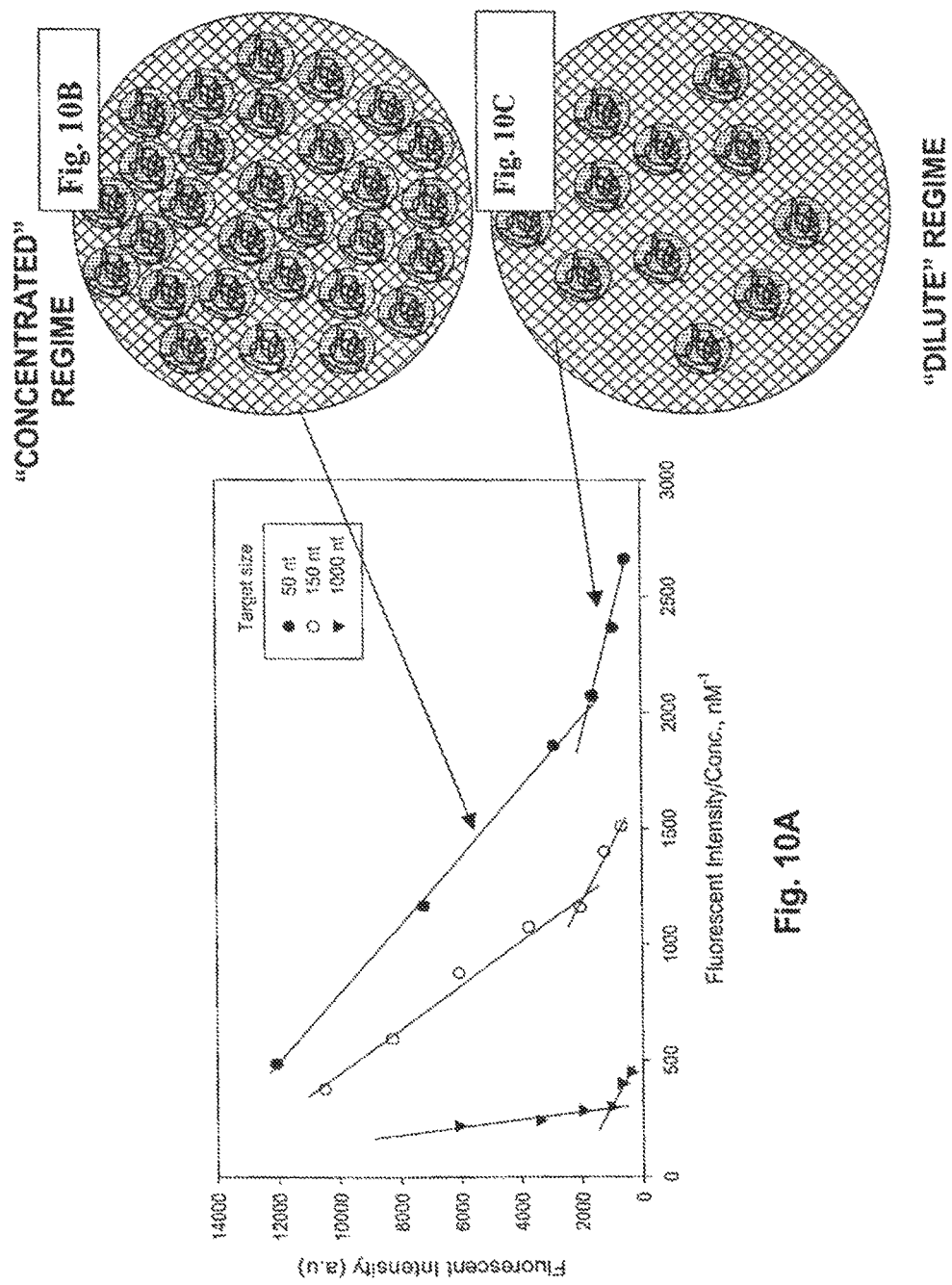
FIG. 10A shows linearized titration curves ("isotherms") obtained by transformation of the titration curves shown in FIG. 8 for cDNAs of three different lengths, each produced by reverse transcription from Kanamycin mRNA; "breaks" in the isotherms indicate the existence of a "dilute" and a "concentrated" regime of adsorption.
FIG. 10B shows a schematic illustration of the "footprint" of target strands captured to immobilized probes in the concentrated regime.
FIG. 10C shows a schematic illustration of the "footprint" of target strands captured to immobilized probes in the dilute regime.

For example, $I_{150\ nt}/I_{1000\ nt} \sim 3$, at the target concentration corresponding to 1.13 nM. The experimental observation of an enhancement of ~3, for example near the cross-over concentration (see "break points" indicated in FIG. 10A) is in accordance with the enhancement anticipated from the reduction in transcript length, L. That is, the expected enhancement arising from the reduction in L from 1,000 nt to 150 nt would be given by ~$(1000/150)^x(3/15)$, the first factor relating to length reduction, as discussed in Sect. I.2.1 for the model targets (with $3/2 \leq x \leq 2$), and the second factor reflecting the fact that the 150-mer, at the chosen linear labeling densities, $n_{F\ (150\ nt)} \sim 3$ and $n_{F(100\ nt)} \sim 15$. Setting $x=3/2$, this estimate yields an enhancement of ~3.5, comparable to the experimental observation.

Similarly, a reduction of transcript length from 1,000 nt to 50 nt results in an enhancement of ~$(1000/50)^{3/2}(1/15) \sim 6$, the first factor relating to length reduction (with $x=3/2$) and the second factor reflecting the fact that the 50-mer, at the chosen labeling densities, would contain, on average, only a single label.

Linearized Adsorption Isotherm Representation—

Further insight is gained by representing the titration curves in the form of a linearized adsorption isotherm representation which directly follows from the law of mass action. For the reaction P (probe)+T (target)<->C (probe-target complex), mass action implies the relation c=Kpt, where c, p and t denote the respective concentrations and K denotes the affinity constant. Setting $p=c-p_0$, $t=c-t_0$, where $p_0$ and $t_0$ respectively represent initial probe and target concentrations, yields $c=K(c-p_0)(c-t_0)$ and, provided that $c \ll t_0$, as in the experiments reported here, $c=K(p_0-c)t_0$ or $c=p_0-c/K\ t_0$. Displaying titration results in the latter form—assuming, as before, that the signal, I, is proportional to c, $I \sim n_F c$, $n_F$ denoting the number of fluorophores per transcript—highlights the linear dependence of c on $(c/Kt_0)$ and permits the determination of $p_0$, from the intercept, and K, from the slope. Specifically, abrupt changes in slope signal a cross-over between regimes, as discussed in the text.

FIG. 10A displays the titration results for the 1,000 nt and 150 nt transcripts in this format, along with an isotherm obtained in the same manner for a 50 nt transcript. All three plots indicate a cross-over from a "dilute" regime characterized by a shallower slope and hence a higher affinity constant, to a "concentrated" regime of steeper slope and hence lower affinity constant. Slopes in the dilute regime are comparable for all three transcripts, indicating similar values for the corresponding affinity constants. In contrast, slopes, and hence effective affinity constants, in the concentrated regime are seen to be transcript-length dependent (see Table I-4).

As summarized in Table I-4, at the cross-over—observed for all transcripts at a

TABLE I-4

| cDNA Length (nt) | $K [M^{-1}]$ (Dilute regime) | $K [M^{-1}]$ (Concentrated regime) | Crossover Conc. [nM] | Fractional Coverage at Crossover [θ] |
|---|---|---|---|---|
| 1000 | $2 \times 10^8$ | $1 \times 10^7$ | ~1 | 0.2 |
| 150 | $2 \times 10^8$ | $1 \times 10^8$ | ~1 | 0.2 |
| 50 | $5 \times 10^8$ | $2 \times 10^8$ | ~1 | 0.5 | concentration of approximately $t_0 \cong 1$ nM—the affinity constant for the 1,000 nt transcript drops by a factor of ~20, and that for the 150 nt and 50 nt transcripts by a factor of ~2. That is, the reduction in the effective affinity is increasingly less pronounced as transcript length decreases. In the dilute regime, the slope for adsorption isotherm of the 50 nt transcript displays a slope that is smaller by a factor of ~2.5 than that for the isotherm of the 150 nt transcript, indicating a correspondingly higher value for the corresponding affinity constant of the former.

The cross-over to this regime occurs at low values of coverage, θ, as may be seen from the following argument. Transformation of the linearized adsorption isotherm representation to the standard form of the Langmuir isotherm, $1/\{1+1/K\, t_0\}=c/p_0$, displays the fraction of occupied probes, $c/p_0=\theta$; as discussed below, is more precisely viewed as the ratio of the number of probes occupied at $t_0$ relative to the number occupied at saturation. Specifically, extrapolating from the concentrated regime into the cross-over regime shows that, for the examples in FIG. 10A, $K\, t_0 \ll 1$ and hence $1/K\, t_0=p_0/c$. Using the estimates obtained above for the effective affinity constants in the concentrated regime, the estimated fraction of occupied sites, $\theta^*=c^*/p_0$, at the cross-over is ~0.2 for the 150 nt and the 1,000 nt transcripts. That is, the larger transcripts start to interact at a fractional occupancy of available bead-displayed probes of 20%.

Figure 11:
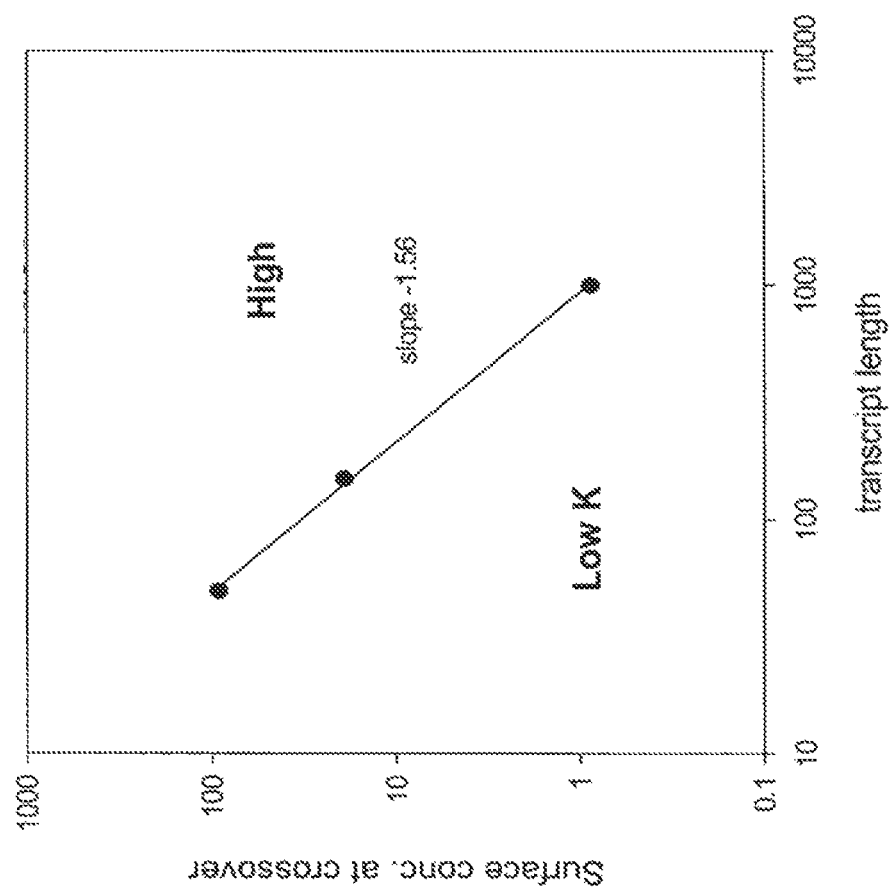
FIG. 11 shows the target length dependence of the value c* characterizing the cross-over from dilute to concentrated regimes in the isotherms of FIG. 10.

FIG. 11 shows the dependence of c* on transcript length, $c \sim 1/L^y$; the limited available data suggest $y \cong 3/2$. This curve delineates the boundary between dilute (below the line) and concentrated (above the line) regimes. Generally, to optimize capture efficiency and hence sensitivity of detection of rare messages, it will be advantageous to operate in the dilute regime in order to benefit from a high effective affinity constant. This advantage is particularly significant for long targets. Preferably, to facilitate detection, targets will be labeled in multiple positions, for example by incorporation of labeled dNTPs during reverse transcription, as described herein. Conversely, the analysis of experimentally recorded signal intensities must reflect the fact that cDNAs of different lengths, even when they are present at equal abundance, generally will produce substantially different signal intensities. That is, solution concentrations must be evaluated using the effective affinity constants if message abundances are to be reliably determined.

I.2.2B Effect of Capture Probe Placement: Terminal Capture Sequences—

Figure 12A:
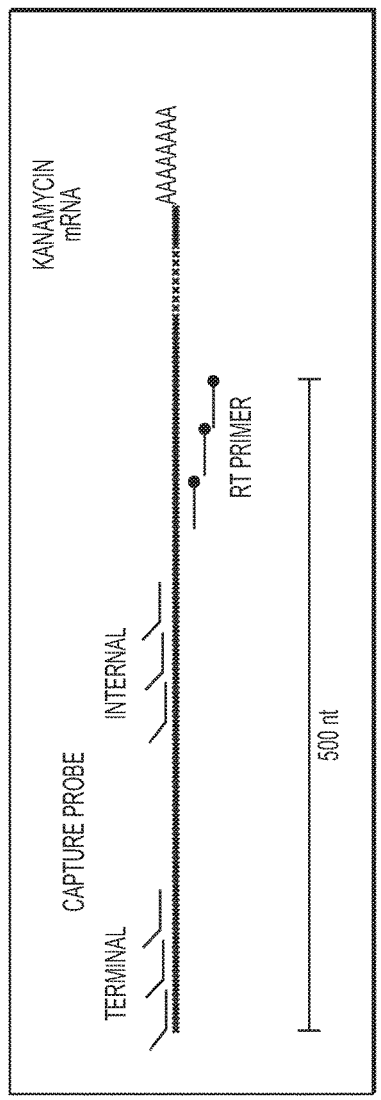
FIG. 12A shows a multiple primer-multiple probe (mpmp) design, illustrated for the case of producing a 500 nt cDNA.
Figure 12B:
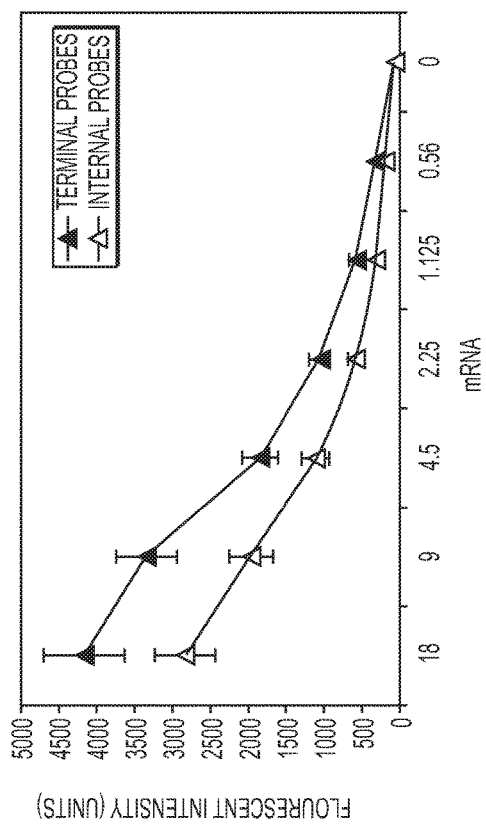
FIG. 12B shows a comparison of titration curves for the 500 nt cDNA, one of these obtained by capture to a probe matching a subsequence in the interior of the cDNA, the other obtained by capture to a probe matching a subsequence near the cDNA's 5' terminus.
Figure 13:
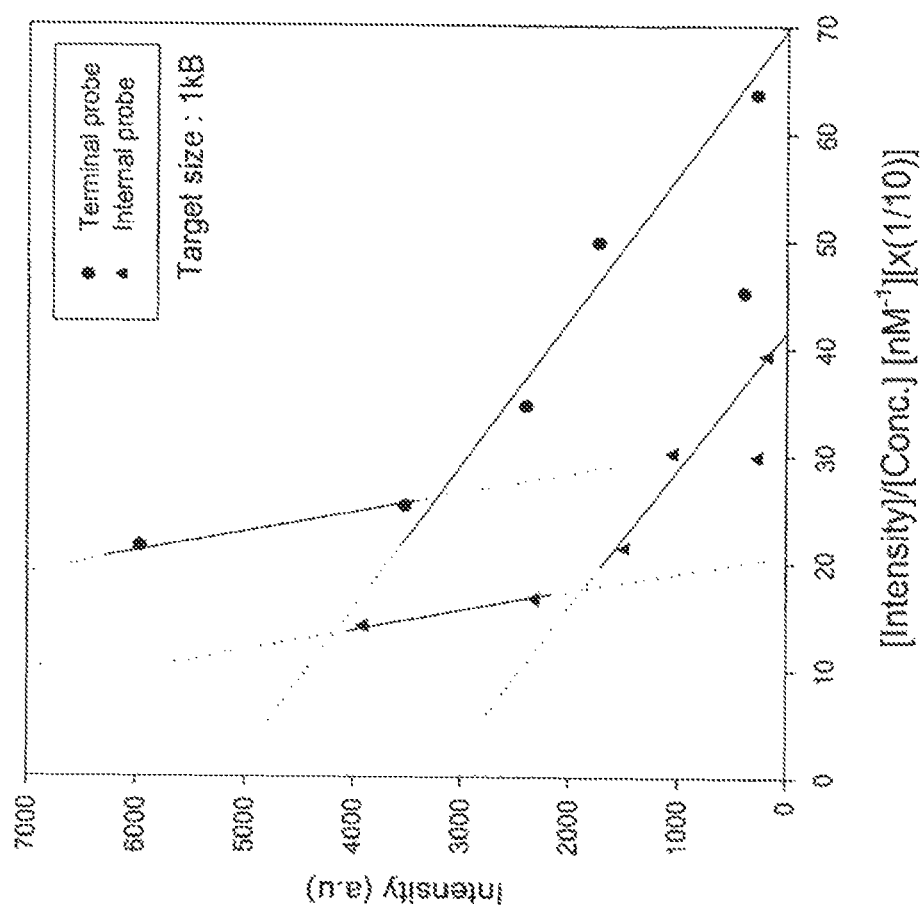
FIG. 13 shows adsorption isotherms, in a linearized representation obtained by transformation of the titration curves for the 500 nt cDNA depicted in FIG. 12.

It is also disclosed herein that the effective affinity governing capture efficiency and hence assay signal and sensitivity is enhanced by locating capture subsequences near the 5' end of long transcripts, as illustrated in FIG. 12A, depicting the relative alignment of RT primers as well as internal and terminal probes relative to the 1,200 nt Kanamycin mRNA. FIG. 12B displays the comparison of titration results obtained for the capture of a 500 nt transcript to two different (sets of) 19-mer probes, one (set) directed to a subsequence located near the 5'-end of the transcript, the other directed to a subsequence located in the interior of the transcript. The use of the "terminal" capture probe leads to an enhancement by a factor of ~1.5 in assay signal over that recorded with "internal" probe. Transforming these results in accordance with the adsorption isotherm format (FIG. 13) indicates the effect of placing the capture subsequence near the transcript's 5' terminus to have an effect on the isotherms analogous to that produced by length reduction. This is consistent with the view that capture of the terminal subsequence is equivalent to capture of a shorter target, requiring less configurational adjustment in probe layer as well as incoming target, and thereby reducing chain entropy-mediated repulsive effects, as elaborated below.

The results disclosed so far imply that the quantitative determination of message abundance requires a careful analysis of the effective affinities governing the interaction between targets and anchored probes.

I.3 Empirical Design Rules—

A priori knowledge of the sequence of transcripts to be detected in "diagnostic" expression profiling permits the design of capture probes directed against specific target subsequences in order to enhance sensitivity, preferably selecting terminal capture probes, modulate the dynamic range by selecting the operating regime to be above or below c*, and to optimize specificity, methods and designs for which are described in greater detail in application Ser. No. 10/892,514.

The following empirical design rules are useful in guiding the optimization of probe-target interaction. These rules also indicate the need for corresponding corrections in the analysis of signal intensity patterns, as further discussed in Sect. II.

1—Minimizing Target Length
  Minimize the target length, L, in order to maximize the effective affinity constant, $K^*=K^*(L)$, governing target hybridization to an immobilized probe;
2—Placing Capture Subsequence near 5' Terminal
  For given target length, place the designated capture subsequence as close as practical to the target's 5' terminus;
3—Selecting Dilute or Concentrated Regime of Operation
  Control the effective affinity constant, K*, governing interaction of a specific target with immobilized probe by working in the dilute regime to realize a high value of K*, or in the concentrated regime, to realize a low(er) value of K*;
  Corollary: Compressing Signal Dynamic Range
  For high abundance messages, produce long transcripts so as to reduce K*; for low abundance messages, produce short transcripts so as to increase K*, thereby compressing a given range of message abundance into a smaller range of signal intensity;

4—Adjusting Grafting Density for Quantitative Analysis

To perform a quantitative determination of target concentration, limit the capture probe length to a maximum for given probe grafting density or limit the grafting density for desired probe length so as to avoid "saturation";

5—Adjusting Layer Configuration for Maximal Sensitivity

Set the grafting density, σ, to the maximal possible value without substantially reducing the rate of target penetration; limit α to a preset small multiple of probes per target at saturation;

6—Confining Duplex Formation (see below)

Select the bulk ionic strength (and, where practical, pH) so as to minimize the rate of target-target duplex formation without substantially reducing it in the probe layer;

These empirical rules will be made more precise on the basis of a phenomenological model developed in the following section.

II. Model of Target Capture to a Layer of Immobilized Probes

II.1. General Description

To account for the observations presented in Sect. I, and to provide a basis for the refinement of design rules into a systematic design process guiding the selection of optimal probe layer and target configurations, the present invention discloses a phenomenological model for the capture of single-stranded (ss) DNA or RNA targets to a layer of end-grafted probes, each such probe designed to be complementary to a designated "capture" subsequence within the cognate target. Specifically, this model views the formation of a duplex between a capture probe and a designated target subsequence as an adsorption process which requires the penetration of a portion of the target into the probe layer. This involves an elastic deformation of the layer as well as the confinement of (a portion of) the target which will be accompanied by a loss of configurational entropy. The formation of anchored probe-target complexes is thus viewed herein as a grafting process which mediates the transformation of the end-grafted probe "monolayer" into a probe-target "bilayer".

Polyelectrolyte Brush—

Figure 14:
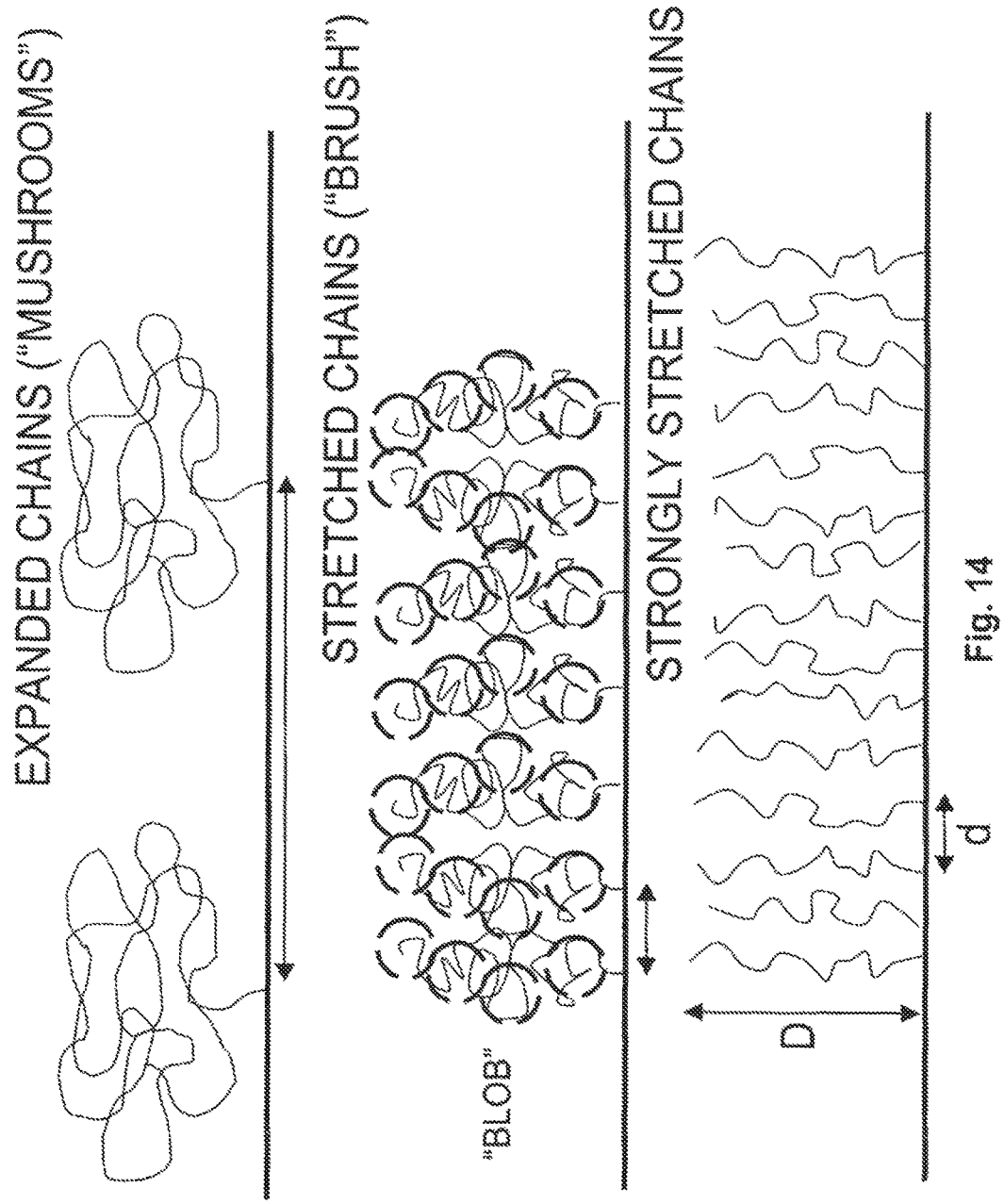
FIG. 14 shows a schematic illustration of different configurations adopted by end-grafted polymer chains as a function of grafting density.

In one way, the model presented herein is thus informed by the process of polyelectrolyte adsorption to a deformable substrate, this substrate displaying the characteristics of a polyelectrolyte "brush", or, under certain conditions, that of a polymer "brush, "composed of end-grafted probes (FIG. 14; Pincus, Macromolecules 24, 2912-2919 (1991)—incorporated by reference; see also: Fleer et al, Sect. 4 in: "Polymers at Interfaces", Chapman Hall, 1993). In a layer of end-grafted probes at lateral density σ, the characteristic separation, d, between adjacent probes, $\sigma \sim d^{-2}$, and the characteristic size, $\xi_\perp$, of each probe in a relaxed or expanded ("mushroom") configuration, are interrelated: as long as $\xi_\perp \ll d$, individual "mushroom" configurations are unconstrained by their neighbors; however, when probe chains start to overlap, "mushroom" configurations become constrained, and probes will adopt increasingly "stretched" configurations, thereby transforming the probe layer into a "brush" in which chain ends tend to be displaced toward the free surface (Fleer et al, op.cit.; Milner, Witten & Cates, Macromolecules 21, 2610-2619 (1988)).

As described herein, the high charge density realized within a layer of anchored oligonucleotide probes permits operation under a variety of external conditions, with the possibility of realizing a variety of probe layer configurations. These are determined primarily by the probe grafting density, σ, and by the effective linear charge density, f, 0<f<1, reflecting the degree of dissociation, α, of probes within the layer in response to solution conditions, especially pH, temperature and salt concentration, $C^S$.

For example, denoting by k the dissociation constant for the solution reaction AH⇌A⁻+H⁺, $\alpha_{Bulk}:=[A^-]/[AH]$ is given in terms of k and [H⁺] in the form $\alpha_{Bulk}=1/\{1+[H^+]/k\}$; generally $[H^+]>[H^+]_{Bulk}$ and $\alpha<\alpha_{Bulk}$, and f=f(α) or, more precisely, $f=f(k, C_{Bulk}^S)$. When the salt concentration, $C_{Bulk}^S$ in the bulk solution is low, counterions are retained in order to maintain electroneutrality in the interior of the brush at the expense of a toss of entropy of mixing. Under the action of the corresponding osmotic pressure, chains are expected to be fully elongated, regardless of grafting density. Conversely, at sufficiently high bulk salt concentration, excess mobile co-ions and counterions can penetrate into the brush and screen electrostatic interactions within the brush; as the osmotic pressure associated with the trapped counterions is diminished, the appearance of relaxed chain configurations—and a corresponding reduction in layer thickness—are expected. Under the high salt concentrations, in the range of ~100 mM to ~2M, frequently realized in conventional hybridization experiments, a collapsed state can result in which counterions are no longer distributed throughout the layer but are associated with anchored probe chains (or probe-target duplexes).

Interfacial Film of Short Amphiphiles—

In another way, the model herein is informed by the process of adsorption of solutes, say proteins, to monomolecular ("Langmuir") films composed of amphiphilic molecules such as phospholipids, surfactants or certain peptides adsorbed at an air-water or oil-water interface. Insertion of solutes into such a film requires local film compression, mediated by changes in chain packing and configuration, in a manner analogous to that produced by lateral compression. As a function of grafting density, the interplay of orientational and configurational degrees of freedom can produce a variety of phases; for present purposes, phases, or coexistence regions of high lateral compressibility are of principal interest. While the following discussion employs the language of polymer theory, it is understood that any extensions or refinements likely possible for layers of short probe chains by reference to the known phase behavior of interface-adsorbed amphiphilic ("Langmuir") films also are included herein.

The phenomenological model is to elucidate the critical role played by elastic effects arising from distortions in target and probe layer configurations required for duplex formation between targets and probes, particularly when either targets or probes are immobilized. Further, it is to provide a basis for the refinement of the empirical design rules delineating optimal "operating regimes" for target capture to immobilized probe layers and for the completion of assay protocols. For example, such protocols may call for target-mediated, polymerase-catalyzed probe elongation, as illustrated below in connection with a method of signal amplification which will require penetration into the probe layer of additional assay constituents including enzymes.

II.1.1 Probe Layer Deformation and Target Confinement: Renormalization of Affinity Constant A (portion of a) target penetrating into a layer of end-grafted probes will increase the local segment concentration and will generate a corresponding osmotic pressure; in addition, the incoming target also will induce an elastic deformation of the layer which is mediated by chain elongation ("stretching"), as illustrated in FIG. 14. The osmotic pressure and elastic energy of chain elongation act to repel the incoming target, and thus provide a repulsive contribution, $G_P$, to the free energy of duplex formation. It is this repulsive free energy which contributes to the entropic stabilization of colloidal suspensions; however, while in that instance, optimal grafting layer configurations are those which minimize interpenetration of chains on colloidal particles coming into contact, the present objective in optimizing capture probe layer configurations is to facilitate target strand penetration into the layer.

At very low grafting density, for example, in the limit $d\sim\sigma^{-1/2}\gg R_{G,\,T}$, isolated probes assume a relaxed ("mushroom") configuration of size $R_{G,\,P}\sim aP^\nu$, $\nu=\tfrac{3}{5}$, and target capture will proceed in the absence of the constraints imposed by local chain "packing"; however, the maximal number of targets captured will be small and the corresponding assay signal low. Conversely, at high grafting density, for example such that $d\sim\sigma^{-1/2}\lesssim\xi_T\ll R_{G,\,T}$, particularly under conditions producing full chain elongation, the number of available capture probes will be high, but the lateral compressibility of the layer will be low and target capture will be inefficient and the assay signal low; here, $\xi_T$ denotes a characteristic target "blob" size in a partially elongated target. Accordingly, to optimize target capture to a layer of immobilized probes, the grafting density is optimized so as to provide the highest possible number of probes per unit area without substantially reducing compressibility. For example, given an actual target of which a portion of size T is to participate in duplex formation, the optimal grafting density can be found by providing a synthetic target of size T and determining—under fixed external conditions—the assay signal reflecting fraction of captured target as a function of increasing grafting density until a plateau or peak in the resulting profile is obtained. "Indirect" probe anchoring, for example to a flexible "backbone" which is in turn attached to the solid phase, also can alleviate constraints. See U.S. application Ser. No. 10/947,095, filed Sep. 22, 2004, entitled: "Surface Immobilized Polyelectrolyte with Multiple Functional Groups Capable of Covalent Bonding to Biomolecules," incorporated by reference.

Figure 15:
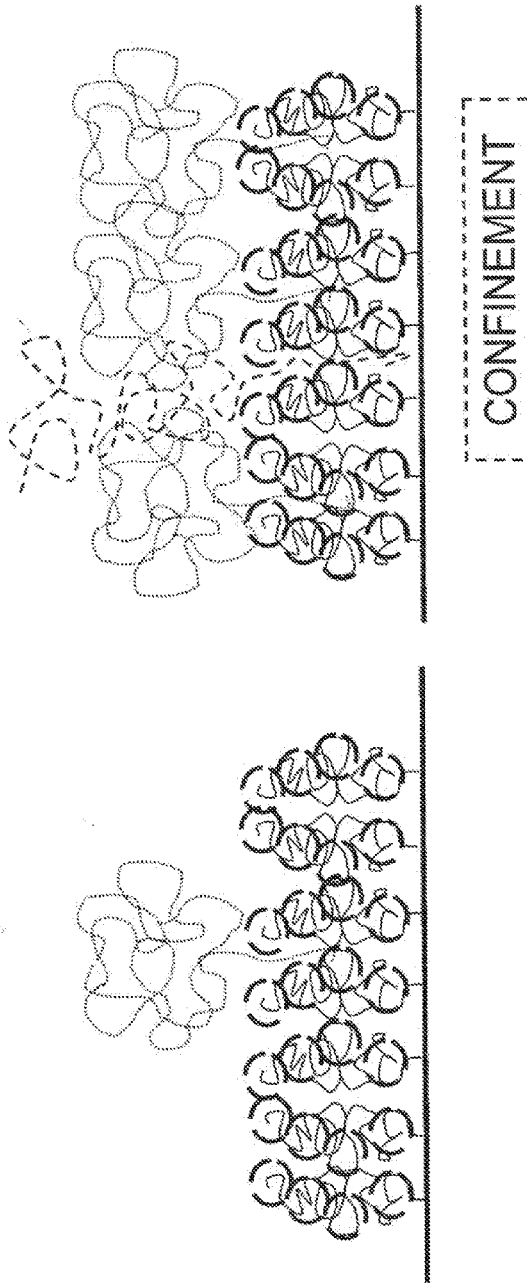
FIG. 15 shows a schematic illustration of target strand confinement in the course of capture to end-grafted probes.

Targets, or portions of targets, in order to make contact with the capture sequence, must adjust to the local configuration of the probe layer or the already formed composite probe-target layer (see FIG. 10B, 10C, FIG. 15). The resulting confinement of target strands and corresponding loss of configurational entropy—even in the dilute regime—represents a repulsive contribution, $G_T$, to the free energy of duplex formation. The degree of confinement imposed on ssDNA or RNA, will depend on the specific unconstrained ("relaxed") configuration assumed by these polyelectrolytes under conditions prevailing in solution—even without the considering the possibility of sequence-specific interactions ("folding"), a complex phase behavior is expected (see e.g., Schiessel & Pincus, Macromolecules 31, 7953-7959 (1998)). For purposes of illustration: penetration of a portion of target of length T and, assuming a Gaussian coil configuration, of size $R_{G,\,T}\sim aT^\nu$, $\nu=\tfrac{3}{5}$, into a probe layer of local grafting density, $\sigma$, will require an elastic energy of target deformation $G_T\sim(R_{G,\,T}/\sigma^{-1/2})^2\sim a^2T^{2\nu}/\sigma$. That is, the larger the portion of target penetrating into the layer relative to the characteristic distance between adjacent probes, $d\sim\sigma^{-1/2}$, the more difficult the requisite deformation of the target.

The sequence-dependent "condensation" energy, $G_C$, which favors the formation of probe-target pairs must be balanced against these repulsive contributions to the free energy, $G_{el}=G_P+G_T$; accordingly, the free energy governing probe-target complex formation has the form $G\sim G_{el}-G_c$. An immediate consequence of this form of the free energy is a "renormalization" of the sequence-dependent affinity constant, $K_{SS}$, to an effective affinity constant, $K^*<K_{SS}$. As long as $G_{el}<G_C$, condensation will still occur, but with a smaller net gain in free energy, $-\Delta G^*_C=-\Delta G_C+G_{el}>-\Delta G_C$, and a correspondingly smaller effective condensation energy implies a smaller effective affinity constant, $$K^*\sim\exp(-\Delta G^*_C/RT)<K_{SS}\sim\exp(-\Delta G_c/RT);$$

as well as a lower "melting temperature", $T^*_M<T_M$, wherein $T^*_M$ is determined from the condition $\Delta G(T^*_M)=\Delta G^*_C$ $(T^*_M)=0$ and $T_M$ is determined from the condition $\Delta G_c(T_M)=0$. Substantial corrections to the sequence-specific values must be anticipated, in fact, elastic effects can suppress duplex formation altogether.

One method of assessing effective affinity constants is the empirical method, described herein, of performing isotherm measurements using probe payers of defined configuration and synthetic targets comprised of one target containing only the subsequence of interest of length T, and additional targets containing the subsequence of length T embedded in a total sequence of length L>T. Ignoring excluded volume effects, the probe layer configuration is determined, for given probe length, P, by grafting density, $\sigma$, and effective linear charge density, f, 0<f<1, the latter in turn reflecting experimental conditions, especially salt, pH and temperature, realized in bulk solution. From these isotherm measurements, values for the effective affinity constant in various regimes of target concentration are readily extracted.

Another method of assessing effective affinity constants, complementary to the empirical method, is that of invoking a phenomenological model of probe-target capture to account for the effects of elastic and electrostatic interactions.

II.1.2 Design Considerations

Probe Layer Configuration: Preferred Grating Density—

For given grafting density, $\sigma$, overlap between adjacent chains in a "mushroom" configuration begins to occur when the transverse displacement of probe chains, $s_\perp$, is comparable to d, that is, $s_\perp\sim aP^\nu\cong d$, P denoting probe length and a denoting a monomer or segment size. With $\nu=\tfrac{1}{2}$, the condition becomes $a^2P\sim d^2\sim 1/\sigma$ and hence $P\sim 1/\sigma a^2$. Given a preferred length, P, for the capture probe of interest, the grafting density therefore preferably is adjusted such that $\sigma<1/a^2P$.

Considering target penetration to increase segment density in a manner equivalent to that of an increase in probe grafting density, suggests a modification of this rule. Given a preferred length, P, for the capture probe of interest, and anticipating penetration of a portion of target occupying at least the same footprint as the probe, select a preferred grafting density such that $\sigma_{e\!f\!f}=g\sigma<g/a^2P$, $\tfrac{1}{2}<g<1$; for example, with $g=\tfrac{1}{2}$, that is, T=P (a situation realized to good approximation in the case of terminal capture, FIGS. 12A, 12B, 13), select $\sigma_{e\!f\!f}<\tfrac{1}{2}a^2P$ in order to accommodate the anticipated insertion of target.

Free Energy of Probe Layer: Osmotic Pressure and Elastic Deformation—

The penetration of a target strand, or a portion thereof, into a brush of end-grafted probes leads to an increase in local segment density, $\phi$. For a brush of area $A_0$ and thickness $D=D(\sigma)$ containing $n_P$ chains, $\phi\sim S/A_0 D(\sigma)\sim(n_P/A_0)P/D(\sigma)$, P representing the number of segments per chain; hence, $\phi\sim\sigma P/D(\sigma)$. An increase in $\phi$ leads to an increase in the osmotic pressure, $\Pi\sim\phi^w$, w denoting a characteristic exponent, and to a decrease in the layer compressibility, $\chi := (1/\phi)\partial\phi/\partial\Pi$. Introduction of each additional segment also leads to elastic deformation. For example, in a brush composed of strings of "blobs" (FIG. 14), elastic deformation reduces the characteristic "blob" size, $\xi_P$, with a corresponding cost in free energy arising from the requisite stretching of chain segments and the concomitant increase in brush thickness, $D=D(\sigma)$. Assuming each blob to contain $P_B$ segments, $\xi_P \cong aP_B^\nu$, yields $P_B \cong \xi_P^{1/\nu}/a$; if each probe chain of length P contains $P/P_B$ blobs spanning the thickness of the brush, $D \cong (P/P_B)\xi_P \sim aP \xi_P^{1-1/\nu}$ and, with $\xi_P \sim \sigma^{-1/2}$, $D \sim aP \sigma^{1/3}$. That is, an increase in grafting density leads to an increase in layer thickness as a result of chain elongation. This type of scaling relation arises very generally from the balance of a repulsive contribution (e.g. excluded volume, electrostatic interactions) and the attractive contribution of chain elasticity.

Control of Grafting Density—

Unless limited by the lateral density of adsorption sites provided on solid phase carrier surfaces, the grafting density realized in the formation of the probe layer by covalent end-grafting reflects the balance between a characteristic adsorption ("binding") energy (per probe) and repulsive interactions such as the elastic deformation of the growing probe layer required to accommodate an additional probe. That is, the grafting density defines a characteristic area per chain, $A_P \sim d^2 \sim 1/\sigma$. In this case, grafting density reflects the conditions pertinent to the covalent functionalization of solid phase carriers, notably the concentration of probe and the conditions of incubation.

The experimental observation of a maximal capture efficiency at typical values of $P \cong 30$ suggests a characteristic "footprint", $\xi_P$, per chain. Using $p_0 \cong 6*10^5$ (FIG. 6B) as an estimate of the maximal number of targets (of size L=25 nt) accommodated per bead (of 3.2 μm diameter), and assuming each of these targets to be hybridized to one probe equal in size to the captured target, the average molecular area is estimated to be $A_P \sim \pi(1.6 \mu m)^2/2*6*10^5 \sim 0.65*10^3$ Å$^2$ following target capture, or twice that value prior to target capture, the latter corresponding to a probe grafting density $\sigma = 1/A_P \cong 7.5*10^{12}/cm^2$. This suggests a picture of a "self-limiting" grafting process producing—at least under conditions applied in the production of solid phase carriers used in the experiments cited here—a layer in which end-grafted probes are no longer in their relaxed configuration but assume a partially elongated configuration; partial elongation would be consistent with a configuration in the form of an elongated string of "blobs" of characteristic radius $\xi_P \sim (1.25*10^3 \text{ Å}^2/\pi)^{1/3} \sim 20 \text{ Å} < R_{G,P} \cong 9 L^{1/2} \cong 50 \text{ Å}$ (Tinland et al, op.cit.), $R_{G,P}$ denoting the radius of gyration of an unconstrained probe chain in solution. That is, in a brush produced by a "self-limiting" grafting process, $\sigma \cong \xi_P^{-2}$.

As discussed herein, high grafting densities, particularly those realized in typical conditions of in-situ synthesis of oligonucleotide probes (Lipshutz, R. J. et al., Nat. Genet. (suppl.), 21, 20-24 (1999); Shchepinov, M. S. et al., Nucleic Acids Research 25, 1155-1161 (1997)) generally may be unfavorable. Spotting of probes generally will not produce end-grafted layers but rather more complex "crumpled" layers (Netz & Joanny, Macromolecules 32, 9013-9025 (1999)) in which molecules may be attached to the solid phase at multiple (random) sites, leaving only a small portion of probe sequences—unknown a priori and highly variable from spot to spot—accessible to the target. Control of grafting densities may be difficult to achieve in this situation.

Figure 16:
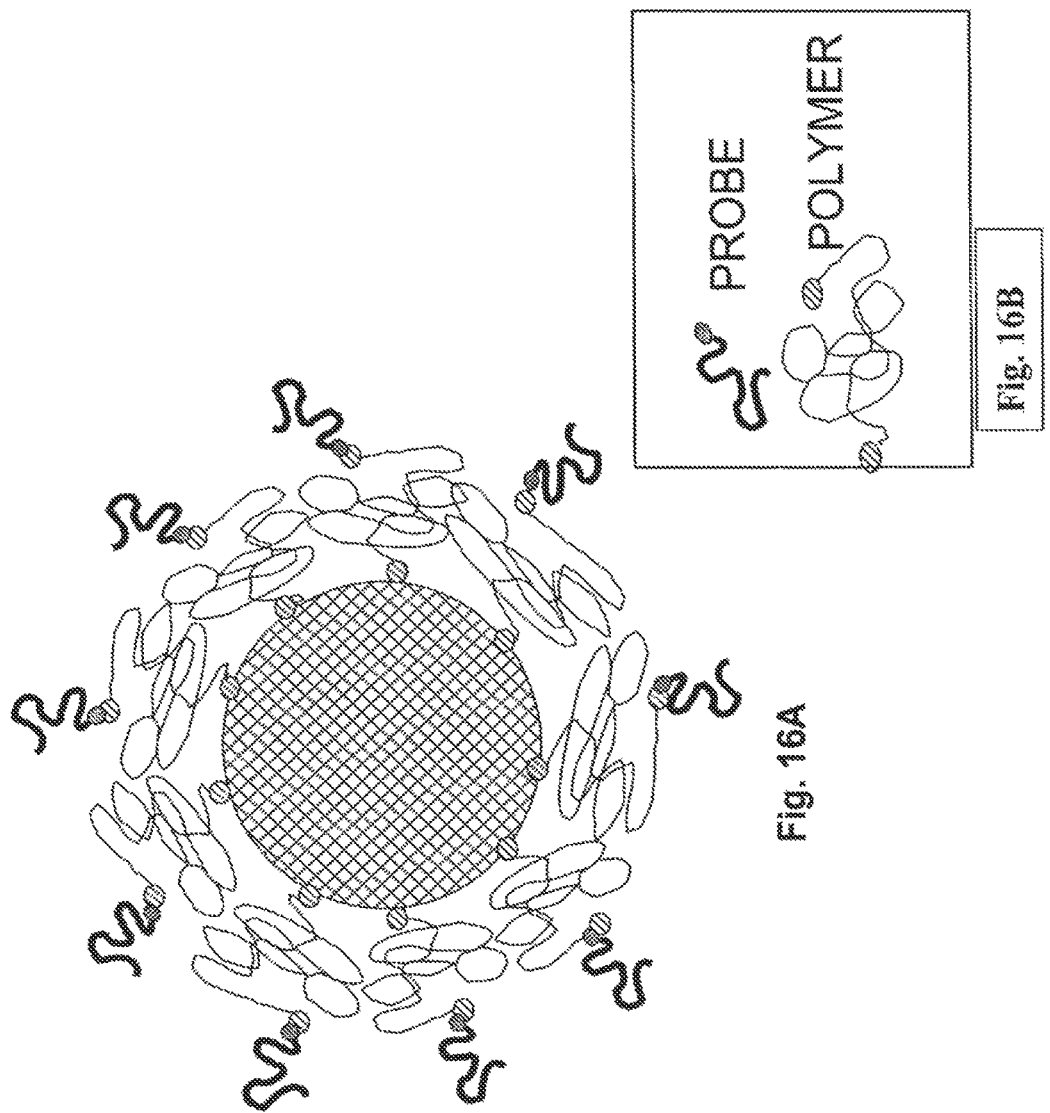
FIG. 16A shows a schematic illustration of the method of controlling the grafting density of probes displayed on the surface of a microparticle by way of introducing a bifunctional polymeric modifier.
FIG. 16B shows a larger view of a probe interacting with a polymer.

Preset values of a lower than that attained in the "self-limiting" case are realized, for example, by introducing an intermediate step into the process of microparticle functionalization. Specifically, introduction of a bifunctional modifier in the form of a functionalized polymer such as bifunctional polyethyleneglycol ("PEG") molecules of adjustable molecular weight, biotin-binding proteins like NeutrAvidin, Streptavidin or Avidin, and any other heterofunctional polymeric linkers of known molecular size sets an upper limit on the probe grafting density, which is now determined by the size of the modifier and its lateral "packing" at the bead surface (FIGS. 16A, 16B). In the embodiment using the READ format, in a first step, the modifier is covalently attached to a color-encoded microparticle ("bead"), and, in a second step, the modifier is functionalized by covalent attachment of the capture probe, preferably way of a 5' modification introducing a functional group such as amine or biotin using standard conjugation chemistry.

Target Strand Confinement: Dilute and Concentrated Regimes of Adsorption—

The discussion of the elastic response of the probe layer to target insertion suggests that elastic deformations of the composite probe-target layer give rise to the observed cross-over between dilute and concentrated regimes in the adsorption isotherms (FIG. 10A), delineated by the locus c*(L) for which the limited available data suggest $c^* \sim 1/L^{3/2}$ (FIG. 11).

In the limit of small targets, the principal effect of capture will be that of increasing the segment density within the probe layer, as discussed above, suggesting the cross-over to reflect the transition of the probe layer, or more generally, the layer formed by capture probes of characteristic size $\hat{\xi}_P < \xi_P$ and already captured targets of characteristic size $\hat{\xi}_T < \xi_T$, into a regime of lower compressibility. That is, the cross-over occurs when $n_T^* \hat{\xi}_T^2 + n_P^* \hat{\xi}_P^2 \sim \eta^* A_0$, hence $\eta^* \sim (n_P^*/A_0)\hat{\xi}_P^2 + (n_T^*/A_0)\hat{\xi}_T^2 \sim p_0 \hat{\xi}_P^2 + c^* \hat{\xi}_T^2$ and $c^* \sim (\eta^* - p_0 \hat{\xi}_P^2)\hat{\xi}_T^2$. In the special case $\hat{\xi}_P^2 \cong \hat{\xi}_T^2 \cong \hat{\xi}^2$, $c^* + p_0 \sim \eta^*/\hat{\xi}^2$, or, assuming $\hat{\xi}^2 \sim L^y$, $0 \leq y \leq 1$, $c^* + p_0 \sim \eta^*/L^y$; in the special case $n_P^* = n_T^* = n^*$, $\eta^* \sim (n^*/A_0)\hat{\xi}_{PT}^2$ or $c^* = (n^*/A_0) \sim \eta^*/\hat{\xi}_{PT}^2$, where $\hat{\xi}_{PT}^2$ represents the footprint of the probe target duplex; here, as before, $0 \leq \eta^* \leq 1$. This limit may be realized either by providing a short target, not a generally available design in practice, or by placing the designated target sequence in proximity to the target's 5' end. The latter possibility is illustrated herein in connection with FIG. 15.

In contrast, in the limit of large targets, in exact analogy to the "self-limiting" grafting process of producing the grafted probe layer, the cross-over reflects the incipient overlap ("crowding") of target strands in the growing layer of captured targets of (overall) size L and characteristic "footprint" $\hat{\xi}_T^2$; target overlap occurs when $n_T^* \hat{\xi}_T^2 \sim \eta^* A_0$, $0 \leq \eta^* \leq 1$, implying $c^* \sim n_T^*/A_0 \sim \eta^*/\hat{\xi}_T^2 \sim 1/L$ where $\eta^* A_0$ represents the fraction of the available area covered by captured target.

Adjusting Grafting Density to Allow for Target Penetration, Refined

The expression derived for the second case represents a design rule which may be applied to optimize the grafting density of the probe layer so as to ensure realization of the dilute regime in accordance with the boundary delineated in FIG. 11:

Adjust grafting density so as to maximize $c^* \sim \eta^*/L + p_0$ (or analogous condition for the more general case, $T \neq P$); for example, in the preferred embodiment, select specific target lengths, L, for example, as described for the case of cDNA targets by placement of RT primers, then adjust σ.

The two limits represent special cases of the more general case in which the cross-over reflects a transition in the elastic response of the hybrid probe-target layer. The elastic deformation of the probe-target hybrid, in conjunction with the elastic deformation of the target assuming the confined configuration required for duplex formation, also is invoked herein to account for the observed dependence of target capture efficiency on $1/L^x$, $3/2 \leq x \leq 2$, in the adsorption isotherms recorded for model targets containing the same capture subsequence, T, embedded within a sequence of increasing overall length, L. Thus, the probability of "locating" a finite subsequence occupying a finite volume within a "coil" of volume $R_{G, T}{}^3 \sim L^{3\nu}$, will scale as $\sim 1/L^{3\nu}$, $\nu = 3/5$.

Target Capture under Conditions of Low (Bulk) Ionic Strength: Polyelectrolyte Brush—

Typical values of grafting densities described herein in relation to the preferred embodiment of the invention, namely $\sim 10^6$ per bead of 3.2 μm diameter (or $\sim 3*10^{12}/cm^2$) correspond to high intralayer volume charge densities, $zC^P$. For example, for an oligonucleotide of length P=20, assuming a corresponding probe layer thickness D~50A, $C^P \cong 10^6/(\pi(3\cdot 2)^2 D) \sim 10$ mM for the concentration of probe chains, and thus yielding a corresponding value of $fC^P = 200$ mM, f=20, for the local concentration of charges associated with (fully dissociated) backbone phosphate groups.

In electrochemical equilibrium, the concentrations of cations and (poly)anions present in the interior of the probe layer and in bulk solution are interrelated in accordance with the condition $C^+C^- = C_{Bulk}{}^+ C_{Bulk}{}^-$ Electroneutrality requires, within the probe layer, $C^- + fC^P = C^+$, and in bulk solution, $C_{Bulk}{}^+ = C_{Bulk}{}^- = C_{Bulk}$. Accordingly, the concentration of cations within the layer, for given negative charge $fC^P$, can substantially exceed the concentration of cations in bulk solutions:

$$C+ = \tfrac{1}{2} fC^P (1 + \{1 + (4 C_{Bulk}{}^2 / fC_P{}^2)\}^{1/2}$$

For example, in the limit $C_{Bulk}/fC^P \ll 1$, $C+ \sim fC^P \gg C_{Bulk}$. That is, counterions are retained within the brush even in the presence of a large gradient in ion concentration; in fact, they are distributed throughout an effective volume, $V_{eff}$, which is smaller than the volume, V, of the brush by the finite volume occupied by the probe chains, $V_{eff} \sim V(1-\phi)$.

The corresponding Debye screening length, $\xi_E \sim 1/\kappa$, associated with the backbone charge, $fC^P$, per chain, is obtained from the expression $\kappa^2 = 4\pi l_B fC^P$, $l_B = e^2/\epsilon T$ denoting the Bjerrum length, and $C^P = P/d^2 D$. Balancing the repulsive contribution arising from the osmotic pressure $\Pi = fC^P T$ generated by counterions trapped within the brush with chain elasticity, $fC^P T = kD/d^2$, with an elastic constant k=T/$a^2 P$, yields $D \cong f^{1/2} aP$, independent of grafting density, so that $\xi_E \cong d(a/4\pi l f^{1/2})^{1/2}$. This scale is set by the mean separation, d, between chains, and hence the grafting density. In the limit $\xi_E \leq D$, chains are elongated for any degree of charging, f>0, producing the maximal brush thickness independent of grafting density. Provided that the grafting density is sufficiently low so as to accommodate penetration of incoming target, capture to such a layer in the configuration of a "bed of nails" can proceed without significant elastic distortion of the probe layer. The return to partial chain elongation in accordance with the "blob" configuration is achieved by addition of free co- and counterions at sufficient concentration so as to ensure that the Debye screening length $\kappa_{Free}{}^{-1}$ associated with these free ions is comparable to $\xi_E$ so that $\xi_E \kappa_{Free} \geq 1$. For such a screened brush, the internal configuration, while qualitatively resembling that of the semidilute polymer brush composed of a string of "blobs", will respond to conditions maintained in bulk solution in order to maintain electrochemical equilibrium.

Confining Duplex Formation to Interior of Charged Probe Layer—

In this case, while exposed to a salt concentration of only 1 mM in solution, generally considered to preclude duplex formation (Primrose, "Principles of Genome Analysis", Blackwell Science, 1995), the target, once it has penetrated into the probe layer, actually encounters a far higher local salt concentration and conditions of electrostatic screening that are favorable to duplex formation. That is, the probe layer provides a local chemical environment permitting probe-target hybridization under nominal conditions of extreme stringency in the bulk solution which counteract the formation of secondary structures in ssDNA or RNA and prevent reannealing of dsDNA in bulk while permitting (local) duplex formation within the probe layer. This scenario preferably is realized in accordance with the rule:

Adjust grafting density so as to ensure a condition of high brush interior charge and eletroneutrality to realize conditions permitting duplex formation while selecting conditions of high stringency in external solution so as to prevent duplex formation.

II.2. Procedures

II.2.1 Assay Design Optimization

Given a sequence, or sequences, of interest, specifically a set of mRNA messages, proceed as follows, applying design rules as appropriate:

| | |
|---|---|
| S | Target Subsequence of Interest |
| L | Target Length (number of nucleotides); |
| $C_T$ | Target Abundance; |
| ampC | Target Abundance following Amplification |
| $S_P$ | Primer Sequence |
| $S_C$ | Capture Sequence (i.e, target subsequence to be analyzed by capture to probe) |
| λ | Linear Labeling Density |
| P | Probe Length (number of nucleotides); |
| σ | Probe Grafting Density |
| $C_S$ | Salt Concentration |
| C* | Target Concentration at Cross-over |
| L* | L(C*); |

SelectTargetLength(C, C*, $S_P$);    /* By placing primer, select target length in accordance with given or anticipated target abundance */

{

IF(C LOW)   RETURN( L < L* );    /* ensure operation in dilute regime */

```
            IF(C HIGH)    RETURN( L > L* );    /* ensure operation in conc
                              regime */
}
SelectCaptureSequence (ProbeSeq);        /* The optimization of
                                            primer and probe
                                            sequences preferably is
                                            performed concurrently (see
                                            co-pending application) */
{
        RETURN(S_C = TerminalCapture Sequence( ) );
}
SelectFinalTargetAbundance(L, L*, C);    /* For given initial message
                                            abundance, select target
                                            amplification conditions to
                                            establish operating regime */
{
        IF( L > L*)
        {
                IF(C LOW)         RETURN( ampC ≤ C*);   /*
                                                          dilute
                                                          regime
                                                          */
                IF(C HIGH)        RETURN( ampC > C*);   /* conc
                                                          regime
                                                          */
        }
        ELSE IF( L < L* )
        {
                IF( C LOW )       RETURN( ampC > C*); /*
                                                        best to operate in conc
                                                        regime */
                IF( C HIGH )
                {
                        IF( C < C* )    RETURN( ampC ≤ C*);
                        ELSE            RETURN( ampC = C);
                }
        }
}
SelectLabelingDensity(L, ampC);          /* NOTE: if m'plex RT or
                                            m'plex amp,
                                            λ will be identical for all
                                            targets */
{
                                         /* for long targets: operate
                                            in dilute regime, select high
                                            labeling density */
                                         /* for long targets at high
                                            abundance: select low
                                            labeling density */
        RETURN(λ);
}
OptimizeTargetConfiguration(L, λ, C, S_C, S_P, S)
{
        IF( C Fixed )       L = SelectTargetLength(C, C*, S_P);
        ELSE IF( L Fixed )  ampC =
                            SelectFinalTargetAbundance(L, L*,
                            C);
        λ = SelectLabelingDensity( );
        S_C = SelectCaptureSequence (ProbeSeq);
}
OptimizeProbeLayerConfiguration( )
{
        P = SelectProbeLength( );        /* maximize K_SS while
                                            minimizing cross-
                                            hybridization */
        σ = AdjustGrafting Density(P, L);  /* the longer the probe, the
                                              lower σ; allowing for
                                              insertion of target of known
                                              length */
}
OptimizeRepresentation( )
{
        SelectTypeRedundancy( );
}
OptimizeReactionConditions( )
{
        SelectIonicStrength( );
}
```

```
main( )
{
FOR( each Target in Designated Set )
        {
                        OptimizeTargetConfiguration( );
                        OptimizeProbeLayerConfiguration( );
                        OptimizeRepresentation( );
        }
        OptimizeReactionConditions( );
}
```
II.2.2 Evaluation of Effective Affinity Constant

```
    S_C     Capture Sequence (i.e., target subsequence to be analyzed by
            capture to probe)
    P       Probe Length (number of nucleotides);
    C_S     Salt Concentration
    EvalEffectiveFreeEnergy(S_C, P, C_S, pH);
    {
        ΔG_T = EvalTargetElasticFreeEnergy(TargetConfig,
ProbeLayerConfig);
        ΔG_P = EvalProbeLayerElasticFreeEnergy(TargetConfig,
ProbeLayerConfig);
        Return(ΔG = ΔG_T + ΔG_P − ΔG_C);
    }
    EvalCondensationFreeEnergy(S_C, P, C_S, pH, T);
    {
        Return( ΔG_C = SumNNBasePairInteractions(S_C, P, C_S, pH, T) );
    }
    main( )
    {
        FOR( each Target in Designated Set )
        {
            ΔG_C = EvalCondensationFreeEnergy(S_C, P, C_S, pH, T);
            ΔG = EvalEffectiveFreeEnergy(ΔG_C, TargetConfig,
ProbeLayerConfig);
            K = K_0exp(−ΔG/kT)
        }
    }
}
```
II.2.3 Assay Signal Analysis

```
    aI:     Array of Assay Signal Intensities
    aK:     Array of Affinity Constants
    aS_C:   Array of Designated Target Subsequences
    aC_T:   Array of Target Concentrations
    aP:     Array of Probes
    EvalEffectiveAffinityConstant(aK, aS_C, aP)       /* See II.2.2 */
    {
        FOR( j=0; j ≤Number of Targets in Designated Set; j++)
        {
            ΔG_C = EvalCondensationFreeEnergy(aS_C(j), aP(j), C_S,
            pH, T);
            ΔG = EvalEffectiveFreeEnergy(ΔG_C, TargetConfig,
            ProbeLayerConfig);
            aK(j) = K_0exp(−ΔG/kT)
        }
    }
/* NOTE: evaluation of effective affinities generally will have to include
coaffinities */
    main( )
    {
        RecordAssaySignal(N, aI);
        EvalEffectiveAffinityConstant(aK, aS_C, aP, C_S, pH, T);
        CorrectAssaySignal(aI, aK);
        EvalTargetConcentration(aI, aC_T);
    }
```

III. Assay Methodologies

This section discloses several methodologies relating to optimization of sensitivity, dynamic range and assay specificity, particularly pertaining to the multiplexed analysis of abundances of highly homologous messages, and further discloses a design strategy for subtractive differential gene expression analysis using only a single detection color.

III.1 Tuning of Signal Intensities

In nucleic acid analysis, target analyte concentration can vary over a wide range. Thus, multiplexed expression monitoring generally will encounter a range of message abundance from low, corresponding to one or two mRNA copies per cell, to high, corresponding to $10^4$ copies per cell or more. The requisite dynamic range of 4 decades for the simultaneous detection of signals from the weakest and the strongest transcripts will exceed the capabilities of many cameras and recording devices. The modulation of probe-target affinities as well as certain methods of array composition provide the means to tune the signal intensity in accordance with known or anticipated message abundance.

III.1.1 Optimization of Array Composition: Operation in Dilute Vs Concentrated Regime The selection of RT primers for producing cDNA transcripts of desired length from an mRNA subsequence of interest, and the selection of 5'-terminal target subsequences for capture, in accordance with the considerations elaborated herein, permit the modulation of probe-target affinity and thus the control of the dynamic range of assay signals indicating target capture.

Selection of Transcript Length—

In the simplest case of an assay design calling only for reverse transcription, but not amplification, the concentration of cDNAs reflects the abundance of mRNAs in the original sample; that is, the target abundance is given. Then, a judicious choice of transcript length, and/or the placement of capture subsequences, permit the maximization of detection sensitivity and the simultaneous "compression" of signal dynamic range by way of tuning the effective affinity constant.

To compensate for the low abundance of transcripts representing rare messages, a short transcript length is preferably selected in order to realize the highest possible effective affinity constant and to maximize the assay signal produced by hybridization of these transcripts to anchored probes. This will ensure maximization of the detection sensitivity. Conversely, to compensate for the high abundance of transcripts representing common messages, a long transcript length is preferably selected in order to realize the lowest possible effective affinity constant and to minimize the assay signal produced by hybridization of common transcripts to anchored probes. This will ensure the (approximate) "equalization" of assay signals from rare and abundant messages.

Tuning of Transcript Abundance—

More generally, a situation may arise in which the selection of the optimal transcript length is subject to additional constraints. For example, as herein discussed, in the case of analyzing closely homologous sequences, the subsequences near the 5' termini of many or all targets in a given sample may be identical, and identification of a specific target may require preparation of a longer than otherwise desirable cDNA. Then, for given length, L, the target abundance, $t_0$, preferably will be selected (for example by one or more rounds of differential amplification, see below) so as to ensure, for rare message, operation below c* and/or, for abundant message, operation above c*.

Placement of Capture Subsequence—

Another method of enhancing the sensitivity of detection of transcripts present in low copy number is to provide capture probes directed to a target subsequence located near the 5' end of transcripts, rather than to subsequences located in the central portion of transcripts. As discussed in Section I, the central portions of the target tend to be less accessible, and require a greater degree of probe layer distortion, than do the terminal portions of the target, with a correspondingly lower effective affinity constant in the former situation.

By any available method, the preferred design aims to realize one of the following configurations.

|  | Short Transcript (L < L*) | Long Transcript (L ≥ L*) |
|---|---|---|
| Rare Message | high K* | high K* |
| Abundant Message | low or high K* | low K* |

With reference to FIG. 11, c* denotes the concentration indicating the cross-over from dilute to concentrated regime, and L* denotes the corresponding transcript length, L*:=L(c*).

The corresponding design procedure is summarized in Section II.2 as part of the Assay Design Optimization procedure within the functions: SelectFinalTargetAbundance(L, L*, C), SelectTargetLength(C, C*, $S_P$) and SelectCaptureSequence(ProbeSeq).

III.1.2 Control of Array Composition: Carrier Redundancy

Dynamic range and detection sensitivity can be further optimized by matching the number of probes of a given type to the anticipated concentration of the specific targets. Specifically, in the preferred READ format of the invention, the number of probes is readily adjusted by simply adjusting the number of microarticles ("beads") of particular type, a quantity also referred to herein as redundancy. A design rule for specifying the selection of optimal relative abundances of beads of different types is provided.

Ekins (U.S. Pat. No. 5,807,755) discusses a related method of designing spotted arrays of receptors to perform receptor-ligand binding assays. This method of the art requires that the concentration of receptors be significantly smaller than the concentration of ligand. As discussed below, this situation corresponds to a limiting case of the theoretical description presented below in which both $[P]_0$ and the number, $N_B$, of beads are small. However, Ekins neither contemplates the regime of high receptor concentration nor the related methods for dynamic range compression disclosed herein. Furthermore, Ekins does not contemplate the use of random encoded arrays of particles for receptor-ligand interaction analysis, nor does he contemplate the variation of the relative abundances of beads/probes of different type as a means to establish desirable assay conditions.

The reaction of interest is the complexation in solution of target molecules (which include, for example, ligands T) with receptor molecules P (which can be probes) displayed on solid phase carriers, such as color encoded beads, to form reversible complexes P·T. This reaction is governed by the law of mass action and has an affinity constant, K. Thus, for the case of a single receptor binding a single ligand:

$$P + T \xrightleftharpoons{K} PT$$

The law of mass action in its basic form delineates the relationship between the number of complexed molecules on a bead, [PT], the number of uncomplexed receptor sites on a bead, [P] and the total number of free ligand molecules available for reaction, [T]. Mathematically, $$K = \frac{[PT]}{[P][T]}$$

The bead displayed receptor molecules, P, are immobilized on the beads at the concentration of $[P]_0$ ($p_0$) molecules per bead. In the analyte, the initial concentration of ligand molecules, T, is $[T]_0$ ($t_0$) moles/l (or M).

At any instant, the concentration of complexed molecules on the surface is [PT] (c) molecules/bead. The number of uncomplexed receptor sites, [T](t), is given by ($p_0$−c). The number of ligand molecules available for reaction at any time is the difference between the initial number of ligands and the number of molecules of ligand already complexed. In an array of $N_B$ beads, all having receptor molecules of type P, the total number of complexes formed is equal to $cN_B$. Thus, in an analyte solution of volume V, the number of available ligand molecules is given by $VN_A t_0 - N_B c$; where $N_A$ denotes Avogadro's number. The law of mass action can be rewritten to include known variables in the form:

$$K = \frac{c}{(p_0 - c)\left(t_0 - \frac{N_B c}{VN_A}\right)}$$

The number of complexes c is directly proportional to the fluorescent signal obtained for each bead.

In this scenario, two extreme cases can be identified: $t_0 \gg N_B p_0 / v n_A$. The total number of ligand molecules in the analyte is far in excess of the number of total receptor sites. Addition of a few more beads into an equilibrated system does not affect the number of complexes on each bead appreciably. The number of complexes, and thus, the intensity of beads displaying such complexes, is independent of the number of beads. $t_0 \ll N_B p_0 / VN_A$.

The number of receptor sites available for reaction far exceeds the number of ligand molecules available. Under these circumstances, if a few more beads were added to an equilibrated system, some of the complexed ligand molecules would have to dissociate and redistribute themselves onto the newly-added beads to reattain equilibrium. In effect, the limiting situation is $c = t_0 VN_A/N_B$. Thus, for a given concentration of ligand molecules, the number of complexes displayed per bead, and thus the corresponding fluorescence intensity, is inversely proportional to the number of beads, $c \propto 1/N_B$.

Figure 17:
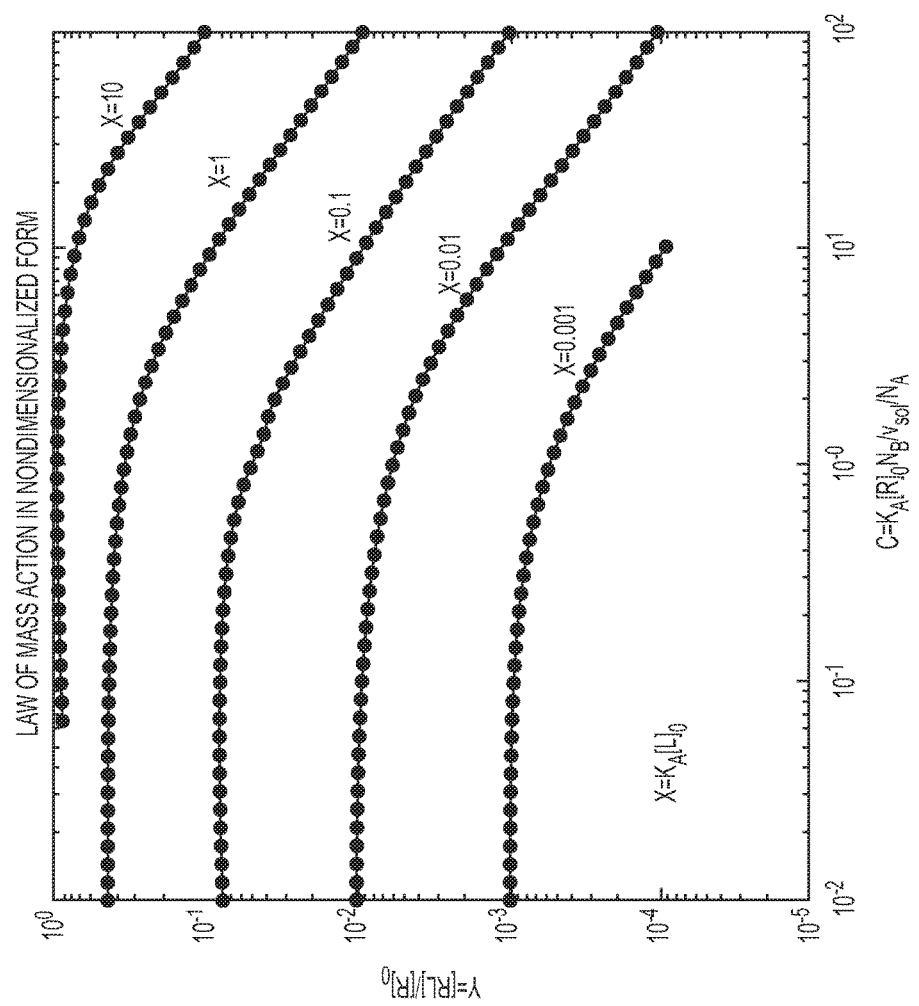
FIG. 17 shows the variation of (normalized) fractional occupancy, shown on the ordinate, with the quantity, shown on the abscissa, which is directly proportional to the number of microparticles ("beads") included in an array and to the (dimensionless) target concentration.

Introducing dimensionless variables, $Y = c/p_0$, $X = Kt_0$, and $C = Kp_0 N_B/N_A/V$, the equation for K can be rewritten in the form $Y/(1-Y) = (X-CY)$. FIG. 17 shows the variation of fractional occupancy, Y, with C, which is directly proportional to the number of beads and X, the nondimensionalized ligand concentration. For lower number of beads, Y is independent of C. This situation is equivalent to situation (a) above. Nondimensionally, when $X \gg C$, $Y \rightarrow X/(1+X)$ and is independent of C. Further, for $X \gg 1$, $Y \rightarrow 1$, which indicates that high ligand concentration and large values of the affinity constant ensure that the beads reach full occupancy. For larger values of C, Y decreases monotonically with C. With respect to situation (b) above, the limiting case is $Y = X/C$.

Sensitivity of Detection—

Control of the number of beads of a given type within a random encoded array provides a preferred means for producing signal intensities within desired limits. In the simplest case of single ligands binding to single receptors, maximum occupancy is obtained by reducing the number of beads below the knee of the curves in FIG. 17, given by $C_{knee} = 1 + X$.

Dynamic Range Compression—

As discussed earlier, in a multiplexed assay, often there is a large disparity in the concentrations of individual ligands to be detected. To accommodate within the dynamic range of a given detector the wide range of signals corresponding to this range in analyte concentration, it generally will be desirable that the number of beads of each type in a multiplexed reaction be adjusted according to the respective expected analyte concentrations. Specifically, it will be desirable that weak signals, produced by analytes present in low concentration, be enhanced so as to be detectable and that, at the same time, strong signals, produced by analytes present in high concentration, be reduced so as not to exceed the saturation limit of the detection system.

The equalization of specific signal intensities provided by dynamic range compression is particularly desirable when:
a) concentrations of ligands in an analyte solution are known (or anticipated) to vary widely.
b) binding affinities of some ligands are known (or anticipated) to be very weak.
c) receptor density for some bead types is known (or anticipated) to be low.

For example, in a 2 ligand-2 receptor system, with ligand concentrations, $t_{0,1} \gg t_{0,2}$, it is desirable that the corresponding relative abundances of beads displaying cognate receptors be adjusted in accordance with the condition $N_{B,1} \gg N_{B,2}$. Such reasoning is readily extended to assays involving a multianalyte solution containing a large number of ligands that is placed in contact with an array of beads containing corresponding cognate receptors.

Therefore, an array design rule for purposes of compositional optimization entails the following steps:

Select a desirable number of fluorophores or complexed molecules $c_i^d$ on beads of each type of interest.
1. Set $Y_i^d$ for each receptor-ligand pair on the basis of known or anticipated values of $p_{0,i}$.
2. Calculate $X_i$ as a product of analyte concentrations and affinity constants.
3. Calculate $C_i^d = X/Y_i^d - 1/(1-Y_i^d)$ for each receptor-ligand pair.
4. Calculate the desired number of beads of each type from $N_{B,i}^d C_i^d VN_A/p_{0,i}K_i$.

An Experimental Demonstration—

As described herein, the effective affinity constants can display a substantial length-dependent variation: for example, in the case of Kanamycin, $K_{eff}$ (L=50 nt)/$K_{eff}$ (L=1000 nt)~10 in the concentrated regime. An example of the dramatic effect of the combination of transcript length selection and bead redundancy on assay signal intensity is illustrated in FIG. 18, produced in accordance with the protocols of Example V but using ~3,000 beads for detection of the Kanamycin cDNA, present at 10,000 femtomoles in a reaction volume of 20 ul, and using ~100 beads for detection of the IL-8 cDNA, present at 2 femtomoles in a reaction volume of 20 ul.

Figure 18:
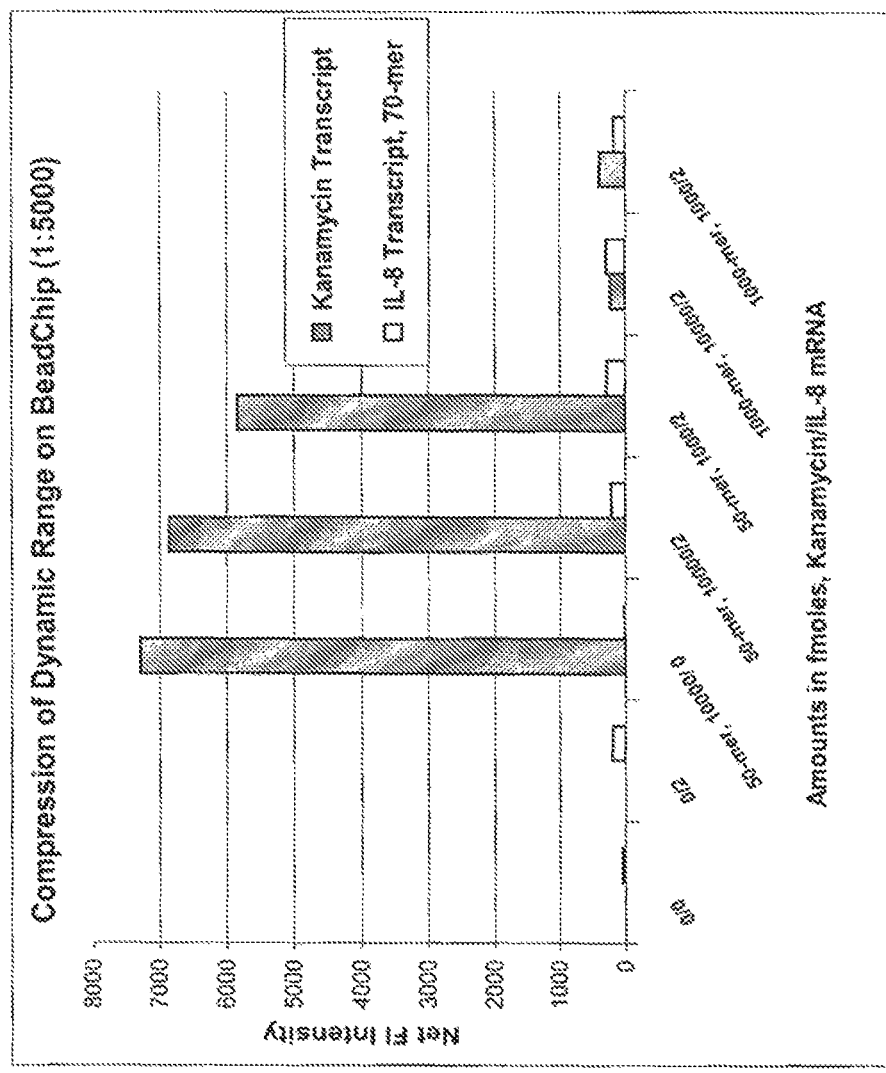
FIG. 18 shows the effect of dynamic range compression produced by optimization of microparticle redundancy, producing, for a 50 nt Kanamycin cDNA and for a 70 nt IL8 cDNA present at concentrations differing in range by a factor of 5,000, a difference in corresponding signal intensities of only a factor of approximately 20.

As depicted in FIG. 18, notwithstanding the fact that, in the fifth and seventh pairs of ratios shown in that figure (counting from the left), the 50 nt and the 1,000 nt Kanamycin transcripts are present at an identical abundance of 1,000 femtomole, the respective signal intensities recorded are seen to differ by more than an order of magnitude. Further, as depicted in FIG. 18, the Kanamycin cDNA, present at approximately 5,000-fold excess over the IL-8 cDNA, produces only an approximately 20-fold higher signal intensity, directly demonstrating dynamic range compression.

Without correction for the substantially differing effective affinity constants of the two transcripts, the analysis of the experimental data would lead to a substantial error in message abundance.

Entanglement—

This particular example illustrates a further effect on signal intensity of captured target which arises from entanglement of target strands in solution. That is, target strands in solution begin to overlap at a certain threshold, t*, in target concentration. For a target containing L nucleotides and assuming a Gaussian coil configuration, the corresponding target concentration is simply $t^* \cong L/R^3 \sim a^{-3}L^{1-3\nu}$, or, with $\nu = \frac{3}{5}$, $t^* \sim L^{-4/5}$, implying, for the target volume fraction, $\phi^* \sim L^{-4/5}$. For targets of appreciable length, $\phi^*$ can be quite small: $\phi^*(L=1,000) \cong 0.004$. In the example, with $a \cong 5A$, $L=1,000$, yields a radius of gyration, $R_{G,T} \cong 9L^{1/2} \cong 9*33A \cong 300A$ and a molecular volume, $V=(4/3)\pi R_{G,T}^3 \cong 300*10^6 A^3$; with $10^3$ fmoles=$10^{12}$ molecules, the volume occupied by target is $V_T \cong 0.3$ µl and hence $\phi=0.3/20 \cong 0.015 > \phi^*$. That is, in the example, the capture efficiency of the 1,000 nt Kanamycin transcript would be expected to be further diminished by target entanglement.

As necessary, an additional measure would be to perform multiple concurrent multiple probe, multiple primer-RT reactions to permit different degrees of initial mRNA dilution. Products would be pooled to perform detection in a single multiplexed reaction.

III.1.3 Differential Amplification—

Because it is governed by an affinity constant that approaches the sequence-dependent affinity constant, $K_{SS}$, the dilute regime of operation generally will be the preferred regime of operation for detection of low-abundance messages. This is so particularly when the design of short cDNAs is difficult or impossible, as discussed herein in connection with the analysis of sets of closely homologous sequences. RT-PCR protocols may devised which limit PCR cycles to a small number, say 3-4, in order to bring the concentration of the lowest-abundance transcripts to the detectable range corresponding to the dilute regime.

Given the reduction in affinity constants in the concentrated regime, transcript amplification to concentrations exceeding the cross-over concentration will yield diminishing returns. That is, for a target of any given length, target amplification may produce a relatively smaller increase in signal in accordance with the length-dependent effective affinities governing transcript capture, particularly in the concentrated regime. Specifically, if high abundance transcripts are amplified into the regime of saturation, additional amplification will not translate into any additional gain in capture and hence detected signal. Unless taken into account in the assay design and the analysis of assay signals, this "saturation" effect can seriously distort the quantitative determination of target concentration.

However, if properly taken into account on the basis of the methods of the present invention, this scenario therefore lends itself to dynamic range compression by differential amplification in which the signal of low abundance messages is enhanced relative to that of high abundance messages undergoing the same number of amplification cycles and in the same multiplexed target amplification reaction.

Pools—

More generally, it may be desirable to equalize the concentrations of transcripts from high and low abundance messages—regardless of target length—within a preset narrow range of concentration. In this instance, it will be useful to split targets into two or more sets undergoing separate multiplexed target amplification reactions in order to be able to subject high abundance messages to a small number of amplification cycles while and to subject low abundance messages to a higher number of amplification cycles.

III.1.4 Labeling Density—

Operation in the dilute regime requires detection of a small number of captured transcripts, and this is facilitated by a high rate of incorporation of labeled dNTPs. In Examples described herein, a typical labeling density of 1:64 is achieved by a molar ratio of one labeled dCTP per eight unlabeled dCTPs. For a 150 nt transcript, this ratio implies $n_{F\,(150\,nt)} \sim 3$, and correspondingly lower numbers for the shorter transcripts present in the mixture. In addition, more label can be added per unit length by adding more than one type of labeled dNTP during reverse transcription. For example, one can use biotin-dATP and biotin-dCTP both in a particular reaction mixture, which generates more label per unit length than either one alone. In an experiment (not shown) labeled biotin-dATP at a ratio of 1:6.25 relative to unlabeled dATP was added as a reagent in a reverse transcription reaction. Comparing to end-labeled cDNA controls, there were about 20 labeled nucleotides present on a 1,000 nucleotide ("nt") Kanamycin cDNA.

More generally, differential labeling also provides a further method of equalizing the signal intensities produced by capture of transcripts differing in concentration. Preferably, this is accomplished by adjusting the number of labels incorporated into sets of transcripts in accordance with the respective known or anticipated levels of abundance as well as length. Preferably, a higher density of labeled dNTPs will be ensured in transcripts exceeding the length limit associated with the cross-over into the concentrated regime. In this instance, a higher labeling density will increase detection sensitivity by compensating for the lower effective affinities of such longer transcripts of which fewer will be captured to anchored probes as discussed herein. The calculation must of course take into account the fact that the average total number of labels per target is proportional to target length.

To accomplish differential labeling of transcripts, RT reactions can be carried out by separating the mRNA sample into two or more aliquots in different tubes (reaction chambers) such that, for example, in one reaction, only short transcripts are generated and in another, only long transcripts are generated and adjusting in each RT reaction the ratio of the labeled dNTPs to unlabeled dNTPs i.e., the higher the ratio, the more label included in the transcript.

III.2 Elongation-mediated Sequence Specific Signal Amplification—

Sensitivity and Specificity—

Results obtained to date using these assay designs to produce short, labeled cDNAs demonstrate sensitivity sufficient to detect—without recourse to mRNA or cDNA amplification but taking advantage of a novel signal amplification method—labeled Kanamycin cDNA fragments, 50 nt-70 nt in length, at the level of one femtomole of material in a total reaction volume of 10 µl (FIG. 19).

Figures 20A, 20B:
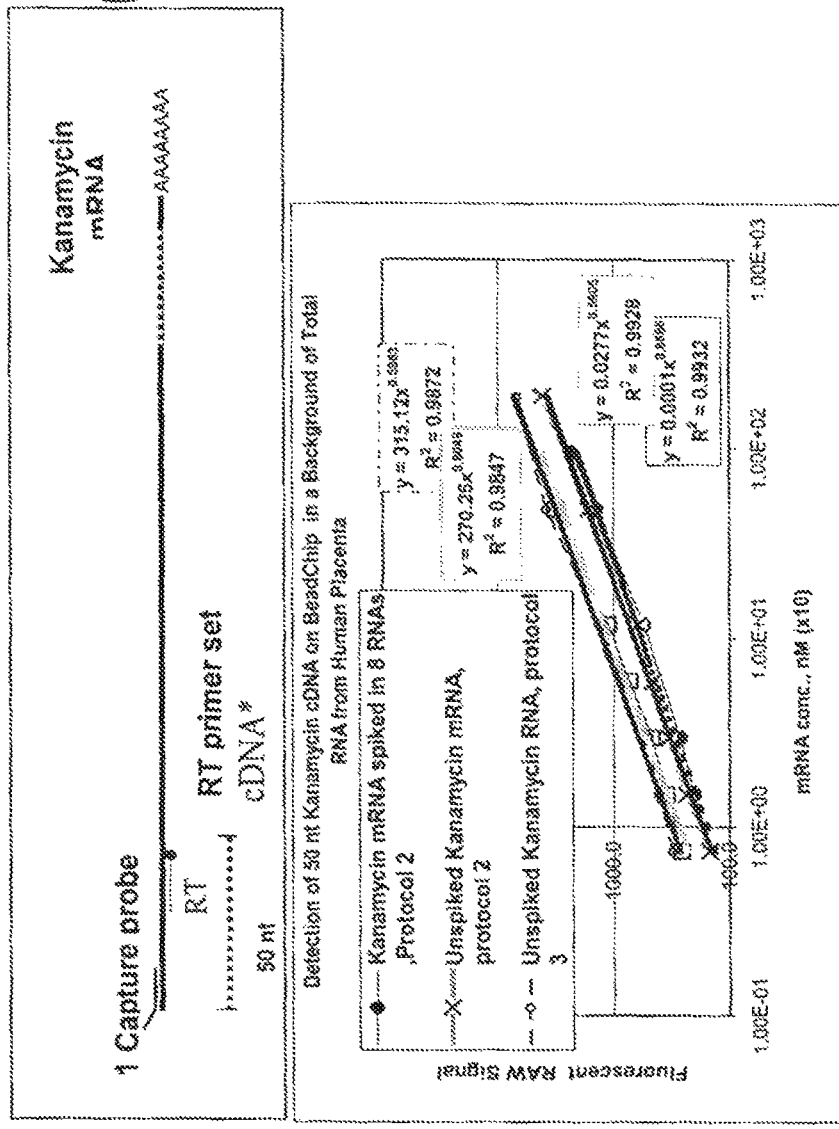
FIG. 20A shows the location of probe and primer in relation to the mRNA target.
FIG. 20B shows a dilution series for a 50 nt cDNA, obtained by reverse transcription of Kanamycin mRNA by several protocols specified herein, including dilution series illustrating the "spiking" of the cDNA into a mixture ("background") of 8 cytokine mRNAs and into a mixture of human placental RNAs.
Figure 21:
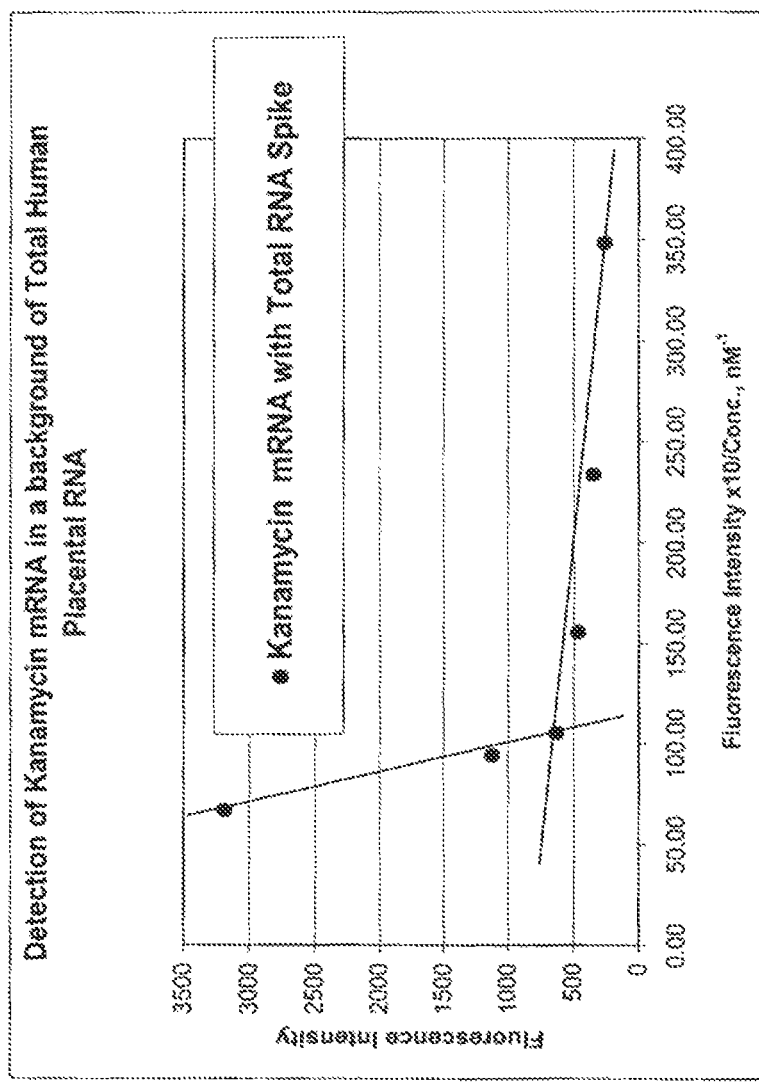
FIG. 21 shows adsorption isotherms in a linearized representation obtained by transformation of dilution series depicted in FIG. 19.

As set forth in Example VI and FIGS. 20, 21, "spiking" experiments can be performed to further evaluate the level of specificity attainable in detecting a specific mRNA in the complex environment typical of a clinical human sample.

Novel Signal Amplification Method—

Figure 22:
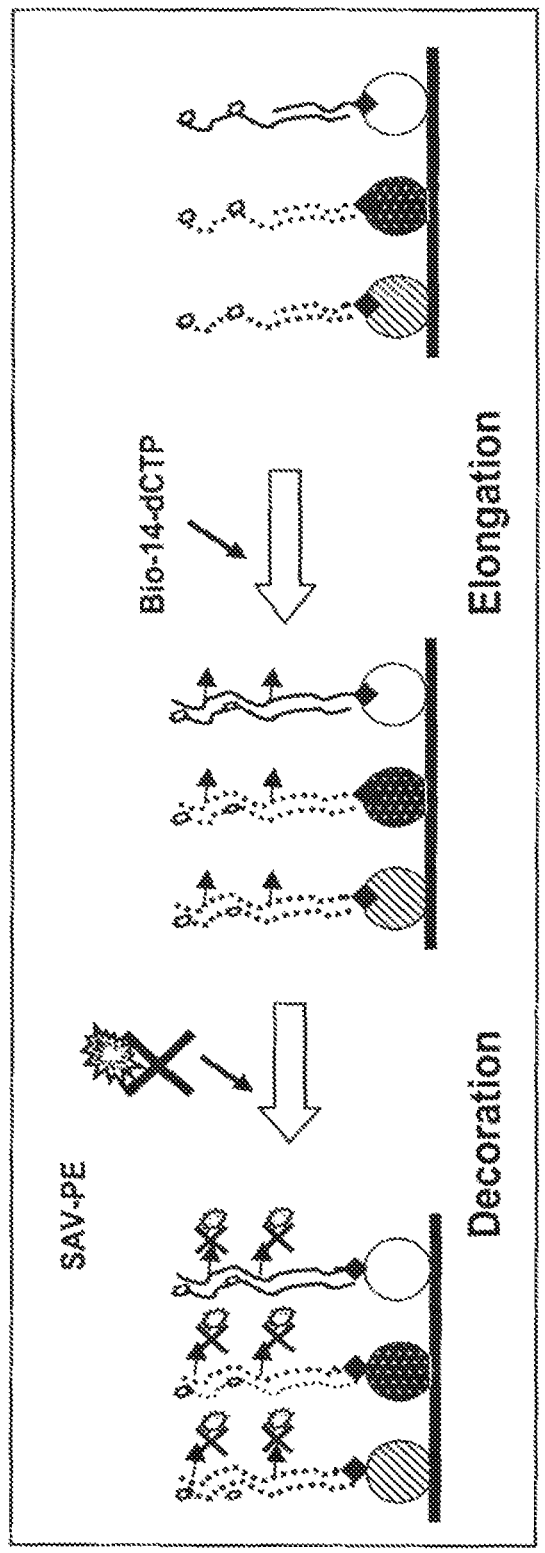
FIG. 22 shows a schematic illustration of a method of signal amplification by enzyme-catalyzed probe elongation and subsequent decoration.

To attain higher sensitivity, a method of (post-assay) signal amplification is disclosed which invokes sequence-specific probe elongation and subsequent decoration with a fluorescent probe to produce an enhancement in signal by an order of magnitude subsequent to cDNA capture. This elongation-mediated process (FIG. 22) takes only a few minutes and can be employed selectively, for example for low abundance messages, in conjunction RT labeling of cDNAs or exclusively, for all messages.

In elongation, the 5' end of the transcript hybridized to the probe is elongated only if there is a perfect match to the probe in this region. See U.S. application Ser. No. 10/271, 602, filed Oct. 15, 2002, entitled; "Multiplexed Analysis of Polymorphic Loci by Concurrent Interrogation and Enzyme-Mediated Detection," incorporated by reference.

First, Kanamycin mRNA (here, in a range of concentrations from 1 to 32 fmoles per 20 ul) is labeled, for example by incorporating Cy3-labeled dCTPs into the cDNA during the RT reaction. The labeled cDNA is captured to immobilized capture probes as described in connection with Examples III, IV and V and FIG. 9. To enhance the signal produced by the captured target, a probe elongation reaction is performed in-situ ("on chip") using biotinylated dCTPs ("Bio-14-dCTP"). The resulting biotinylated elongation product is then "decorated" by exposure to a Streptavidin-Phycoerythrin conjugate, producing substantially enhanced fluorescence from the Phycoerythrin tags (see Example II).

Figure 23:
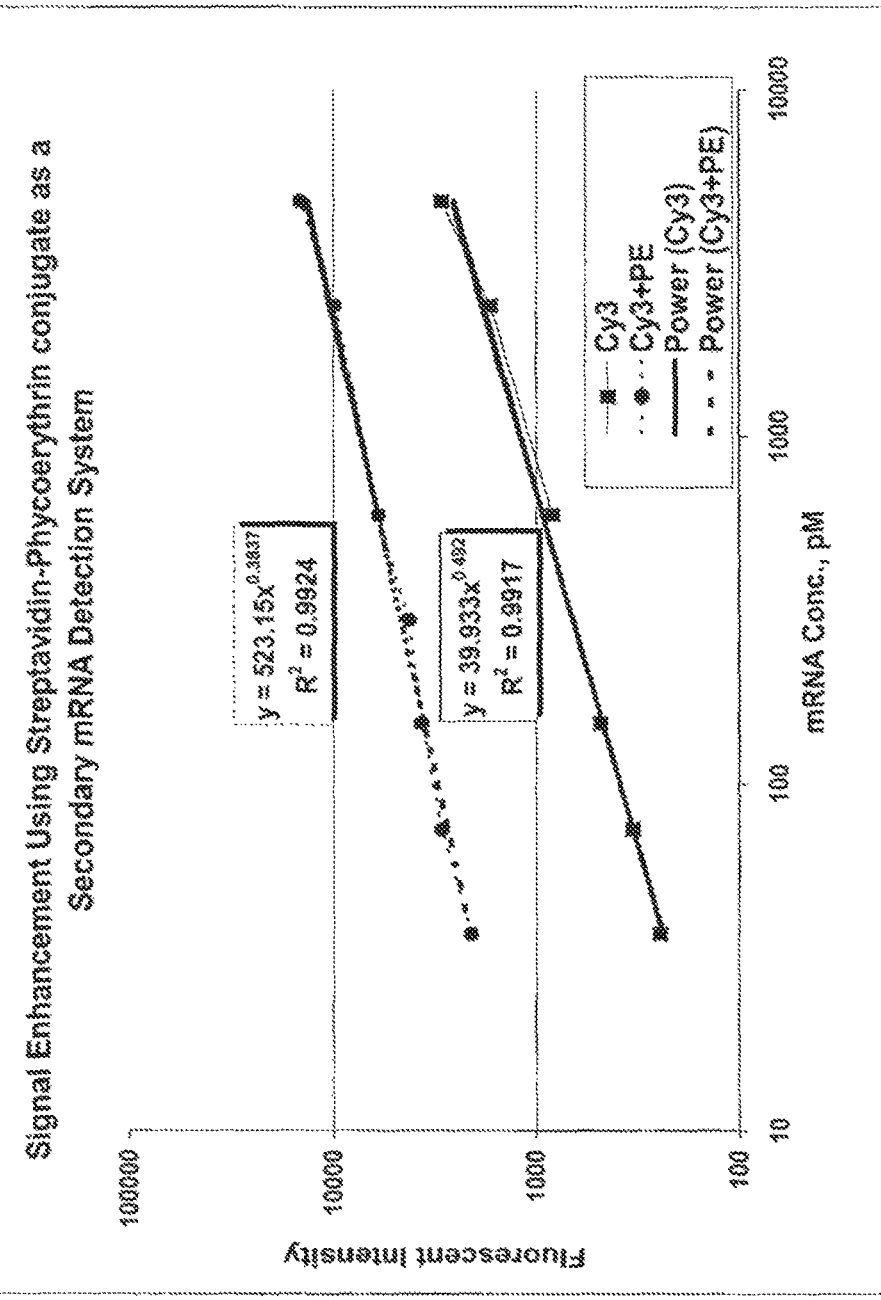
FIG. 23 shows an illustration of the degree of improvement in sensitivity attained by application of the signal amplification method depicted in FIG. 19; the lower plot show signals recorded—in a first color channel—from a labeled Kanamycin cDNA while the upper plot shows signals recorded—in a second color channel—from the same Kanamycin following probe elongation and subsequent decoration.

In fact, as shown in FIG. 23, the reaction is quantitative, producing a 10-fold enhancement over a wide range of concentrations, and thus permitting quantitative determination of message abundance at increased sensitivity, readily permitting the resolution of two-fold changes in intensity over the entire dynamic range in signal of ~3 decades.

Under assay protocols described herein in various Examples, and using an embodiment in accordance with the READ format, the signal produced by capture of 50 nt-70 nt transcripts was readily detected without target amplification (but with signal amplification, as described herein)—at a level of signal to (uncorrected) background of 2:1—at a cDNA concentration of approximately 0.1 fmole per 10 µl of sample. This is sufficient for the detection of mRNA present at a frequency of 10-30 copies per cell, assuming the collection of mRNA from $10^7$ Peripheral Blood Mononucleocytes per ml, as assumed in standard protocols (Lockhart, D. J., Dong, H., Byrne, M. C., Follettie, M. T., Gallo, M. V., Chee, M. S., et al., Nature Biotechnology 14: 1675-1680 (1996)).

III.3 Optimizing Specificity of Detection

The interaction of multiple transcripts with a set of immobilized sequence-specific detection probes is governed by a multiplicity of competing reaction equilibria and a corresponding set of co-affinities. These measure the strength of the interaction between a given probe in the set with all available target subsequences, and between any target subsequence and the set of detection probes. Interactions of a given target with any but its "cognate" capture probe has the potential to generate unwanted interference in the multiconstituent probe-target reaction kinetics and equilibria.

III.3.1. Optimizing Primer and Probe Selection

The risk of cross-reaction increases with transcript length and also increases with the number of transcripts in the reaction because the conditional probability of encountering a second subsequence which approximates a given first ("cognate") subsequence increases with the total length of available target sequence. To enhance specificity of capture, several references of the prior art describe a strategy of "multi-dentate" capture using two or more probes directed to each anticipated target. However, in a multiplexed format of quantitative analysis, this strategy generally is not advisable, given that it not only increases the complexity of the probe array design but also increases the risk of cross-reactivity with each added probe.

In order to minimize cross-reactivity, it is therefore preferable to produce short transcripts by judicious placement of sequence-specific RT primers close to the 3' end of the mRNA. Other aspects of assay design relating to certain entropic effects described herein likewise lead to this preference. Accordingly, the assay design techniques described herein are practiced by optimizing the selection of sequence specific RT primers as well as sequence-specific detection probes, preferably in accordance with the methods of Application Ser. No. 60/487,451, supra.

The methods of the present invention take advantage of the a priori knowledge of the sequences and anticipated levels of abundance of the designated mRNAs of interest to select and place RT primers in specific regions of each mRNA in order to control the length and degree of labeling of the cDNA produced in the RT reaction. In some cases, it will be advantageous to place multiple RT primers on one or several of the mRNAs in the designated set and to analyze the corresponding cDNAs using multiple probes directed against different subsequences of these cDNAs. This is referred to herein as "Multiple Primer Multiple Probe" (mpmp) design, as described in Application 60/487,451, supra. In some situations, it will be advantageous to perform the further step of amplifying the reverse transcripts prior to detection.

These methods of the invention relating to optimization of specificity are useful in numerous applications, exemplified by those in Example VII. They also were applied to the multiplexed analysis of a set of cytokine genes, described in detail in Example VIII and related FIGS. 24A, 24B.

III.3.2. Enhancing Specificity by MultiProbe Detection Combining hMAP and eMAP—

Another assay format of the invention is useful to detect members of gene families where the members of the families have subsequences, in relatively close proximity, of both: (i) significant differences in sequence, such as an insert of 3-or more nucleotides in some members, and (ii) substantial sequence homology, but with minor differences such as single nucleotide polymorphisms (SNPs). Because of the substantial sequence similarity, such sequences can be difficult to distinguish with a conventional hybridization assay given the substantial cross-hybridization.

To solve the problems posed by cross-hybridization, and reduce the cost, the members of the family can be discriminated, and respective abundances determined, by performing a combination of elongation and hybridization in a dual assay format, in which some probes hybridize to the transcripts representing regions with large differences, and other probes hybridize to the transcripts representing regions with small differences, wherein only the latter transcripts are detected using an elongation reaction. By a particular analysis of the results, the family members can be detected. That is, small differences between otherwise homologous sequences preferably are detected by performing a sequence-specific elongation reaction, thereby ensuring identification of members of a gene family while simultaneously using either the elongation reaction itself for the quantitative determination of message abundances (see III.2) or combining elongation with hybridization to ensure discrimination and quantitation.

In the simplest example, one has a family of members having one region of significant sequence differences (a section of 3 added bases) and one region with one SNP. Using the format described above, one would use four beads and two different transcript labels. As illustrated in FIG. 25B, one bead has probe attached (hybridizing to region $P_1$, which contains the added three bases), another coded bead has $hP_2$ probe attached (hybridizing to corresponding region $P_2$, which does not contain the 3 added bases). A third bead has probe $eP_1$ attached (hybridizing to region $eP_1$, which has normal allele, and the fourth bead has probe $eP_2$ attached (hybridizing to corresponding region $eP_2$, which has a variant allele). The 5' terminal end of each transcript is labeled with a first color ("red") by using an appropriately labeled primer during reverse transcription. If a transcript hybridized by the eP1 or eP2 probes is elongated following hybridization, the elongation product is labeled by using extending nucleotides (dNTP or ddNTP) labeled with a second color ("green").

Following hybridization of a sample, one can analyze the array. Where red appears on beads $hP_1$ or $hP_2$, this indicates that the presence of to region $P_1$ or $P_2$, respectively, in the transcript. Where the transcript on the $eP_1$ bead is elongated, as detected from the green label, this indicates capture of the eP$_1$ normal ("wild type") allele, and where the eP$_2$ bead displays green, this indicates capture of the eP$_2$ variant allele. Accordingly, one can readily detect the presence of transcripts with both regions, using only one elongation reaction, by analyzing patterns of hybridization and elongation. Families of mRNAs with more complex patterns of differences could be analyzed in the same manner, using the appropriate numbers of encoded beads and hybridization and elongation reactions.

III.3.2A. Concurrently Determining Expression Levels and Class of AU-Rich mRNAs

Messenger RNA (mRNA) turnover is involved in the transient response to infection and stress. In mammalian cells, most mRNAs undergo poly(A) shortening as the initial step in their decay. Adenylate uridylate (AU)-rich elements in 3'-untranslated regions (UTR) of mRNA is involved in effectively destabilizing mRNA molecules. Many mRNAs containing an AU-rich element (ARE) are highly expressed in disease states, and may function in selectively boosting or inhibiting gene expression during disease response. The core pentameric sequence of the ARE motif is AUUUA. AREs may contain several copies of dispersed AUUUA motifs, often coupled with nearby U-rich sequences or U stretches. A number of classes of AREs are currently known.

The method herein permits discriminating among the classes of AREs associated with particular unique mRNA subsequences, using probes which can detect the different unique subsequences but which can be labeled with a dye of one color (as opposed to needing multiple colors), and also of determining relative expression levels of unique mRNA subsequences associated with AREs. In this method, one first attaches several of types of probes to encoded beads, where each beads' encoding correlates with the probe-type attached. The probes are selected to hybridize to cDNA regions which are complementary to unique mRNA subsequences upstream of AREs and poly A tails. Samples of mRNA are reverse transcribed to cDNA using primers selected so as to reverse transcribe the ARE as well as the unique mRNA susequence upstream, and the transcripts are labeled and contacted with the probes on the beads under hybridizing conditions.

Following hybridization, as a step in quantitating the relative gene expression, one takes an assay image to show the labeled transcript associated with each encoded bead, and provide an overall image of the labeled transcript in the array. As a step in discriminating among ARE classes, the probes on the beads which have hybridized with a cDNA are elongated under conditions whereby the newly elongated product (which is attached to an encoded bead) will include a portion corresponding to the ARE. This is done by adding all four types of dNTPs in large excess, so that a relatively long probe elongation can take place. An assay image is then recorded for identification of the probe/transcript type on different beads.

Figure 26:
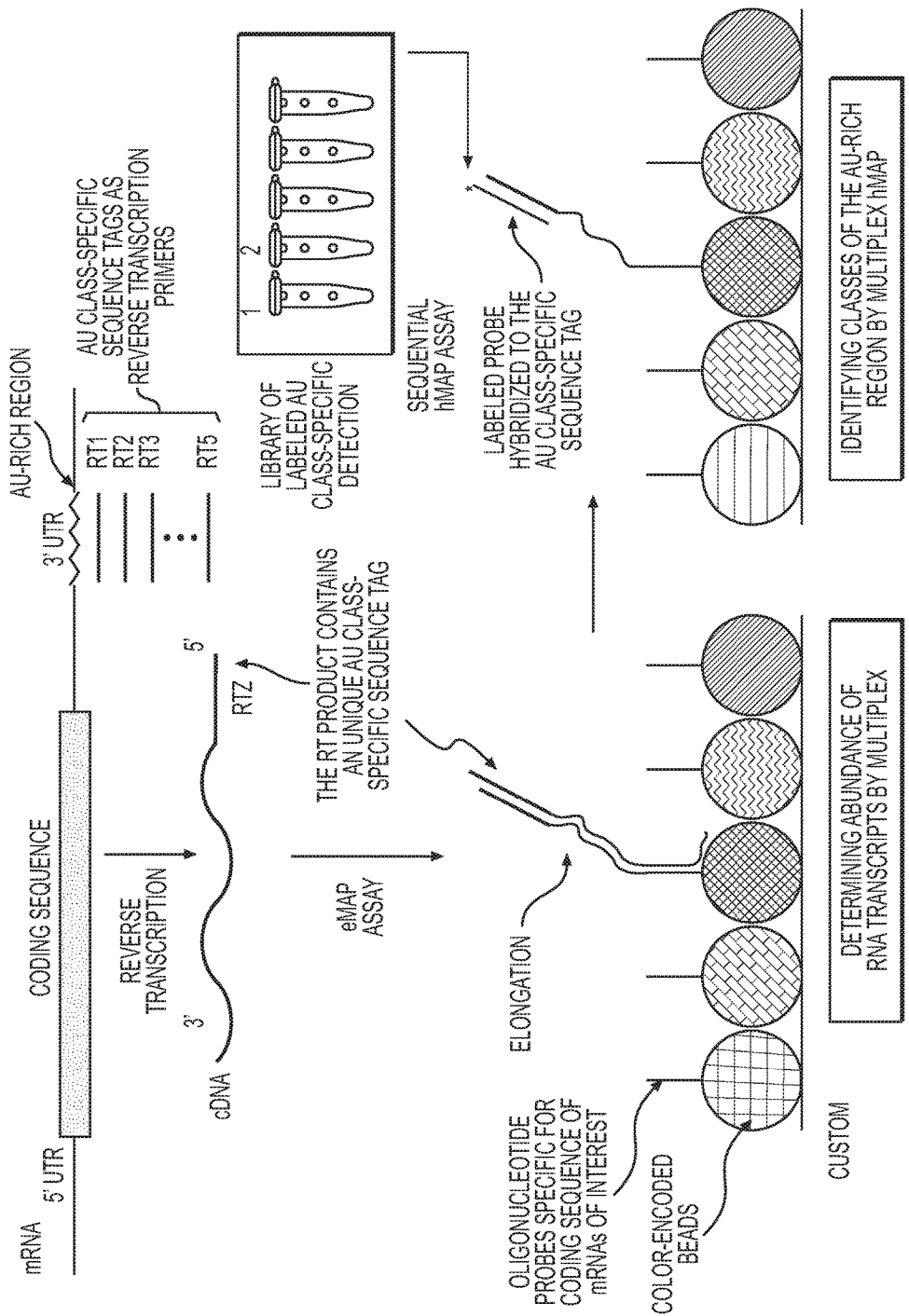
FIG. 26 shows a procedure for the combined quantitative determination of the concentration, and the identification of the specific class of, AU-rich mRNA sequences.

The transcript is then denatured from the elongated probe, for example by heating, and the bead/probe is contacted, in sequence, with labeled probes of one sequence, from a library of probes complementary to various classes of AREs. These "ARE probes" can all be labeled with the same dye, because they are used in succession, rather than being added to the same assay mixture. Upon decoding, following hybridizing the ARE probes, the ARE class which is associated with each bead, and therefore each unique gene sequence, can be determined. The process is shown schematically in FIG. 26.

The relative expression level of the unique gene sequences in vivo can be determined at various points in time, based on the relative signal from the labeled transcripts as determined at such points in time. Such a determination can be useful in monitoring whether certain gene sequences associated with AREs, and thus often with disease conditions, are up or down regulated over time.

III.3.2B. Discrimination of Closely Homologous Sequences: Inbred Strains of Maize Certain applications such as those discussed herein in greater detail call for the detection of specific targets within an ensemble of hundreds or thousands of targets displaying substantial sequence homology with the target(s) of interest. These circumstances generally will require a degree of sequence-specificity beyond that afforded by hybridization. Certain aspects relating to the selection of suitable primer and probe sets are discussed in detail in provisional application Ser. No. 60/487,451, supra. Here we disclose several specific array designs and assay protocols which invoke combinations of sequence-specific sequence conversion by reverse transcription and/or amplification as well as multiplexed detection by hybridization (hMAP) and/or elongation (eMAP). Several specific instances are now described to illustrate these assay designs and methodologies of the present invention.

Interrogation of Elongation Products using Hybridization Probes—

Another assay format of the invention is useful to detect closely homologous members of gene families by a sequence of elongation-mediated detection to discriminate a first subset of genes from a second subset of genes, only the first subset being capable of forming an elongation product which may be detected by incorporating therein a detection label of a first color. Members within the first set may then be further discriminated by the identification of a specific subsequence in the elongation product, this identification involving a hybridization probe modified with a detection label of a second color. Details of this method, previously disclosed in connection with "phasing" of polymorphisms are described in pending U.S. application Ser. No. 10/271, 602, filed Oct. 15, 2002, entitled: "Multiplexed Analysis of Polymorphic Loci by Concurrent Interrogation and Enzyme-Mediated Detection," and are further described in Example IX with reference to FIGS. 27-29 (the DNA sequence in FIG. 27 is SEQ ID NO. 12; the he DNA sequence in FIG. 28 is SEQ ID NO. 13).

III.4 Subtractive Differential Analysis Using Single Color Detection

Figure 30:
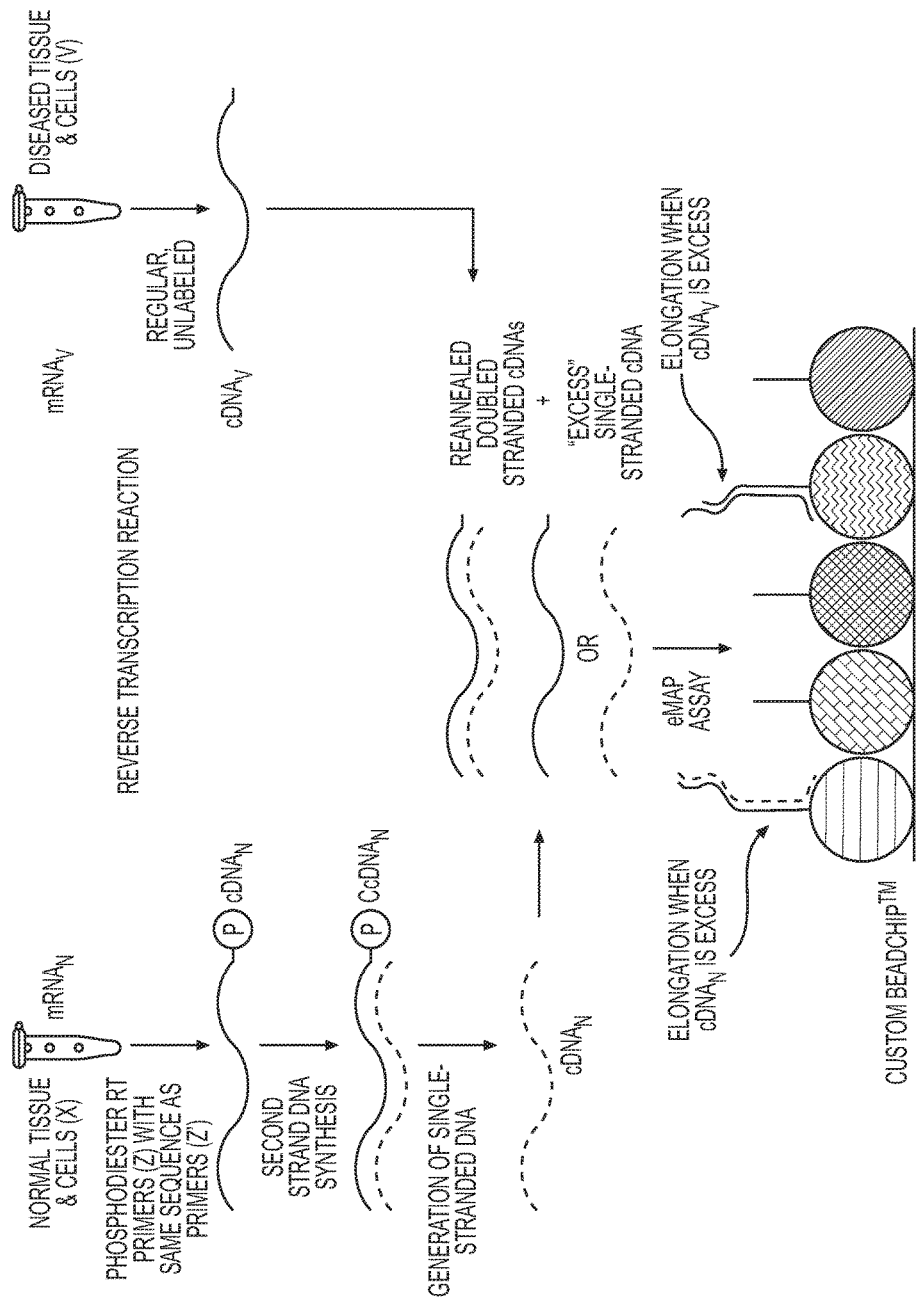
FIG. 30 shows a procedure of subtractive differential gene expression analysis employing one detection color.

In one particular assay format of the invention, subtractive hybridization is used to determine differential expression of different mRNAs (FIG. 30). This is useful, for example, in diagnosis of certain diseases and conditions, where corresponding mRNA levels that differ between diseased and healthy subjects. In this assay format, designated mRNAs are extracted from healthy ("normal", N) and diseased ("variant", V) subjects and are equalized to ensure equal mRNA concentrations in both samples. This is accomplished, for example, by inclusion of common reference mRNAs in both samples.

In both samples, mRNAs are first reverse transcribed to produce sense cDNAs, respectively denoted cDNA$_N$ and cDNA$_V$. The RT primer used for reverse transcription of one, but not the other sample, is modified with a tag permitting subsequent strand selection. Following reverse transcription, the sample containing the tagged primer, say the normal sample, is transcribed to produce ccDNA$_N$, that is, a strand of DNA that is complementary to cDNA$_N$; the latter is enzymatically digested.

Next, $cDNA_V$ and $ccDNA_N$ are combined under conditions permitting the annealing of these mutually complementary single strands to form a duplex. This step removes ("subtracts") that amount of DNA that is equal in both samples. Underexpression of one or more designated genes in the V-sample leaves the corresponding excess in the N-sample, and conversely, overexpression of one or more designated genes in the V-sample leaves the corresponding excess in the V-sample. The excess of single stranded DNA is detected using pairs of encoded "sense" and "antisense" probes, one matching $cDNA_V$ the other matching $ccDNA_N$. Preferably, sets of sense and anti-sense probes are displayed on encoded microparticles ("beads") forming a random encoded array.

The combined sample is placed in contact with the set of sense and antisense probes and hybridized transcripts are detected, for example, by recording from the set of beads fluorescence signals produced by captured transcripts which may be fluorescently labeled by incorporation of fluorescent RT primers or by incorporation of labeled dNTPs. For each pair of sense and antisense probes, the difference in the intensities indicates the sign and amount of the excess in the corresponding transcript. Significantly, in contrast to standard methods of ratio analysis, only a single color is required here.

IV. Generic Disclosure

Random Encoded Array Detection (READ)—

The method of multiplexed quantitative detection preferably employs an array of oligonucleotide probes displayed on encoded microparticles ("beads") which, upon decoding, identify the particular probe displayed on each type of encoded bead. Preferably, sets of encoded beads are arranged in the form of a random planar array of encoded microparticles on a planar substrate permitting examination and analysis by microscopy. Intensity is monitored to indicate the quantity of target bound per bead. The labels associated with encoded beads and the labels associated with the transcripts bound to the probes in the array are preferably fluorescent, and can be distinguished using filters which permit discrimination among different hues. This assay format is explained in further detail in U.S. application Ser. No. 10/204,799, filed Aug. 23, 2002, entitled: "Multianalyte molecular analysis using application-specific random particle arrays," hereby incorporated by reference.

Libraries of Probe-Functionalized Encoded Microparticles ("Beads")—

The particles, to which the probes are attached may be composed of, for example, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. (See, e.g., "Microsphere Detection Guide" from Bangs Laboratories, Fishers, Ind.). The particles need not be spherical and may be porous. The particle sizes may range from nanometers (e.g., 100 nm) to millimeters (e.g., 1 mm), with particles from about 0.2 micron to about 200 microns being preferred, with particles from about 0.5 to about 5 microns being more preferred.

Particles are encoded so as to be correlated with the sequence-specific bead-displayed probes that are placed on the surface of the particles by a chemically or physically distinguishable characteristic, for example fluorescence, uniquely identifying the particle. Chemical, optical, or physical characteristics may be provided, for example, by staining beads with sets of optically distinguishable tags, such as those containing one or more fluorophore or chromophore dyes spectrally distinguishable by excitation wavelength, emission wavelength, excited-state lifetime or emission intensity. The optically distinguishable tags may be used to stain beads in specified ratios, as disclosed, for example, in Fulwyler, U.S. Pat. No. 4,717,655. Staining may also be accomplished by swelling particles in accordance with methods known to those skilled in the art, (See, e.g., Molday, Dreyer, Rembaum & Yen, J. Mol Biol 64, 75-88 (1975); L. Bangs, "Uniform latex Particles, Seragen Diagnostics, 1984). Using these techniques, up to twelve types of beads were encoded by swelling and bulk staining with two colors, each individually in four intensity levels, and mixed in four nominal molar ratios. Alternatively, the methods of combinatorial color encoding described in International Application No. PCT/US 98/10719 (incorporated herein by reference) may be used to endow the bead arrays with optically distinguishable tags.

Probes—

A set of sequence-specific probes, known as a "capture probe set", is used in the assay. Each member of a capture probe set is designed—preferably using methods of the co-pending provisional application entitled "Hybridization-Mediated Analysis of Polymorphisms (hMAP)," filed May 17, 2004, Ser. No. 10/847,046—to have a unique complementary region with one "cognate" cDNA target molecule. As explained above, the length of the complementary region of each member of a capture probe set may be different in order to tailor the binding affinity.

These oligonucleotide probes may be synthesized to include, at the 5' end, a biotinylated TEG spacer for attachment to microparticles functionalized by attachment of Neutravidin, or an aminated TEG spacer (Synthegen TX) for covalent attachment to the functionalized surface of particles, using carboxylated beads and an EDAC reaction.

Reverse Transcription—

The total RNA used for these assays is isolated and reverse transcribed to cDNA, and the cDNA molecules are added in the presence of a solution containing dNTPs, or ddNTPS, and DNA polymerase to elongate the cDNA on those probes on which the 5' end of the target and the complementary sequence on the probe are perfectly matched. The dNTP/ddNTP mixture contains at least one labeled dNTP or ddNTP, in order to incorporate fluorescent label in the elongated target. The cDNA target molecules of the assay are fluorescently labeled as described herein, and the density of the fluorescently labeling (e.g., the degree of incorporation of fluorescently labeled dNTPs) of the cDNA target molecules may vary, depending on whether the expression level of the corresponding mRNA is expected to be high or low. In addition, the region the probe binds to on the transcript affects the hybridization pattern; i.e., it is easier for probes to bind to the ends. Details are described in several Examples below.

Methods of Array Assembly—

To produce a custom array containing a specific probe combination, the encoded, probe-decorated beads are pooled together and assembled into arrays. Many different methods of assembling arrays are possible, including a technique known as LEAPS™ (Light-Controlled Electrokinetic Assembly of Particles Near Surfaces, described in U.S. Pat. No. 6,251,691 which is hereby incorporated by reference). In LEAPS™, the bead arrays are prepared by first providing a planar electrode that is substantially parallel to a second planar electrode (in a "sandwich" configuration), with the two electrodes being separated by a gap, where in the gap is a polarizable liquid medium, such as an electrolyte solution. The surface or the interior of the second planar electrode is patterned to create areas of lowered impedance. The beads are then introduced into the gap. When an AC voltage is applied to the gap, the beads form a random encoded array on the second electrode, in accordance with the patterning, or, in the alternative, in accordance with an illumination pattern on the second electrode. The resulting arrays can exhibit a very high feature density. Alternative methods of assembly of particle arrays are described in U.S. application Ser. No. 10/192,352, filed Jul. 9, 2002, entitled: "Arrays of Microparticles and Methods of Preparation Thereof."

Decoding Image—

In an assay of the invention, the population of particles is encoded with a distinct chemical or physical characteristic that allows the type of particle to be determined before and after the assay. For decoding, a decoding image of the assembled array is taken, prior to the assay or subsequent to the assay, to record the spatial distribution of encoded particles in the array and hence the spatial distribution of the members of the capture probe set.

Optical Signatures and Assay Images—

To facilitate detection of captured targets, cDNA molecules are fluorescently labeled by incorporation, during reverse transcription, of labeled dNTPs at a preset molar ratio, the total amount of incorporated dNTP varying with the length of the (reverse) transcript. Instead of, or in addition to, hybridization-mediated capture, the assays of the invention also include elongation-mediated detection; cDNA molecules are added in the presence of a solution containing dNTPs, or ddNTPS, and DNA polymerase to elongate the cDNA on those probes whose 3' end is complementary to the captured target. The dNTP/ddNTP mixture contains at least one labeled dNTP or ddNTP, in order to incorporate fluorescent label in the elongated probe.

The labels associated with the encoded beads and the labels associated with the transcripts bound to the probes in the array are preferably fluorescent, and can be distinguished using filter combinations which permit discrimination among different excitation and emission wavelengths and hence combinations of base colors that are combined in multiple combinations. In accordance with the preferred embodiment of READ, beads are assembled into planar arrays that can be readily examined and analyzed using, for example, a microscope. The intensity of an optical signature produced in the course of catering and analyzing targets is monitored to indicate the quantity of captured target.

Recording of Decoding and Assay Images—

A fluorescence microscope is used to decode particles in the array and to detect assay signals from the array of probe-captured cDNA molecules. The fluorescence filter sets in the decoder are designed to distinguish fluorescence produced by encoding dyes used to stain particles, whereas other filter sets are designed to distinguish assay signals produced by the dyes associated with the transcripts/amplicons. A CCD camera may be incorporated into the system for recording of decoding and assay images. The assay image is analyzed to determine the identity of each of the captured targets by correlating the spatial distribution of signals in the assay image with the spatial distribution of the corresponding encoded particles in the array.

Assay—

Either prior to, or subsequent to decoding, the array of encoded particles is exposed to the cDNA target molecules under conditions permitting capture to particle-displayed probes. After a reaction time, the array of encoded particles is washed with 1×TMAC to remove remaining free and weakly annealed cDNA target molecules. Instead of or in addition to hybridization assays, the assays of the invention include elongation-based detection.

An assay image of the array is then taken to record the optical signal of the probe-cDNA complexes of the array. Because each type of particle is uniquely associated with a sequence-specific probe, combination of the assay image with the decoding image, recorded, for example, prior to performing the assay, permits the identification of annealed cDNA molecules whose respective abundances—relating directly to the abundances of the corresponding original mRNA messages—are determined from the fluorescence intensities of each type of particle.

The examples below provide further details regarding the making and using of the invention.

Example I: Effect of Probe and Transcript Length on Capture Efficiency

Synthetic DNA polynucleotide targets varying in length from 25-mers to 175-mers, were synthesized (by IDT, Madison, Wis.), and each of the larger targets contained the smaller target as an interior subsequence. All the targets were labeled with Cy5 fluorescent label at the 5' end. Amine-modified (5' end) oligonucleotide probes, varying in length from 15 nt to 35 nt, were also synthesized (IDT, Madison, Wis.). The detailed sequence information is shown in Table I-1.

The probes were covalently linked to encoded tosylated microparticles using an EDAC reaction, as is well known in the art. A precalculated amount of each of the synthetic targets was taken from a 10 µM stock solution of the target in de-ionized water, and was diluted with 1×TMAC (4.5 M tetramethyl ammonium chloride, 75 mM Tris pH 8.0, 3 mM EDTA, 0.15% SDS) to a desired final concentration. One or more of the probe types listed in Table I-1 were functionalized with fluorescent microparticles and were then assembled into planar arrays on silicon substrates. Twenty microliters of the synthetic target was added to the substrate surface and the substrate was placed in a 55° C. heater for 20 minutes. The slide was then removed from the heater and the target solution was aspirated. The substrate was washed thrice with 1×TMAC at room temperature. Following this, 10 µl of 1×TMAC was placed on the substrate surface, covered with a glass cover-slip and the fluorescence intensity of the array was recorded. FIGS. 3, 5, 6 and 7 show the results obtained from these hybridization experiments.

Figure 4:
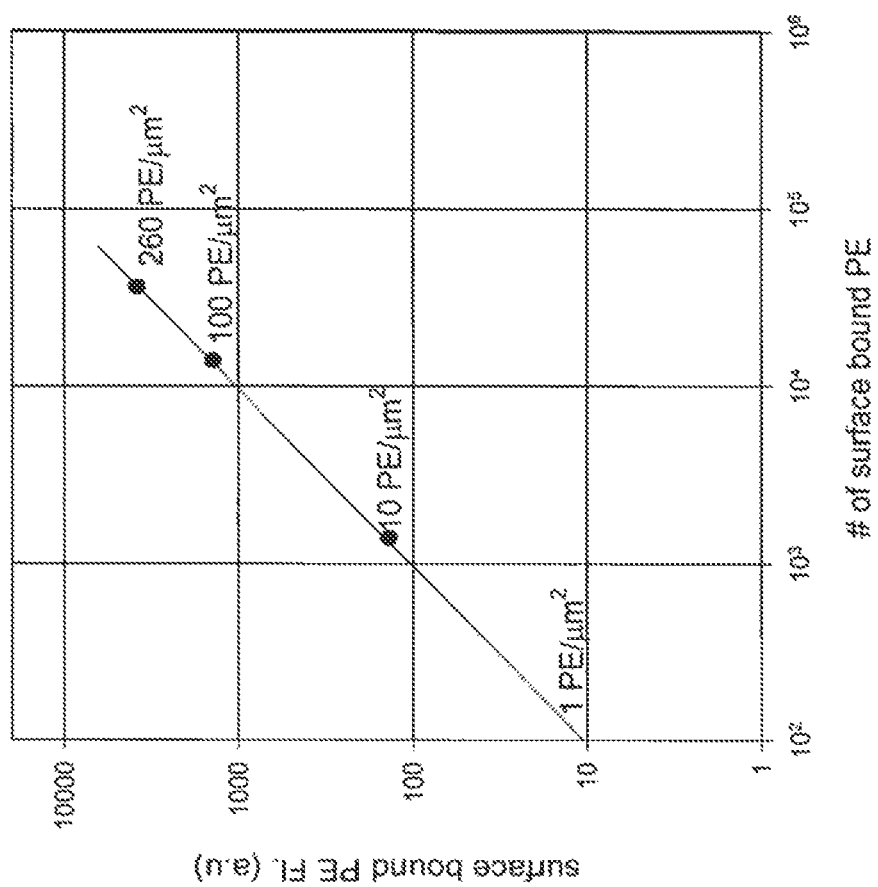
FIG. 4 shows a calibration curve for conversion between intensity and concentration of fluorophores displayed on microparticle surfaces.

Example II: Determination of the Absolute Number of Fluorophores Present Per Particle Experiments were performed with commercially available QuantiBRITE™ PE Phycoerythrin Fluorescence Quantitation kit from Becton-Dickinson, Franklin Lakes, N.J. The kit consists of 6.6 µm polymer beads, conjugated with known number of Phycoerythrin (PE) molecules on the surface. For quantitative analysis of the fluorescent intensity associated with the beads, random planar arrays of the beads were assembled on the surface of a silicon wafer. The fluorescent intensity from the PE fluorophores on the particle surface was then monitored as a function of varying number of surface conjugated PE fluorophores (data supplied by manufacturer) using a standard fluorescent microscope fitted with an appropriate fluorescence filter and a CCD camera. In this study, a Nikon Eclipse E-600FN epifluorescence microscope equipped with 150 W xenon-arc lamp was used for measurements. A Nikon 20×0.75 NA air objective, and a R&B PE Filter cube (Chroma Technology Corp., Battleboro, Vt.) was used for the measurements. Images were recorded with a cooled 16 bit CCD camera (Apogee Instruments Inc.). The exposure/integration time for the experiment was 500 ms. User interfaced programs for collection and analysis of images were developed using MATLAB™ which was run on a PC. The results are shown in FIG. 4, from which it can be seen that ~100 PE molecules/particle (i.e. 1 PE molecules/µm$^2$) can be detected using this system.

The fluorescent properties of R-phycoerythrin and 2 common CY dyes are compared in the following Table I-3.

TABLE I-3

| Name | Abs. Max. (nm) | Em. Max. (nm) | Ext. Coeff. (M$^{-1}$cm$^{-1}$) | QY for protein conjugates | Mol. Wt. (dye) |
|---|---|---|---|---|---|
| R-phycoerythrin | 480 546 565 | 578 | 1,960,000 | 0.82 | 240,000 |
| Cy3 | 550 | 570 | 150,000 | 0.16 | 766 |
| Cy5 | 649 | 670 | 250,000 | 0.28 | 792 |

Hence one PE molecule is equivalent to ~60 Cy3 molecules or ~20 Cy5 molecules. Accordingly, the anticipated detection threshold for the Cy3 is ~60 molecules/um$^2$ and for Cy5~20 molecules/um$^2$. A 2 um particle has a surface area of ~12.5 um$^2$ and would hence need 750 molecules of Cy3/particle for detection and 250 molecules of Cy5/particle for detection. The corresponding numbers for a 3 micron particle are 1700 for Cy3 and 600 for Cy5. Hence, a conservative estimate of the detection sensitivity using Cy dyes (for 2-3 micron particles) is ~1000 fluorophores/particle.

In the same way as discussed above the slope of the curve can also be used as an approximate conversion factor (when using dyes other than PE) for converting recorded raw intensities back to number of molecules/um$^2$ and with the knowledge of the bead size, then to the number of fluorophores/bead.

Example III: Generic Protocol for Rapid Expression Monitoring

A typical experimental protocol for multiplexed expression monitoring is as follows. A protocol establishing optimized conditions in accordance with the methods of the present invention is described below. The entire protocol including signal amplification in accordance with the methods of the present invention is completed in less than three hours (see FIGS. 1 and 2).

Step 1—

Total RNA is isolated from a blood or tissue sample using Qiagen silica-gel-membrane technology. DNA oligonucleotides with a sequence complementary to that of mRNAs of interest are added to the preparation to prime the reverse transcription of the targeted mRNAs into cDNAs.

Step 2—

The solution containing mRNAs is heated to 65° C., typically for a period of 5 minutes, to facilitate annealing of primers to denatured mRNAs, following which the solution is gradually cooled to room temperature at a typical rate of 2° C./min. Reverse transcriptase (for example Superscript III, Contech) along with fluorescently labeled dNTPs (at a typical molar ratio of 1:8, labeled to unlabeled dCTP) are added to initiate the RT reaction. After synthesis of labeled cDNAs, RNA templates are digested using RNase.

Step 3—

Fluorescently labeled cDNAs are permitted to anneal, in 1×TMAC buffer at 50° C. for 30 minutes, to arrays of color-encoded microparticles displaying DNA oligonucleotide capture probes on silicon chips (FIG. 9) in accordance with the READ format. Hybridization was followed by three consecutive steps of washing in 1×TMAC buffer, each step requiring only the exchange of buffer.

As necessary, signal amplification in accordance with the methods of the present invention may be performed as described herein.

Capture probe sequences are designed to be complementary to the 3' regions of individual cDNAs in the mixture. The optimization of capture probe sequences for use in the multiplexed analysis of cDNAs is described in greater detail in the co-pending application Ser. No. 10/892,514 entitled: "Concurrent Optimization in Selection of Primer and Capture Probe Sets for Nucleic Acid Analysis," filed Jul. 15, 2003. Arrays are prepared as described herein. Step 4—The resulting pattern of fluorescence is recorded in the form of a fluorescence image by instant imaging (typically using integration times less than 1 second) on an automated Array Imaging System as described in greater detail in U.S. provisional application Ser. No. 10/714,203 entitled: "Analysis, Secure Access to, and Transmission of Array Images" filed Nov. 14, 2003. Manually operated fluorescence microscopy also may be used. From the assay image quantitative intensities are determined by analysis of the assay image as described herein and described in greater detail in the Ser. No. 10/714,203.

Example IV: Analysis of Kanamycin mRNA (Using Protocol of Example III)

Example IVA: mpmp-RT Design and Transcript Labeling

An mpmp-RT design comprising six Cy3-modified RT primers and multiple microparticle-displayed capture probes was used, in a single reaction for each of a series of solutions of successively lower Kanamycin concentrations, in accordance with a 1:2 serial dilution. A mixture of fragments varying from 79 nt to 150 nt in size, incorporating into each fragment Cy-3 modified dCTP at an average molar ratio of 1:16 of labeled to unlabeled dCTP and hence at an average labeling density of 1:64, was produced.

Example IVB: Transcript Length and Improved RT Design

Using an mpmp-RT design comprising either one or two Cy3-modified RT primers and microparticle-displayed capture probes, RT reactions were performed on each of a series of Kanamycin mRNA solutions of successively lower concentrations, spanning a range from 25 nM to ~50 pM. Specifically, three combinations of RT primers and capture probes were tested to produce and analyze cDNA fragments of 70 nt and/or 50 nt in size. The Cy3 labeling density of the transcripts was also doubled—from 1:64 to 1:32—by incorporating into each fragment Cy-3 modified dCTP at an average molar ratio of 1:8 of labeled to unlabeled dCTP. Using Cy3-labeled RT primers, each 50 nt transcript will on average contain 2-3 Cy3 labels.

Example IVC: Optimization of Assay in Titration of Model mRNA

Having established target configurational entropy as a critical factor affecting the sensitivity of cDNA detection, it was then confirmed in several assay designs that a further reduction in transcript length from 150 nt to ~50 nt, along with a doubling of the Cy3 labeling density of transcripts obtained from a 1,200 nt Kanamycin model mRNA, produced a further enhancement in assay signal by the anticipated factor of ~5, corresponding to a detection limit of ~50 pM.

Significantly, closely comparable results—including the critical role of target entropy—were obtained with a mixture of 8 unknown mRNAs into which the Kanamycin mRNA was "spiked" at molar ratios varying from ~1:12 to ~1:6, 200, respectively, corresponding to Kanamycin concentrations of 25 pM and 50 pM and an mRNA "background" of 300 nM. The results of these model assays indicate sufficient sensitivity and specificity to detect a specific message in the presence of other mRNA molecules at an abundance as low as ~3-5 copies per cell.

To test the predictions in Example III, namely that a further reduction in transcript length from ~150 nt to ~50 nt would produce a further enhancement in assay signal, mpmp-RT reactions were designed to generate 50 nt and/or 70 nt transcripts. Having demonstrated the enhancement in assay signal arising from the use of "5'-end-directed" capture probes (see Example III), capture probes were designed so as to target a subsequence near the transcript's 5' terminus.

Optimization of Assay Protocol—

In order to further improve assay sensitivity and dynamic range further, assay conditions were optimized. Specifically, RT primer concentrations in the Kanamycin mRNA titrations were reduced 25-fold (from 50 μM to 2 μM) and hybridization time was reduced by half (from 30 min to 15 min at 50° C.).

This protocol modification not only avoids saturation of the detector at the highest target concentration of ~500 pM (FIG. 10) but also reduces the background signal contributed by non-specific adsorption of fluorescently labeled RT primers and dCTPs remaining in the solution, thereby contributing to an extension in the dynamic range of the assay. A two-fold improvement was observed in assay sensitivity.

Example V—Optimization of Reverse Transcription of Model mRNA

To further improve upon assay performance of the mpmp-RT design reported in Example III, the Reverse Transcription (RT) protocol was optimized for 50 nt kanamycin transcripts—the best performer—by performing RT reactions under stringent temperature control. Using a programmable temperature profile in a thermocycler, the improved protocol for RT reactions in conjunction with stringent RT primer annealing and transcription conditions, an enhancement of fluorescence signal intensities by a factor of 2-3 was obtained (FIG. 19).

Specifically, RT reactions, configured as described in Example III, were performed in a thermocycler (Perkin-Elmer) ti implementing the following temperature profile:
RNA denaturation: 5 min at 65° C.;
Annealing: 30 min at 45° C.;
Annealing: 20 min at 38° C.;
SuperScript DI heat inactivation: 5 min at 85° C.; and Hold at 4° C.

Hybridization conditions were: incubation for 15 minutes at 50° C. in 1×TMAC, followed by 3 subsequent wash steps with the same buffer, each simply involving exchange of the 20 μl volume in contact with BeadChips by fresh buffer.

This 2-step protocol enforcing stringent RT conditions produced an enhancement in the specific fluorescence signal while leaving non-specific background signal comparable to that obtained earlier ("Protocol 2"), thus improving the signal to noise ratio of the assay about 2-fold.

Example VI—Spiking Experiments in Total Human RNA Background: Specificity

To further evaluate the level of specificity attainable in detecting a specific mRNA in the complex environment typical of a clinical human sample enriched with multiple RNA messages, an additional series of "spiking" experiments were performed by replacing the background of unknown total RNA of bacterial origin by total RNA from Human Placenta (Ambion). Total Human Placental RNA more realistically simulates conditions typically encountered in the determination of expression patterns of particular RNA species such as human interleukins and other cytokines in clinical samples.

Aliquots of Kanamycin mRNA, ranging in concentration from ~12.5 nM to ~50 pM, were spiked into solutions of total Human Placental RNA diluted to 100 ng/ul, corresponding to a concentration of ~300 nM. That is, the molar ratios of specific to non-specific mRNA ranged from 1:24 to 1:6,200. At each of eight ratios—including a no-target control—an RT reaction was performed separately under optimized assay conditions.

The results (FIG. 20B) follow the trend previously observed in the absence of total RNA. Thus, for a transcript of length 50 nt, spiked into a total RNA of human origin, the non-specific signal arising from the capture of fluorescently labeled cDNAs produced by randomly primed reverse transcription was insignificant compared to the specific signal generated by the capture of the entropically favored 50 nt Kanamycin cDNA. The lowest detected target level, at a molar ratio of ~1:6,200, corresponds to a concentration of ~50 pM of the specific mRNA, equivalent to approximately hundreds of copies per cell. Thus, this assay design attains a sensitivity and specificity comparable to that of commercially available expression profiling protocols (Lockhart et al, (1996)) not only in a mixture of eight unknown RNA in-vitro transcripts, but also in a complex environment using a real processed human sample.

Given the critical importance of specificity in multiplexed gene expression profiling, the previously reported Kanamycin "spiking" experiments to a pool of human placental RNAs was extended in order to simulate conditions relevant to clinical samples. The results are essentially identical in terms of specificity and sensitivity to those previously reported for spiking of in-vitro transcribed RNAs of bacterial origin, suggesting that the combination of producing short RT transcripts, directing capture probes to regions near the transcript's 5'-end and performing RT and hybridization under stringent conditions enhances specificity. Randomly primed RT transcripts generally will exceed the length of specific RT transcripts, providing the latter with a significantly entropic advantage in capture to immobilized probes.

The critical role of target entropy was again apparent under the optimized RT conditions. Thus, the biphasic plots in FIG. 21 again indicate a cross-over from a dilute regime characterized by a higher affinity constant to a "concentrated" regime with lower affinity constant. As previously discussed, effective affinity constants in the concentrated regime, reflecting the "crowding" of targets, are strongly transcript-length dependent. Indeed, slopes of the adsorption isotherms in the concentrated regime are substantially identical for the 50 nt transcripts produced under two different RT, reaction protocols (FIG. 19C). In contrast, in the dilute regime, the isotherm of the 50 nt unspiked transcript prepared by the stringent Protocol 3 displays a slope that is smaller by a factor of ~2.5 than that of the isotherm of the 50 nt unspiked transcript prepared under the less-stringent Protocol 2, indicating a correspondingly higher value for the affinity constant under improved RT conditions.

Example VII—Illustrative Applications

The assay formats described herein can be used for diagnosis and can, in certain cases, be used in connection with providing treatment.

Leukemia—

For example, International Application No. WO 03/008552 describes diagnosis of mixed lineage leukemia (MLL), acute lymphoblastic leukemia (ALL), and acute myellgenous leukemia (AML) according to the gene expression profile. These assay formats can also be used to analyze expression profiles of other genes, such as for Her-2, which is analyzed prior to administration of Herceptin™. The gene expression profile could also be useful in deciding on organ transplantation, or in diagnosing an infectious agent. The effect of a drug on a target could also be analyzed based on the expression profile. The presence of certain polymorphisms in cytokines, which can indicate susceptibility to disease or the likelihood of graft rejection, also can be analyzed with the format described herein. Other examples for the application of the methods of the invention include such the analysis of the host response to exposure to infectious and/or pathogenic agents, manifesting itself in a change of expression patterns of a set of designated genes ADME Panel—

Adverse drug reactions have been cited as being responsible for over 100,000 deaths and 2 million hospitalizations in one year in the USA. Individual genetic variation is responsible for a significant proportion of this. However, the indirect method of detecting genetic variation as a result of drug therapies is to monitor gene expression levels of the specific biomarkers.

The described methodology in Example I can be expanded to drug metabolism-associated genetic markers with approximately 200 genes that regulate drug metabolism. These important markers are available in flexible, customizable ADME (absorption-distribution-metabolism-excretion/elimination) panels. The first ADME panel is based on cytochrome P450, a super-family of 60 genes that govern many drug-metabolizing enzymes.

The new standard in multiplexed gene expression monitoring using BeadChips offers unprecedented accuracy, sensitivity and specificity. For instance, hMAP method followed by eMAP (elongation reaction) was applied to discrimination of closely related sequences of cytochrome P 450 gene family, namely, CYP 450 2B1 and 2B2. The established methodology on BeadChips allows to specifically measure 2-fold changes in gene expression levels of 96% homologous sequences in a highly multiplexed assay format.

Example VIII: Multiplexed Expression Monitoring: Cytokine mRNA Panel

Preparation of nine (9) Human Cytokine In-Vitro Transcripts—

To initiate the development of a custom BeadChip for multiplexed gene expression profiling of a clinically relevant panel of markers, we have designed a control system of nine (9) human cytokine mRNA targets, listed in Table III-1.

Full-length cDNA clones of seven cytokines (IL-2, -4, -6, -8, -10, TNF-$\alpha$ and IFN-$\gamma$) and two endogenous controls (GAPDH, Ubiquitin) were characterized by sequencing and recovered in the form of plasmid DNAs containing specific cytokine cDNA inserts in pCMV6 vector (OriGene Technologies, Md.). PCR primers to the cloning vector sequence were designed to amplify all cDNAs with a standard primer pair, thus eliminating the substantial cost of target-specific PCR amplification. Positioning of the Forward PCR primer upstream of the T7 promoter sequence—located next to the cloning site of every cytokine insert (cDNA)—enables T7 in-vitro transcription of only the specific cDNA sequence located at the 5'-end of the target of interest. Following in-vitro transcription (MegaScript, Ambion), templates were characterized for purity in agarose gel using SybrGreen staining; DNA concentrations were determined by optical absorption following 200-fold dilution.

Next, a multiplexed RT reaction was performed using a set of nine gene-specific RT primers to produce a pool of nine Cy3-labeled cDNAs, according to the optimized protocol we developed for Kanamycin. Specifically, we applied our empirical design rules (see below) to select RT primers so as to produce cDNAs 50 nt to 70 nt in length while minimizing cross-hybridization. This pool of cDNAs was placed, without any purification, onto a BeadChip containing eleven types of encoded beads displaying specific capture probes designed for the set of seven cytokine cDNAs as well as two endogenous positive controls and two negative controls, namely a oligo-C18 (SEQ ID NO: 30) and Kanamycin.

First results based on the empirical design rules for primer/probe selection demonstrated the ability of Random Encoded Array Detection (READ) format of multiplexed analysis to determine expression levels of multiple designated cytokine genes. However, two mRNA targets in 9-plex assay were detected with the signal intensity close to the marginal threshold of unspecific background signal, as a result of cross-reactive binding of the corresponding RT primers to other mRNA targets in a complex sample pool. These results indicated an urgent need in the further optimization of primer/probe design rules involving user-friendly computational tools based on the mathematical algorithms which we disclosed above.

Using the second version of our design rules for RT primer and capture probe selection, we have re-designed 11 sets of capture probes with the corresponding reverse transcription primers specific for each mRNA of interest (Table III-1). To increase specificity of hybridization reactions between RT primers and targets, we also extended length of primer sequences to ~20 nucleotides in length. Based on calculated melting temperatures for the re-designed RT primers and capture probes, we performed the RT reaction with a higher stringency than earlier, using a 2-step profile, starting with RNA denaturation at 70° C. for 5 min, followed by primer annealing and extension at 52° C. for 60 min. On chip hybridization was performed at 57° C.—an average Tm of the nine re-designed probes.

Next, a multiplexed RT reaction was performed on 9 in vitro transcribed RNAs, containing 32 femtomoles of each message, using a set of nine gene-specific RT primers to produce a pool of nine Cy3-labeled cDNAs in accordance with the 2-step temperature incubation protocol we optimized as discussed above. Specifically, we applied our computational design rules (see Report IV) to select RT primers so as to produce cDNAs from 60 nt to 200 nt in length while minimizing cross-hybridization (see above).

This pool of directly labeled Cy3-cDNAs, containing 16 femtomoles of each added mRNA, was placed, without any purification, onto a BeadChip containing eleven types of encoded beads displaying specific capture probes designed for the set of seven cytokine cDNAs as well as two endogenous positive controls and two negative controls, namely a oligo-C18 (SEQ ID NO: 30) and Kanamycin. The results presented in FIG. 26 demonstrate multiplexed reproducible detection of six cytokine cDNAs, IL-6 having been omitted from the RT reaction to provide an indication of the low level of non-specific hybridization. The signal to noise ratios were reproducible within the range from 3.5 to 6 (see Table III-2, included in FIG. 24A), that confirms statistical significance of signal output for every message detected. Bead-Chips included ~300 beads for each of the cDNAs—this redundancy provides an added level of reliability.

TABLE III-1

Set of 9 human Cytokine cDNA Clones for Multiplexed Analysis: Designs of Reverse Transcription Primers and Capture Probes of the Analytes.

| No | Accession No. | Sample Description | RT primer | Capture Probe | Bead Code |
|---|---|---|---|---|---|
| 1 | NM_000206 | Homo sapiens interleukin 2 receptor, gamma (IL2RG), mRNA | ATTGGGCGTC AGAATTGTCG 20-mer, 62.0C SEQ ID NO. 12 | ATGTTGAAGCCAT CATTACCATTC 25-mer, 62.6C SEQ ID NO. 13 | G5B |
| 2 | NM_152899 | Homo sapiens interleukin 4 induced 1 (IL4I1), transcript variant 1, mRNA | GGACGAGGAC GAGGAGGT 18-mer, Tm = 63.6C SEQ ID NO. 14 | TGTCCTGCTGTCAC CAAGAG 20-mer, Tm = 62.7C SEQ ID NO. 15 | G5C |
| 3 | NM_000565 | Homo sapiens interleukin 6 receptor (IL6R), mRNA | GCTAATGGGA ACCGGGC 17-mer, Tm = 61.5C SEQ ID NO. 16 | CAGTGTGTGTAGA GAGCCGG 20-mer, Tm = 63.1C SEQ ID NO. 17 | G5D |
| 4 | NM_000584 | Homo sapiens interleukin 8 (IL8), mRNA | TCTTTAGCACT CCTTGGCAAA 21-mer, 60.8C SEQ ID NO. 18 | GTGTAGGCACTGA GGACGG 22-mer, 64.3 SEQ ID NO. 19 | G5E |
| 5 | NM_001558 | Homo sapiens interleukin 10 receptor alpha (IL10RA), mRNA | ATGAGCGTCT GAGCCAAGA 19-mer Tm = 62.0C SEQ ID NO. 20 | ATGCTGCCGTGCC TCGTAG 19-mer, Tm = 66.1C SEQ ID NO. 21 | G5F |
| 6 | NM_001066 | Homo sapiens tumor necrosis factor receptor superfamily, member 1B. TNFRSF1B, mRNA | TCATAGTATTC TCTGAGCCGG 19-mer, 59.4C SEQ ID NO. 22 | CAGGTGGCATTTA CACCCTACG 22-mer, 64.3C SEQ ID NO. 23 | G3B |
| 7 | NM_018955 | Homo sapiens ubiquitin B (UBB), mRNA | GTCTTGCCGGT AAGGGTT 18-mer, Tm = 60.4C SEQ ID NO. 24 | GCAGGATCCTGGT ATCCGCTA 21-mer, Tm = 64.4C SEQ ID NO. 25 | G3C |
| 8 | NM_002046, | Homo sapiens glyceraldehyde-3-phosphate dehydrogenase (GAPD), mRNA | ACGGTGCCAT GGAATTTGC 19-mer, Tm = 62.8C SEQ ID NO. 26 | GGAGTCAACGGAT TTGGTCGT 21-mer, Tm = 63.6C SEQ ID NO. 27 | G3D |
| 9 | NM_000416 | Homo sapiens interferon gamma receptor (IFNGR1), mRNA | GTGTAGGCAC TGAGGACGG 19-mer, Tm = 63C SEQ ID NO. 28 | GCATGGCTCTCCT CTTTCTCC 21-mer, Tm = 63.5C SEQ ID NO. 29 | G3E |
| 10 | Neg control | Control for unspecific binding of nucleic acids | none | Oligo-C18 SEQ ID NO. 30 | G2A |
| 11 | Neg control, Non-human | Kanamycin mRNA not present in a multiplexed mix | none | TACAAGCTTGGGC GTGTCTC 20-mer, Tm = 63.4C SEQ ID NO. 31 | G2B |

Example IX: Analysis of Highly Homologous mRNA Sequences in Maize Zein Gene Family In the two inbred maize lines B73 and BSSS53, certain mRNA sequences of the zein gene display a degree of 95% to 99% homology over the entire 945 nt of the sequence. FIGS. 27 and 28 illustrates the placement of capture and elongation probes to target specific mutations (highlighted in red) for detection of seven highly expressed mRNA sequences in the inbred maize line BSSS53.

The task of detecting these sequences and estimating their respective expression levels with current methods is a very laborious process, requiring of sequencing large sets of clones. A combination of elongation-mediated and hybridization-mediated detection methodologies is useful in discriminating between highly homologous sequences of mRNAs, while simultaneously determining respective abundances of these messages in a highly parallel format of analysis. The detection assay was performed as follows.

First, the RT reaction was performed on the processed total RNA samples using specific RT primer (highlighted in yellow) to convert mRNAs of interest into Cy3-labeled cDNAs. Seven cDNA targets were hybridized on a BeadChip to a perfectly matched capture/elongation probe. The probes are designed such that the 3'-end of each probe aligns with each unique polymorphic position in the targets. The matched hybridized probes were elongated using TAMRA-labeled dCTP. Therefore, elongated probes would emit a fluorescent signal.

Figure 29:
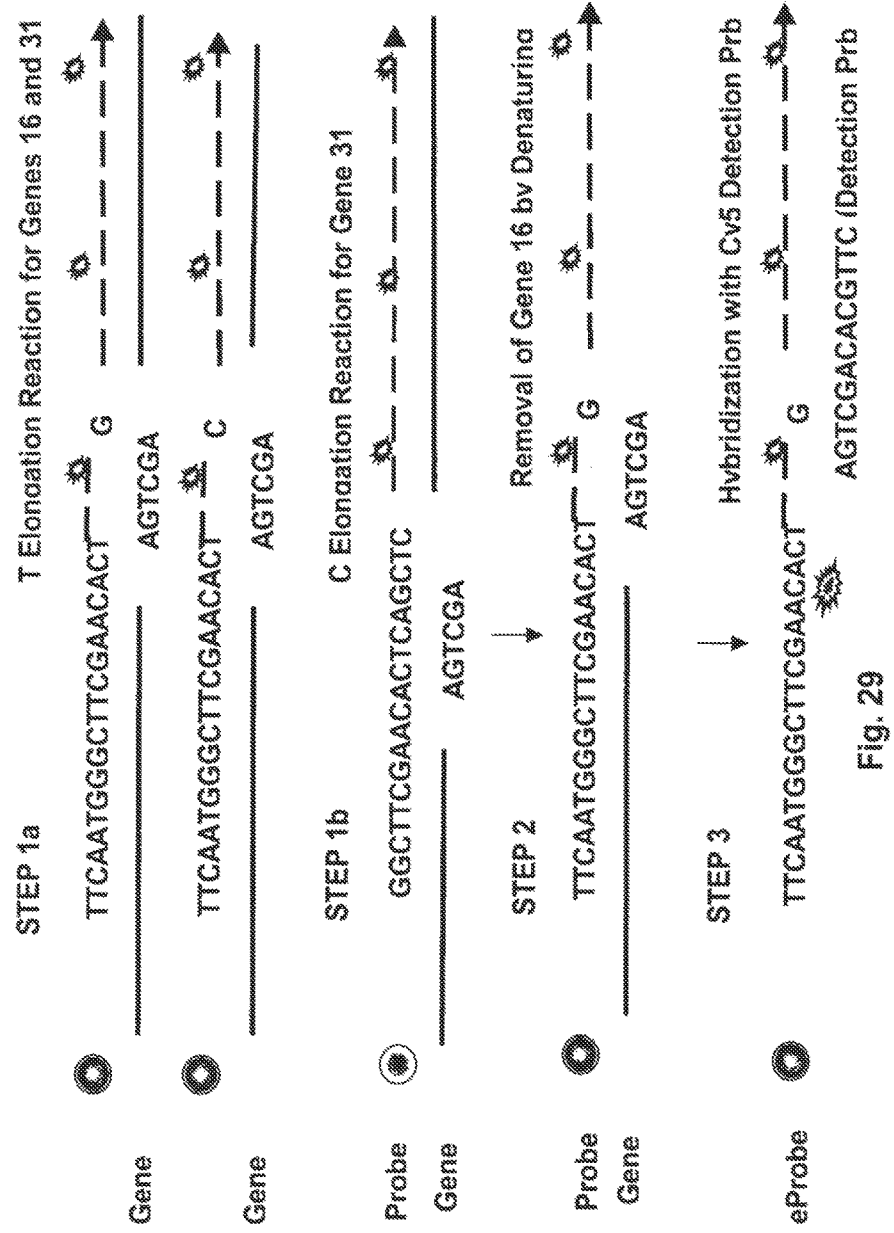
FIG. 29 shows a design combining hybridization and elongation permitting detection of closely homologous genes 16 and 31 identified in FIG. 28 (FIG. 29 discloses SEQ ID NOS 46, 46, 47, 46, 46, and 48, respectively, in order of appearance)

A more complicated case of sequence discrimination, involving two sequences having a common mutation, but only one having a second specific mutation is illustrated in FIG. 29. Specifically, genes 16 and 31 have the same mutation T (replacing C), that discriminates them from all the other sequences in multiple sequence alignment (not shown). Gene 31 is detected using a second specific capture/elongation probe to discriminate a unique mutation C (replacing G). However, gene 16 does have another specific mutation which permits its identification in a pool of 7 closely homologous sequences by a "phasing" design. As depicted in detail in FIG. 29, in order to ensure discrimination, this design calls for three steps; steps 1 and 2 occur simultaneously.

Step 1:

Probe 16, with T at the 3'-end, was immobilized on bead type 1 and placed under annealing conditions in contact with a pool of 7 amplified gene transcripts. Elongation following hybridization discriminated two genes, 16 and 31, from the other sequences in the pool, as detected by the TMRA fluorescence from beads carrying the probes. Simultaneously, probe 31, with C at the 3'-end, was immobilized on another bead type and placed in hybridizing conditions with a pool of 7 amplified gene transcripts. An elongation reaction followed hybridization, and gene 31 was detected by TMRA fluorescence from a particular encoded bead type.

Step 2:

The next stage of the assay is removal of the target 16 from the elongated probe 16, by a denaturation reaction at 95° C.

Step 3:

The single-stranded elongated probe 16 is then hybridized with a short Cy5-labeled detection probe 16 at the melting temperature of the duplex formation (Tm=49° C.) using a matched probe with C in the middle of the sequence. If hybridization at the indicated melting temperature (Tm) occurs, and therefore Cy5 fluorescence is detected on beads of type 1, this indicates that gene 16 is present in the pool. Thus, in this design, a TMRA signal recorded from the bead type carrying probe 31 confirms the presence of gene 31 and a TMRA signal recorded with subsequent Cy5 signal from the bead type carrying probe 16 confirms the presence of gene 16.

It should be understood that the terms, expressions and examples used herein are exemplary only and not limiting and that the scope of the invention is defined only in the claims which follow, and includes all equivalents of the subject matter of the claims. All steps in method claims can be performed in any order, including that set forth in the claims, unless otherwise stated in the claims.

What is claimed is:

1. A method of detecting differences in families of related genomic sequences where the family is derived from a particular species, and where the members of the families have two or more related subsequences which are similar in sequence, and at least one of said related subsequences (designated "S1") differ in sequence, among certain members of the family, by 3 or more consecutive nucleotides, and at least one of said related subsequences (designated "S2") differ in sequence, among certain members of the family, by less than 3 consecutive nucleotides; wherein a dual assay format is employed, comprising:

amplifying the regions of the related genomic sequences which include the subsequences S1 and S2, or reverse transcribing the mRNA regions which include the subsequences S1 and S2, to thereby at least four distinct sets of oligonucleotides, the sets respectively including:

(i) an oligonucleotide (of sequence F1S1) derived from subsequence S1 and an oligonucleotide (of sequence F1S2) derived from subsequence S2;
(ii) an oligonucleotide (of sequence F2S1) derived from subsequence S1 and an oligonucleotide (of sequence F1S2) derived from subsequence S2;
(iii) an oligonucleotide (of sequence F1S1) derived from subsequence S1 and an oligonucleotide (of sequence F2S2); and
(iv) an oligonucleotide (of sequence F2S1) derived from subsequence S1 and an oligonucleotide (of sequence F2S2);

providing a first set of oligonucleotide probes capable of hybridizing to F1S1, a second set of oligonucleotide probes capable of hybridizing to F2S1, a third set of oligonucleotide probes capable of hybridizing to F1S2, and a fourth set of oligonucleotide probes capable of hybridizing to F2 S2, each set of oligonucleotide probes being encoded so as to permit discrimination among sets; wherein, following hybridization of the four sets of oligonucleotides with the four sets of oligonucleotide probes, oligonucleotides including either F1S1 or F2S1 can be detected because they are labeled with a first color, and oligonucleotides including F1S2 or F2S2 will, following an elongation reaction, be labeled with a detectable second color;

contacting the four sets of oligonucleotides with the four sets of oligonucleotide probes under conditions conducive to hybridization and elongation, such that oligonucleotides including either F1S1 or F2S1 can be detected because they will be labeled with the first color, and oligonucleotides including F1S2 or F2S2 will, following the elongation reaction, be labeled with the detectable second color;

analyzing the pattern of hybridization and elongation, by detecting and analyzing the presence of the first and second colors; and determining which of the four sets of oligonucleotides (F1S1, F2S1, F1S2, F2S2) is present in the sample based on the analysis.

2. The method of claim 1 wherein the encoding of the four sets of oligonucleotide probes is achieved by attaching different sets to differently encoded beads.

3. The method of claim 1 wherein the oligonucleotide probe is elongated, and the elongation product includes a labeled nucleotide incorporated therein.

4. The method of claim 1 wherein members of the sets of oligonucleotides are labeled by performing reverse transcription using a labeled primer.

* * * * *

SEQUENCE LISTING

<160> NUMBER OF SEQ ID NOS: 48

<210> SEQ ID NO 1
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agggtaaaat taagcacagt ggaagaattt cattctgttc tcagttttcc tggattatgc      60
ctggcaccat taaagaaaat atcatctttg gtgtttccta tgatgaatat agaagcgtca     120
tcatcaaagc atgccaacta gaagaggtaa gaaactatgt gaaaactttt tg             172

<210> SEQ ID NO 2
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcagttttcc tggattatgc ctggcaccat taaagaaaat atcatctttg gtgtttccta     60
tgatgaatat agaagcgtca tcatcaa                                          87

<210> SEQ ID NO 3
<211> LENGTH: 40

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caccattaaa gaaatatca tctttggtgt ttcctatgat                              40

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaaaatatca tctttggtgt ttcct                                            25

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cttttatagt agaaa                                                       15

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cttttatagt agaaacc                                                     17

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cttttatagt agaaaccac                                                   19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cttttatagt agaaaccaca a                                                21

<210> SEQ ID NO 9
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 9
cttttatagt agaaaccaca aagga                                          25

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cttttatagt agaaaccaca aaggatacta                                     30

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cttttatagt agaaaccaca aaggatacta cttat                               35

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
attgggcgtc agaattgtcg                                                20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
atgttgaagc catcattacc attc                                           24

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggacgaggac gaggaggt                                                  18

<210> SEQ ID NO 15
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 15
tgtcctgctg tcaccaagag                                                 20

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctaatggga accgggc                                                    17

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cagtgtgtgt agagagccgg                                                 20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctttagcac tccttggcaa a                                               21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gtgtaggcac tgaggacgg                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgagcgtct gagccaaga                                                  19

<210> SEQ ID NO 21
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 21
atgctgccgt gcctcgtag                                                  19

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcatagtatt ctctgagccg g                                               21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
caggtggcat ttacacccta cg                                              22

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtcttgccgg taagggtt                                                   18

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gcaggatcct ggtatccgct a                                               21

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acggtgccat ggaatttgc                                                  19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
          probe

<400> SEQUENCE: 27
ggagtcaacg gatttggtcg t                                            21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtgtaggcac tgaggacgg                                               19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gcatggctct cctctttctc c                                            21

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cccccccccc cccccccc                                                18

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tacaagcttg ggcgtgtctc                                              20

<210> SEQ ID NO 32
<211> LENGTH: 300
<212> TYPE: DNA
<213> ORGANISM: Zea mays

<400> SEQUENCE: 32
ataatatttt gagcattcag aaacacacca agcgaagcac attagcaaca acctaacaac    60
aatggctacc aagatatttat ccctccttgc gcttcttgcg cttttgcga gcgcaacaaa   120 tgcgttcatt attccacaat gctcacttgc tccaagttcc attattacac agttcctccc   180
accagttact tcaatgggct tcgaacaccc agctgtgcaa gcctataagc tacaacaagc   240
aattgcggcg agcgtcttac aacaaccaat ttcccagttg caacaacaat ccttggcaca   300

<210> SEQ ID NO 33
<211> LENGTH: 300
```

```
<212> TYPE: DNA
<213> ORGANISM: Zea mays

<400> SEQUENCE: 33
ataatatttt gagcattcag aaacacacca agcgaagcgc actagcaaca acctaacaac      60
aatggctacc aagatattat ccctccttgc gcttcttgcg cttttttgcga gcgcaacaaa    120 tgcgtccatt attccacaat gctcacttgc tcctagttcc attattccac agttcctccc    180
accagttact tcaatggcct tcgaacaccc agctgtgcaa gcctataagc tacaacaagc    240
gattgcggcg agcgtcttac aacaaccaat tgcccaattg caacaacaat ccttggcaca    300

<210> SEQ ID NO 34
<211> LENGTH: 300
<212> TYPE: DNA
<213> ORGANISM: Zea mays

<400> SEQUENCE: 34
ataatacttt gagcattcag aaacacacca agcgaagcgc actagcaacg accaaacaac     60
aatggctacc aagatattag ccctccttgc gcttcttgcc ctttttgtga gcgcaacaaa    120
tgcgttcatt attccacaat gctcacttgc tcctagtgcc attattccac agttcctccc    180
accagttact tcaatgggct tcgaacactc agctgtgcaa gcctacaagc tacaacaagc    240
gcttgcggcg agcgtcttac aacaaccaat tgcccaattg caacaacaat ccttggcaca    300

<210> SEQ ID NO 35
<211> LENGTH: 300
<212> TYPE: DNA
<213> ORGANISM: Zea mays

<400> SEQUENCE: 35
ataatatttt gagcattcag aaacacacca agcgaagcgc actagcaacg accaaacaac     60
aatggctacc aagatattag ccctccttgc gcttcttgcc ctttttgtga gcgcaacaaa    120
tgcgttcatt attccacaat gctcacttgc tcctagtgcc attattccac agttcctccc    180
accagttact tcaatgggct tcgaacactc agctctgcaa gcctacaagc tacaacaagc    240
gcttgcggcg agcgtcttac aacaaccaat tgcccaattg caacaacaat ccttggcaca    300

<210> SEQ ID NO 36
<211> LENGTH: 300
<212> TYPE: DNA
<213> ORGANISM: Zea mays

<400> SEQUENCE: 36
ataatatttt gagcattcag aaacacacca agcgaagctt actagcaacg acttaacaac     60
aatggctacc aagatattag ccctccttgc gcttcttgcc ctttttgtga gcgcaacaaa    120
tgcgttcatt attccacaat gctcacttgc tcctagtgcc attataccac agttcctccc    180
accagttact tcaatgggct tcgaacacct agctgtgcaa gcctacaacc tacaacaagc    240
gcttgcggcg agcgtcttac aacaaccaat taaccaattg caacaacaat ccttggcaca    300

<210> SEQ ID NO 37
<211> LENGTH: 276
<212> TYPE: DNA
<213> ORGANISM: Zea mays

<400> SEQUENCE: 37
ataatatttt gagcattcaa aaacacacca agcgaagctc actagcaacg acctaacaac     60
```

```
aatggctacc aagatattag ccctccttgc gcttcttgcc cttttgtga gcgcaacaaa    120 tgcgttcatt attccacaat gctcacttgc tcctagtgcc attattccac agttcctccc    180
accagttact tcaatgggct tcgaacacct agctgtgcaa gcctacagcc tacaacaagc    240
gcttacggcg agcgtcttac aacaaccaat tgacca                              276
```

<210> SEQ ID NO 38
<211> LENGTH: 300
<212> TYPE: DNA
<213> ORGANISM: Zea mays

<400> SEQUENCE: 38

```
ataatatttt cagcattcaa aaacacacca agcgaagcgc actagcaacg acctaacacc    60
aatggctacc aagatattag ccctccttgc gcttcttgcc cttttagtga gcgcaacaaa    120
tgcgttcatt attccacagt gctcacttgc tcctagtgcc agtattccac agttcctccc    180
accagttact tcaatgggct tcgaacatcc agccgtgcaa gcctacaggc tacaactagc    240
gcttgcggcg agcgccttac aacaaccaat tgcccaattg caacaacaat ccttggcaca    300
```

<210> SEQ ID NO 39
<211> LENGTH: 60
<212> TYPE: DNA
<213> ORGANISM: Zea mays

<400> SEQUENCE: 39

```
accagttact tcaatgggct tcgaacaccc agctgtgcaa gcctataggc tacaacaagc    60
```

<210> SEQ ID NO 40
<211> LENGTH: 60
<212> TYPE: DNA
<213> ORGANISM: Zea mays

<400> SEQUENCE: 40

```
accagttact tcaatggcct tcgaacaccc agctgtgcaa gcctataggc tacaacaagc    60
```

<210> SEQ ID NO 41
<211> LENGTH: 60
<212> TYPE: DNA
<213> ORGANISM: Zea mays

<400> SEQUENCE: 41

```
accagttact tcaatgggct tcgaacactc agctgtgcaa gccaacaggc tacaacaagc    60
```

<210> SEQ ID NO 42
<211> LENGTH: 60
<212> TYPE: DNA
<213> ORGANISM: Zea mays

<400> SEQUENCE: 42

```
accagttact tcaatgggct tcgaacactc agctctgcaa gccaacaggc tacaacaagc    60
```

<210> SEQ ID NO 43
<211> LENGTH: 60
<212> TYPE: DNA
<213> ORGANISM: Zea mays

<400> SEQUENCE: 43

```
accagttact tcaatgggct tcgaacacct agctgtgcaa gcctacaagc tacaacaagc    60
```

<210> SEQ ID NO 44
<211> LENGTH: 60

```
<212> TYPE: DNA
<213> ORGANISM: Zea mays

<400> SEQUENCE: 44
accagttact tcaatgggct tcgaacacct agctgtgcaa gcctacaggc tacaacaagc      60

<210> SEQ ID NO 45
<211> LENGTH: 60
<212> TYPE: DNA
<213> ORGANISM: Zea mays

<400> SEQUENCE: 45
accagttact tcaatgggct tcgaacatcc agccgtgcaa gcctacaggc tacaactagc      60

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ttcaatgggc ttcgaacact                                                  20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ggcttcgaac actcagctc                                                   19

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
agtcgacacg ttc                                                         13
```